US008000900B2

(12) United States Patent
Heckerman et al.

(10) Patent No.: US 8,000,900 B2
(45) Date of Patent: Aug. 16, 2011

(54) ASSOCIATION-BASED PREDICTIONS OF PATHOGEN CHARACTERISTICS

(75) Inventors: David E. Heckerman, Bellevue, WA (US); Simon Mallal, East Perth (AU); Carl M. Kadie, Bellevue, WA (US); Corey Benjamin Moore, North Lake (AU); Nebojsa Jojic, Redmond, WA (US)

(73) Assignee: Microsoft Corporation, Redmond, WA (US)

( * ) Notice: Subject to any disclaimer, the term of this patent is extended or adjusted under 35 U.S.C. 154(b) by 1194 days.

(21) Appl. No.: 11/324,634

(22) Filed: Dec. 30, 2005

(65) Prior Publication Data

US 2006/0160071 A1      Jul. 20, 2006

Related U.S. Application Data

(63) Continuation-in-part of application No. 10/977,415, filed on Oct. 29, 2004, now abandoned, and a continuation-in-part of application No. 10/493,165, filed on Sep. 21, 2004, now abandoned.

(51) Int. Cl.
*G01N 33/50*   (2006.01)
*G01N 31/00*   (2006.01)

(52) U.S. Cl. ................ 702/19; 702/20; 702/30

(58) Field of Classification Search .................. None
See application file for complete search history.

(56) References Cited

U.S. PATENT DOCUMENTS

| | | | |
|---|---|---|---|
| 3,791,932 A | 2/1974 | Schuurs et al. |
| 3,839,153 A | 10/1974 | Schuurs et al. |
| 4,051,728 A | 10/1977 | Metz |
| 4,235,871 A | 11/1980 | Papahadjopoulos et al. |
| 4,342,566 A | 8/1982 | Theofilopolous et al. |
| 4,493,795 A | 1/1985 | Nestor, Jr. et al. |
| 4,671,958 A | 6/1987 | Rodwell et al. |
| 4,900,811 A | 2/1990 | Sutcliffe |
| 5,019,369 A | 5/1991 | Presant et al. |
| 5,426,039 A | 6/1995 | Wallace et al. |
| 5,698,767 A | 12/1997 | Wilson et al. |
| 5,709,843 A | 1/1998 | Reisner |
| 2002/0182222 A1 | 12/2002 | Groot |
| 2004/0072249 A1 | 4/2004 | Hoffman et al. |

OTHER PUBLICATIONS

"Q&A. Microsoft Researchers Use Machine Learning Techniques to Help Advance HIV Vaccine Research" http://www.microsoft.com/presspass/features/2005/feb05/02-23HIVResearch mspx 5 pgs Last Accessed: Sep. 15, 2006.
"Microsoft Research Collaborates With HIV Researchers to Create Advanced Vaccine Models Fact Sheet" http://www.microsoft.com/presspass/press/2005/feb05/0223HIVVaccineFS mspx 3 pgs Last Accessed: Sep. 15, 2006.
"Microsoft Scientists Search for Breakthroughs in HIV Vaccine Design" http://www.microsoft.com/presspass/press/2005/feb05/02-23HIVVaccinePR.mspx. 3 pgs. Last Accessed: Sep. 15, 2006.
Moore et al. "Evidence of HIV-1 Adaptation to HLA-Restricted Immune Responses at a Population Level." Science, vol. 296, Issue 5572, pp. 1439-1443, May 24, 2002.
McKinney et al. "Recognition of Variant HIV-1 Epitopes from Diverse Viral Subtypes by Vaccine-Induced OTL1." The Journal of Immunology, 2004, pp. 1941-1950, vol. 173.
"CTLPred: A SVM & ANN Based CTL epitope Prediction method" http://www.imtech.res.in/raghava/ctlpred/about html 7 pgs Last Accessed: Sep. 15, 2006.
"HIV Databases" http://www.hiv.lanl.gov/content/index. Last Accessed: Feb. 13, 2007. 2 pgs.
"SYFPEITHI" http://www.SYFPEITHI.de Last Accessed Sep. 15, 2006 1 pg.
Kohavi. "A study of cross-validation and bootstrap for accuracy estimation and model selection." In Proceedings of the Fourteenth International Joint Conference on Artificial Intelligence, pp. 1137-1143. San Mateo, CA: Morgan Kaufmann, 1995 7 pgs.
Allen, et al., "Selection, Transmission, and Reversion of an Antigen-Processing Cytotoxic T-Lymphocyte Escape Mutation in Human Immunodeficiency Virus Type 1 Infection." Journal of Virology, Jul. 2004, pp. 7069-7078, vol. 78, No. 13, 10 pgs.
Leslie, et al., "Transmission and accumulation of CTL escape variants drive negative associations between HIV polymorphisms and HLA." JEM, Mar. 21, 2005 pp. 891-902, vol. 201, No. 6 12 pgs.
Leslie et al., "HIV evolution CTL escape mutation and reversion after transmission." Nat Med 10(3):282-289. 2004 25 pgs.
Parker et al. "Scheme for ranking potential HLA-A2 binding peptides based on independent binding of individual peptide side-chains." Journal of Immunology. 1994. 152:163-75, 13 pgs.
Jojic et al. "Using 'epitomes' to model genetic diversity Rational design of HIV vaccine cocktails." Presented at The Conference on Neural Information Processing Systems on Dec. 7, 2005, 7 pgs.
Bhasin et al. "MHCBN: A comprehensive database of MHC binding and non binding peptides." Bioinformatics (2003) vol. 19, 665-666, 2 pgs.
Rammensee et al. "SYFPEITHI: database for MHC ligands and peptide motifs," Immunogenetics (1999) 50:213-219, 7 pgs.
Nolan et al. "Impact of host genetics on HIV disease progression and treatment: new conflicts on an ancient battle ground." AIDS. vol. 18(9). Jun. 18, 2004. pp. 1231-1240. 14 pgs.
Feeney et al. "HIV-1 viral escape in infancy followed by emergence of a variant-specific CTL response." Journal of Immunology. Jun. 15, 2005: 174(12) pp. 7524-7529, 7 pgs.

(Continued)

*Primary Examiner* — Lori A Clow
(74) *Attorney, Agent, or Firm* — Lee & Hayes, PLLC

(57) ABSTRACT

A system comprising a machine learning classifier trained on a plurality of associations between a host and a pathogen to predict a pathogen characteristic is described herein. The pathogen characteristic can relate to a disease state of the host. Computer-executable instructions for performing a method of forecasting a portion of a target molecule anticipated to influence an organism's condition also are described herein. The method comprises employing population data to automatically analyze one or more areas of the target molecule to determine the portion of the target molecule anticipated to influence the organism's condition. The population data can pertain to at least one relationship between at least one diverse organism trait and the target molecule. One or more epitopes forecast by employing the method also are contemplated.

17 Claims, 24 Drawing Sheets

OTHER PUBLICATIONS

Mallal. "HIV adaptation to genetic polymorphisms of the host." 10th Conference on Retroviruses and Opportunistic Infections. Boston, MA, Feb. 10-14, 2003, 1 pg.

Mallal et al. "HIV adaptation to HLA-restricted immune responses—implications for vaccine design and evaluation." 10th Conference on Retroviruses and Opportunistic Infection, Boston, MA, Feb. 10-14, 2003, Abstract No. C-27 (327), 1 pg.

Allen et al. "Sterotypic escape from CDB+ T cell responses represents a major driving force of HIV-1 sequence diversity and reveals constraints on HIV-1 evolution" 12th Conference on Retroviruses and Opportunistic Infections. Boston, MA, Feb. 22-25, 2005, Abstract No. 463, 1 pg.

Park et al. "HLA-restricted immune responses have driven the evolution of HIV-1 clades." 12th Conference on Retroviruses and Opportunistic Infections, Boston, MA, Feb. 22-25, 2005, 2 pgs.

Jojic et al., HLA-driven optimization of an HIV vaccine immunogen. 12th Conference on Retroviruses and Opportunistic Infections, Boston USA, Feb. 22-25, 2005, Session 89 Poster Abstracts 2 pgs.

"Q&A: Microsoft Researchers Use Machine Learning Techniques to Help Advance HIV Vaccine Research." http://www.microsoft.com/presspass/features/2005/feb05/02-23HIVResearch.mspx. Last accessed on Feb. 13, 2007, 5 pgs.

"Microsoft Research Collaborates With HIV Researchers to Create Advanced Vaccines Models Fact Sheet." http://www.microsoft.com/presspass/press/2005/feb05/0223HIVVaccineFS.mspx. Last accessed on Sep. 25, 2006, 3 pgs.

Bhasin et al. "Prediction of CTL epitopes using QM, SVM and ANN techniques." http://www.ncbi.nlm.nih.gov/entrez/query.fcgi?CMD=Display&DB=pubmed. Last accessed on Sep. 25, 2006, 2 pgs.

Jin et al. "Identification of Subdominant Cytotoxic T Lymphocyte Epitopes Encoded by Autologous HIV Type 1 Sequences, Using Dendritic Cell Stimulation and Computer-Driven Algorithm." Aids Research and Human Retroviruses. vol. 16, No. 1, 2000. pp. 67-76, 10 pgs.

Bird et al. "HLA typing in a Kenyan cohort identifies novel class I alleles that restrict cytotoxic T-cell responses to local HIV-1 clades." AIDS, 2002, vol. 16, pp. 1899-1904 6 pgs.

Fang et al "Analysis of Transition from Long-Term Nonprogressive to Progressive Infection Identifies Sequences that May Altenuate HIV Type 1." Aids Research And Human Retroviruses. vol. 17, No. 15, 2001, pp. 1395-1404, 10 pgs.

Yuste et al. "Unusual Distribution of Mutations Associated with Serial Bottieneck Passages of Human Immunodeficiency Virus Type 1." Journal of Virology. vol. 74, No. 20. Oct. 2000, p. 9546-9552 7 pgs.

Anderson et al. "Nel from Primary Isolates of Human Immunodeficiency Virus Type 1 Suppresses Surface CD4 Expression in Human and Mouse T Cells." Journal of Virology, Aug. 1993, vol. 67, No. 8, p. 4923-4931 9 pgs.

Gunthard et al. "Human Immunodeficiency Virus Replication and Genotypic Resistance in Blood and Lymph Nodes after a Year of Potent Antiretroviral Therapy." Journal of Virology. Mar. 1998, p. 2422-2428, vol. 72, No. 3, 7 pgs.

Desire et al. "Quantification of Human Immunodeficiency Virus Type 1 Proviral Load by a TaqMan Real-Time PCR Assay." Journal of Clinical Microbiology, Apr. 2001, vol. 39, No. 4, p. 1303-1310, 8 pgs.

Connor et al. "Immunological and Virological Analyses of Persons Infected by Human Immunoxieficiency Virus Type 1 white Participating in Trials of Recombinant gp120 Subunit Vaccines." Journal of Virology vol. 72, No. 2, Feb. 1998, pp. 1552-1576.

Peters et al. "Resistance to Nucleoside Analog Reverse Transcriptase Inhibitors Mediated by Human Immunodeficiency Virus Type 1 p6 Protein." Journal of Virology, vol. 75, No. 20 Oct. 2001, pp. 9644-9653, 10 pgs.

Carr et al. "Diverse BF recombinants have spread widely since the introduction of HIV-1 into South America" AIDS 2001, vol. 15 No. 15, p. 41-47, 7 pgs.

Macriota et al. "Detection of Simian Immunodeficiency Virus in Diverse Species and of Human Immunodeficiency Virus Type 2 by Using Consensus Primers within the poi Region." Journal of Clinical Microbiology. Sep. 2002, vol. 40, No. 9, 5 pgs.

Holguin et al. "Prevalence of Human Immunodeficiency Virus Type 1 (HIV-1) Non-8 Subtypes in Foreigners Living in Madrid, Spain, and Comparison of the Performances of the AMPLICOR HIV-1 Monitor Version 1.0 and the New Automated Version 1 5." Journal of Clinical Microbiology, May 2001, p. 1850-1854, vol. 39, No. 5, 5 pgs.

Schueler-Furman et al. "Structure-based prediction of binding peptides to MHC class I molecules Application to a broad range of MHC alleles" Protein Science, 2000. vol. 9, pp. 1838-1846 9 pgs.

"Microsoft Scientists Search for Breakthroughs in HIV Vaccine Design." http://www.microsoft.com/presspass/press/2005/feb05/02-23HIVVaccinePR.mspx. Last accessed on Sep. 25, 2006, 3 pgs.

Bailey, et al., "Unsupervised Learning of Multiple Motifs in Biopolymers Using Expectation Maximization", Machine Learning, vol. 21, pp. 51-80, 1995.

Blankenbecler, et al., "Matching Protein Structures with Fuzzy Alignments", PNAS, vol. 100 No. 21, pp. 11936-11940, Oct. 12, 2003.

Brejova, et al., "Finding Patterns in Biological Sequences", Technical Report University of Waterloo, pp. 1-49, Dec. 2000.

De Groot, et al., "From Genome to Vaccine: In Silico Predictions, Ex Vivo Verification", Vaccine, vol. 19, pp. 4385-4395, 2001.

Hernandez, et al., "Chimeric Synthetic Peptide as Antigen for Immunodiagnosis of HIV-1 Infection", Biochemical and Biophysical Research Communications, vol. 272, pp. 259-262, 2000.

Jojic et al. "HLA-driven Optimization of an HIV Vaccine Immunogen." 12th Conference on Retroviruses and Infections, Feb. 22-25, 2005. 1 pg.

Regenmortel, "Molecular Design Versus Empirical Discovery in Peptide-Based Vaccines. Coming to Terms with Fuzzy Recognitio Sites and III-Defined Structure-Function Relationship in Immunology", Vaccine, vol. 18, pp. 216-221, 2000.

Shang, et la. "Log-likelihood Adaptive Alogrithm in Single-layer Perception Based Channel Equalisation", Electronics Letters vol. 31, No. 22, pp. 1900-1902, Oct. 1995.

Van der Veen, et la., "Determinating of Binding Amino Acids Based on Random Peptide Array Screening Data " WABI 2001, LNCS, vol. 2149, pp. 264-277, 2001.

Mourik et al., "Determination of interaction potentials of amino acids from native protein structures: Tests of simple lattice models", Journal of Chemical Physics, vol. 110, No. 20, May 22, 1999, pp. 10123-10133.

Protease component

All mutations to be included in protease protein

Split up to separate potential epitopes for vaccine insert

FIG. 14

RT component

All mutations to be included in RT protein

34 M41L E44D   K65R T 69D K70R L74V   A98G K103N V118I   Q151M   Y181C M184V G190A L210W T215Y or T215F K219Q 226

34 M41L 48   177 M184V 191   37 E44D 51   91 A98G K103N V118I 125   174 Y181C G190A L210W T215F K219Q 226
58 K65R K70R 77   208 T215Y 222   62 T69D L74V 81   144 Q151M 158

Split up to separate potential epitopes in vaccine insert

FIG. 15

SEQUENCE LISTING

```
<160> NUMBER OF SEQ ID NOS: 189

<210> SEQ ID NO 1
<211> LENGTH: 9
<212> TYPE: PRT
<213> ORGANISM: Human Immunodeficiency Virus

<400> SEQUENCE: 1

Ala Asn Asn Ala Asp Cys Ala Trp Leu
1               5

<210> SEQ ID NO 2
<211> LENGTH: 9
<212> TYPE: PRT
<213> ORGANISM: Human Immunodeficiency Virus

<400> SEQUENCE: 2

Asn Asn Asn Glu Thr Glu Thr Phe Arg
1               5
```

```
<210> SEQ ID NO 3
<211> LENGTH: 9
<212> TYPE: PRT
<213> ORGANISM: Human Immunodeficiency Virus

<400> SEQUENCE: 3

Ser Lys Lys Ala Lys Gly Trp Phe Tyr
1               5

<210> SEQ ID NO 4
<211> LENGTH: 9
<212> TYPE: PRT
<213> ORGANISM: Human Immunodeficiency Virus

<400> SEQUENCE: 4

Ile Ser Pro Arg Thr Leu Asn Ala Trp
1               5

<210> SEQ ID NO 5
<211> LENGTH: 9
<212> TYPE: PRT
<213> ORGANISM: Human Immunodeficiency Virus

<400> SEQUENCE: 5

Ala Ala Val Lys Ala Ala Cys Trp Trp
1               5

<210> SEQ ID NO 6
<211> LENGTH: 9
<212> TYPE: PRT
<213> ORGANISM: Human Immunodeficiency Virus

<400> SEQUENCE: 6

Pro Ile Ala Pro Gly Gln Met Arg Glu
1               5

<210> SEQ ID NO 7
<211> LENGTH: 9
<212> TYPE: PRT
<213> ORGANISM: Human Immunodeficiency Virus

<400> SEQUENCE: 7

Asn Ser Ser Gln Val Ser Gln Asn Tyr
1               5

<210> SEQ ID NO 8
<211> LENGTH: 9
<212> TYPE: PRT
<213> ORGANISM: Human Immunodeficiency Virus

<400> SEQUENCE: 8

Arg Asp Trp His Leu Gly His Gly Val
1               5

<210> SEQ ID NO 9
<211> LENGTH: 9
<212> TYPE: PRT
<213> ORGANISM: Human Immunodeficiency Virus

<400> SEQUENCE: 9

Pro Ile Trp Lys Gly Pro Ala Lys Leu
1               5
```

```
<210> SEQ ID NO 10
<211> LENGTH: 9
<212> TYPE: PRT
<213> ORGANISM: Human Immunodeficiency Virus

<400> SEQUENCE: 10

Leu Val Trp Arg Trp Gly Thr Met Leu
1               5

<210> SEQ ID NO 11
<211> LENGTH: 9
<212> TYPE: PRT
<213> ORGANISM: Human Immunodeficiency Virus

<400> SEQUENCE: 11

Gly Pro Ser His Lys Ala Arg Val Leu
1               5

<210> SEQ ID NO 12
<211> LENGTH: 9
<212> TYPE: PRT
<213> ORGANISM: Human Immunodeficiency Virus

<400> SEQUENCE: 12

Tyr Leu Ser Trp Val Pro Ala His Lys
1               5

<210> SEQ ID NO 13
<211> LENGTH: 9
<212> TYPE: PRT
<213> ORGANISM: Human Immunodeficiency Virus

<400> SEQUENCE: 13

Lys Gln Gly Gln Asp Gln Trp Thr Tyr
1               5

<210> SEQ ID NO 14
<211> LENGTH: 9
<212> TYPE: PRT
<213> ORGANISM: Human Immunodeficiency Virus

<400> SEQUENCE: 14

His Ile Val Ser Pro Arg Cys Asp Tyr
1               5

<210> SEQ ID NO 15
<211> LENGTH: 9
<212> TYPE: PRT
<213> ORGANISM: Human Immunodeficiency Virus

<400> SEQUENCE: 15

Val Asp Pro Asp Leu Ala Asp Gln Leu
1               5

<210> SEQ ID NO 16
<211> LENGTH: 9
<212> TYPE: PRT
<213> ORGANISM: Human Immunodeficiency Virus

<400> SEQUENCE: 16

Asp Ala Arg Leu Val Ile Thr Thr Tyr
1               5
```

```
<210> SEQ ID NO 17
<211> LENGTH: 9
<212> TYPE: PRT
<213> ORGANISM: Human Immunodeficiency Virus

<400> SEQUENCE: 17

Asp Ala Arg Leu Val Ile Thr Thr Tyr
1               5

<210> SEQ ID NO 18
<211> LENGTH: 9
<212> TYPE: PRT
<213> ORGANISM: Human Immunodeficiency Virus

<400> SEQUENCE: 18

Lys Gln Gly Gln Gly Gln Trp Thr Tyr
1               5

<210> SEQ ID NO 19
<211> LENGTH: 9
<212> TYPE: PRT
<213> ORGANISM: Human Immunodeficiency Virus

<400> SEQUENCE: 19

His Ile Val Ser Pro Arg Cys Glu Tyr
1               5

<210> SEQ ID NO 20
<211> LENGTH: 9
<212> TYPE: PRT
<213> ORGANISM: Human Immunodeficiency Virus

<400> SEQUENCE: 20

Pro Ala Ile Phe Gln Ser Ser Met Thr
1               5

<210> SEQ ID NO 21
<211> LENGTH: 9
<212> TYPE: PRT
<213> ORGANISM: Human Immunodeficiency Virus

<400> SEQUENCE: 21

Arg Pro Gly Asn Phe Leu Gln Ser Arg
1               5

<210> SEQ ID NO 22
<211> LENGTH: 9
<212> TYPE: PRT
<213> ORGANISM: Human Immunodeficiency Virus

<400> SEQUENCE: 22

Val Asp Pro Gly Leu Ala Asp Gln Leu
1               5

<210> SEQ ID NO 23
<211> LENGTH: 9
<212> TYPE: PRT
<213> ORGANISM: Human Immunodeficiency Virus

<400> SEQUENCE: 23

Tyr Asn Glu Trp Thr Leu Glu Leu Leu
1               5
```

```
<210> SEQ ID NO 24
<211> LENGTH: 9
<212> TYPE: PRT
<213> ORGANISM: Human Immunodeficiency Virus

<400> SEQUENCE: 24

Thr Leu Lys Gln Ile Val Lys Lys Leu
1               5

<210> SEQ ID NO 25
<211> LENGTH: 9
<212> TYPE: PRT
<213> ORGANISM: Human Immunodeficiency Virus

<400> SEQUENCE: 25

Gly Asp Gln Glu Glu Leu Ser Ala Leu
1               5

<210> SEQ ID NO 26
<211> LENGTH: 9
<212> TYPE: PRT
<213> ORGANISM: Human Immunodeficiency Virus

<400> SEQUENCE: 26

Glu Gln Glu Leu Leu Glu Leu Asp Lys
1               5

<210> SEQ ID NO 27
<211> LENGTH: 9
<212> TYPE: PRT
<213> ORGANISM: Human Immunodeficiency Virus

<400> SEQUENCE: 27

Ala Leu Gln Asp Ser Gly Ser Glu Val
1               5

<210> SEQ ID NO 28
<211> LENGTH: 9
<212> TYPE: PRT
<213> ORGANISM: Human Immunodeficiency Virus

<400> SEQUENCE: 28

Lys Ser Lys Lys Lys Ala Gln Gln Ala
1               5

<210> SEQ ID NO 29
<211> LENGTH: 9
<212> TYPE: PRT
<213> ORGANISM: Human Immunodeficiency Virus

<400> SEQUENCE: 29

Ser Glu Asn Phe Thr Asp Asn Ala Lys
1               5

<210> SEQ ID NO 30
<211> LENGTH: 9
<212> TYPE: PRT
<213> ORGANISM: Human Immunodeficiency Virus

<400> SEQUENCE: 30

Asn Ala Lys Thr Ile Ile Val Gln Leu
1               5
```

-continued

```
<210> SEQ ID NO 31
<211> LENGTH: 9
<212> TYPE: PRT
<213> ORGANISM: Human Immunodeficiency Virus

<400> SEQUENCE: 31

Tyr Lys Val Val Arg Ile Glu Pro Leu
1               5

<210> SEQ ID NO 32
<211> LENGTH: 9
<212> TYPE: PRT
<213> ORGANISM: Human Immunodeficiency Virus

<400> SEQUENCE: 32

Ile Val Asn Arg Val Arg Gln Gly Tyr
1               5

<210> SEQ ID NO 33
<211> LENGTH: 9
<212> TYPE: PRT
<213> ORGANISM: Human Immunodeficiency Virus

<400> SEQUENCE: 33

Pro Gly Pro Gly Ile Arg Tyr Pro Leu
1               5

<210> SEQ ID NO 34
<211> LENGTH: 9
<212> TYPE: PRT
<213> ORGANISM: Human Immunodeficiency Virus

<400> SEQUENCE: 34

Leu Met Trp Lys Phe Asp Ser Arg Leu
1               5

<210> SEQ ID NO 35
<211> LENGTH: 9
<212> TYPE: PRT
<213> ORGANISM: Human Immunodeficiency Virus

<400> SEQUENCE: 35

Asp Met Asn Leu Pro Gly Arg Trp Lys
1               5

<210> SEQ ID NO 36
<211> LENGTH: 9
<212> TYPE: PRT
<213> ORGANISM: Human Immunodeficiency Virus

<400> SEQUENCE: 36

Pro Leu Asp Glu Asp Phe Arg Lys Tyr
1               5

<210> SEQ ID NO 37
<211> LENGTH: 9
<212> TYPE: PRT
<213> ORGANISM: Human Immunodeficiency Virus

<400> SEQUENCE: 37

Lys Gln Leu Thr Glu Val Val Gln Lys
1               5
```

```
<210> SEQ ID NO 38
<211> LENGTH: 9
<212> TYPE: PRT
<213> ORGANISM: Human Immunodeficiency Virus

<400> SEQUENCE: 38

Ile Ala Thr Glu Ser Ile Val Ile Trp
1               5

<210> SEQ ID NO 39
<211> LENGTH: 9
<212> TYPE: PRT
<213> ORGANISM: Human Immunodeficiency Virus

<400> SEQUENCE: 39

Glu Thr Ala Tyr Phe Ile Leu Lys Leu
1               5

<210> SEQ ID NO 40
<211> LENGTH: 9
<212> TYPE: PRT
<213> ORGANISM: Human Immunodeficiency Virus

<400> SEQUENCE: 40

Gln Val Cys Phe Ile Lys Lys Gly Leu
1               5

<210> SEQ ID NO 41
<211> LENGTH: 9
<212> TYPE: PRT
<213> ORGANISM: Human Immunodeficiency Virus

<400> SEQUENCE: 41

Asp Ser Gln Thr His Gln Val Ser Leu
1               5

<210> SEQ ID NO 42
<211> LENGTH: 9
<212> TYPE: PRT
<213> ORGANISM: Human Immunodeficiency Virus

<400> SEQUENCE: 42

Phe Pro Arg Pro Trp Leu His Gly Leu
1               5

<210> SEQ ID NO 43
<211> LENGTH: 9
<212> TYPE: PRT
<213> ORGANISM: Human Immunodeficiency Virus

<400> SEQUENCE: 43

Val Trp Thr Ile Val Phe Ile Glu Tyr
1               5

<210> SEQ ID NO 44
<211> LENGTH: 9
<212> TYPE: PRT
<213> ORGANISM: Human Immunodeficiency Virus

<400> SEQUENCE: 44

Gln Thr His Gln Val Ser Leu Ser Lys
1               5
```

```
<210> SEQ ID NO 45
<211> LENGTH: 9
<212> TYPE: PRT
<213> ORGANISM: Human Immunodeficiency Virus

<400> SEQUENCE: 45

Thr Trp Glu Thr Trp Trp Thr Glu Tyr
1               5

<210> SEQ ID NO 46
<211> LENGTH: 9
<212> TYPE: PRT
<213> ORGANISM: Human Immunodeficiency Virus

<400> SEQUENCE: 46

Asn Cys Leu Leu His Pro Met Ser Leu
1               5

<210> SEQ ID NO 47
<211> LENGTH: 9
<212> TYPE: PRT
<213> ORGANISM: Human Immunodeficiency Virus

<400> SEQUENCE: 47

Pro Ala Val Arg Glu Arg Met Arg Arg
1               5

<210> SEQ ID NO 48
<211> LENGTH: 9
<212> TYPE: PRT
<213> ORGANISM: Human Immunodeficiency Virus

<400> SEQUENCE: 48

Val Gln Lys Glu Tyr Ala Leu Phe Tyr
1               5

<210> SEQ ID NO 49
<211> LENGTH: 9
<212> TYPE: PRT
<213> ORGANISM: Human Immunodeficiency Virus

<400> SEQUENCE: 49

Ala Leu Ala Ala Leu Ile Thr Pro Lys
1               5

<210> SEQ ID NO 50
<211> LENGTH: 9
<212> TYPE: PRT
<213> ORGANISM: Human Immunodeficiency Virus

<400> SEQUENCE: 50

Pro Lys Thr Ala Cys Thr Asn Cys Tyr
1               5

<210> SEQ ID NO 51
<211> LENGTH: 9
<212> TYPE: PRT
<213> ORGANISM: Human Immunodeficiency Virus

<400> SEQUENCE: 51

Gln Asp Ile Leu Asp Leu Trp Val Tyr
1               5
```

```
<210> SEQ ID NO 52
<211> LENGTH: 9
<212> TYPE: PRT
<213> ORGANISM: Human Immunodeficiency Virus

<400> SEQUENCE: 52

Ser Leu Tyr Asn Thr Val Ala Thr Leu
1               5

<210> SEQ ID NO 53
<211> LENGTH: 9
<212> TYPE: PRT
<213> ORGANISM: Human Immunodeficiency Virus

<400> SEQUENCE: 53

Thr Ala Val Pro Trp Asn Ala Ser Trp
1               5

<210> SEQ ID NO 54
<211> LENGTH: 9
<212> TYPE: PRT
<213> ORGANISM: Human Immunodeficiency Virus

<400> SEQUENCE: 54

Thr Val Arg Leu Ile Lys Phe Leu Tyr
1               5

<210> SEQ ID NO 55
<211> LENGTH: 9
<212> TYPE: PRT
<213> ORGANISM: Human Immunodeficiency Virus

<400> SEQUENCE: 55

Tyr Ala Gly Ile Lys Val Lys Gln Leu
1               5

<210> SEQ ID NO 56
<211> LENGTH: 9
<212> TYPE: PRT
<213> ORGANISM: Human Immunodeficiency Virus

<400> SEQUENCE: 56

Phe Arg Asn Gln Arg Lys Thr Val Lys
1               5

<210> SEQ ID NO 57
<211> LENGTH: 9
<212> TYPE: PRT
<213> ORGANISM: Human Immunodeficiency Virus

<400> SEQUENCE: 57

Glu Arg Phe Ala Val Asn Pro Gly Leu
1               5

<210> SEQ ID NO 58
<211> LENGTH: 9
<212> TYPE: PRT
<213> ORGANISM: Human Immunodeficiency Virus

<400> SEQUENCE: 58

Ala Ile Ile Arg Ile Leu Gln Gln Leu
1               5
```

```
<210> SEQ ID NO 59
<211> LENGTH: 9
<212> TYPE: PRT
<213> ORGANISM: Human Immunodeficiency Virus

<400> SEQUENCE: 59

Glu Leu Lys Asn Ser Ala Val Ser Leu
1               5

<210> SEQ ID NO 60
<211> LENGTH: 9
<212> TYPE: PRT
<213> ORGANISM: Human Immunodeficiency Virus

<400> SEQUENCE: 60

Pro Ile Asp Asn Asp Asn Thr Ser Tyr
1               5

<210> SEQ ID NO 61
<211> LENGTH: 9
<212> TYPE: PRT
<213> ORGANISM: Human Immunodeficiency Virus

<400> SEQUENCE: 61

Arg Ala Met Ala Ser Asp Phe Asn Leu
1               5

<210> SEQ ID NO 62
<211> LENGTH: 9
<212> TYPE: PRT
<213> ORGANISM: Human Immunodeficiency Virus

<400> SEQUENCE: 62

Ser Thr Leu Gln Glu Gln Ile Gly Trp
1               5

<210> SEQ ID NO 63
<211> LENGTH: 9
<212> TYPE: PRT
<213> ORGANISM: Human Immunodeficiency Virus

<400> SEQUENCE: 63

Arg Trp Asn Lys Pro Gln Lys Thr Lys
1               5

<210> SEQ ID NO 64
<211> LENGTH: 9
<212> TYPE: PRT
<213> ORGANISM: Human Immunodeficiency Virus

<400> SEQUENCE: 64

Leu Thr Val Gln Ala Arg Gln Leu Leu
1               5

<210> SEQ ID NO 65
<211> LENGTH: 9
<212> TYPE: PRT
<213> ORGANISM: Human Immunodeficiency Virus

<400> SEQUENCE: 65

Thr Val Lys Cys Phe Asn Cys Gly Lys
1               5
```

```
<210> SEQ ID NO 66
<211> LENGTH: 9
<212> TYPE: PRT
<213> ORGANISM: Human Immunodeficiency Virus

<400> SEQUENCE: 66

Arg Ser Val Val Gly Trp Pro Ala Val
1               5

<210> SEQ ID NO 67
<211> LENGTH: 9
<212> TYPE: PRT
<213> ORGANISM: Human Immunodeficiency Virus

<400> SEQUENCE: 67

Ala Val Gly Ile Gly Ala Met Phe Leu
1               5

<210> SEQ ID NO 68
<211> LENGTH: 9
<212> TYPE: PRT
<213> ORGANISM: Human Immunodeficiency Virus

<400> SEQUENCE: 68

Ala Phe His His Met Ala Arg Glu Leu
1               5

<210> SEQ ID NO 69
<211> LENGTH: 9
<212> TYPE: PRT
<213> ORGANISM: Human Immunodeficiency Virus

<400> SEQUENCE: 69

Arg Gly Arg Gln Lys Val Val Ser Leu
1               5

<210> SEQ ID NO 70
<211> LENGTH: 9
<212> TYPE: PRT
<213> ORGANISM: Human Immunodeficiency Virus

<400> SEQUENCE: 70

Cys Ser Ser Asn Ile Thr Gly Leu Leu
1               5

<210> SEQ ID NO 71
<211> LENGTH: 9
<212> TYPE: PRT
<213> ORGANISM: Human Immunodeficiency Virus

<400> SEQUENCE: 71

Val Pro Leu Thr Glu Glu Ala Glu Leu
1               5

<210> SEQ ID NO 72
<211> LENGTH: 9
<212> TYPE: PRT
<213> ORGANISM: Human Immunodeficiency Virus

<400> SEQUENCE: 72

Lys Leu Ala Gly Arg Trp Pro Val Lys
1               5
```

```
<210> SEQ ID NO 73
<211> LENGTH: 9
<212> TYPE: PRT
<213> ORGANISM: Human Immunodeficiency Virus

<400> SEQUENCE: 73

Ala Leu Phe Tyr Lys Leu Asp Val Val
1               5

<210> SEQ ID NO 74
<211> LENGTH: 9
<212> TYPE: PRT
<213> ORGANISM: Human Immunodeficiency Virus

<400> SEQUENCE: 74

Ala Thr Asn Ala Asp Cys Ala Trp Leu
1               5

<210> SEQ ID NO 75
<211> LENGTH: 9
<212> TYPE: PRT
<213> ORGANISM: Human Immunodeficiency Virus

<400> SEQUENCE: 75

Thr Asn Asn Glu Thr Glu Thr Phe Arg
1               5

<210> SEQ ID NO 76
<211> LENGTH: 9
<212> TYPE: PRT
<213> ORGANISM: Human Immunodeficiency Virus

<400> SEQUENCE: 76

Ser Arg Lys Ala Lys Gly Trp Phe Tyr
1               5

<210> SEQ ID NO 77
<211> LENGTH: 9
<212> TYPE: PRT
<213> ORGANISM: Human Immunodeficiency Virus

<400> SEQUENCE: 77

Ile Ser Pro Arg Thr Leu Asn Ala Leu
1               5

<210> SEQ ID NO 78
<211> LENGTH: 9
<212> TYPE: PRT
<213> ORGANISM: Human Immunodeficiency Virus

<400> SEQUENCE: 78

Thr Ala Val Lys Ala Ala Cys Trp Trp
1               5

<210> SEQ ID NO 79
<211> LENGTH: 9
<212> TYPE: PRT
<213> ORGANISM: Human Immunodeficiency Virus

<400> SEQUENCE: 79

Pro Ile Pro Pro Gly Gln Met Arg Glu
1               5
```

<210> SEQ ID NO 80
<211> LENGTH: 9
<212> TYPE: PRT
<213> ORGANISM: Human Immunodeficiency Virus

<400> SEQUENCE: 80

Ser Ser Ser Gln Val Ser Gln Asn Tyr
1 5

<210> SEQ ID NO 81
<211> LENGTH: 9
<212> TYPE: PRT
<213> ORGANISM: Human Immunodeficiency Virus

<400> SEQUENCE: 81

Arg Asp Trp His Leu Gly Gln Gly Val
1 5

<210> SEQ ID NO 82
<211> LENGTH: 9
<212> TYPE: PRT
<213> ORGANISM: Human Immunodeficiency Virus

<400> SEQUENCE: 82

Pro Leu Trp Lys Gly Pro Ala Lys Leu
1 5

<210> SEQ ID NO 83
<211> LENGTH: 9
<212> TYPE: PRT
<213> ORGANISM: Human Immunodeficiency Virus

<400> SEQUENCE: 83

Trp Val Trp Arg Trp Gly Thr Met Leu
1 5

<210> SEQ ID NO 84
<211> LENGTH: 9
<212> TYPE: PRT
<213> ORGANISM: Human Immunodeficiency Virus

<400> SEQUENCE: 84

Gly Pro Gly His Lys Ala Arg Val Leu
1 5

<210> SEQ ID NO 85
<211> LENGTH: 9
<212> TYPE: PRT
<213> ORGANISM: Human Immunodeficiency Virus

<400> SEQUENCE: 85

Tyr Leu Ala Trp Val Pro Ala His Lys
1 5

<210> SEQ ID NO 86
<211> LENGTH: 9
<212> TYPE: PRT
<213> ORGANISM: Human Immunodeficiency Virus

<400> SEQUENCE: 86

Lys Gln Gly Gln Gly Gln Trp Thr Tyr
1 5

```
<210> SEQ ID NO 87
<211> LENGTH: 9
<212> TYPE: PRT
<213> ORGANISM: Human Immunodeficiency Virus

<400> SEQUENCE: 87

His Ile Val Ser Pro Arg Cys Glu Tyr
1               5

<210> SEQ ID NO 88
<211> LENGTH: 9
<212> TYPE: PRT
<213> ORGANISM: Human Immunodeficiency Virus

<400> SEQUENCE: 88

Val Asp Pro Asp Leu Ala Asp Arg Leu
1               5

<210> SEQ ID NO 89
<211> LENGTH: 9
<212> TYPE: PRT
<213> ORGANISM: Human Immunodeficiency Virus

<400> SEQUENCE: 89

Asp Ala Lys Leu Val Ile Thr Thr Tyr
1               5

<210> SEQ ID NO 90
<211> LENGTH: 9
<212> TYPE: PRT
<213> ORGANISM: Human Immunodeficiency Virus

<400> SEQUENCE: 90

Lys Gln Gly Leu Gly Gln Trp Thr Tyr
1               5

<210> SEQ ID NO 91
<211> LENGTH: 9
<212> TYPE: PRT
<213> ORGANISM: Human Immunodeficiency Virus

<400> SEQUENCE: 91

His Ile Val Ser Pro Ser Cys Glu Tyr
1               5

<210> SEQ ID NO 92
<211> LENGTH: 9
<212> TYPE: PRT
<213> ORGANISM: Human Immunodeficiency Virus

<400> SEQUENCE: 92

Pro Ala Ile Phe Gln Cys Ser Met Thr
1               5

<210> SEQ ID NO 93
<211> LENGTH: 9
<212> TYPE: PRT
<213> ORGANISM: Human Immunodeficiency Virus

<400> SEQUENCE: 93

Arg Pro Gly Asn Phe Pro Gln Ser Arg
1               5
```

```
<210> SEQ ID NO 94
<211> LENGTH: 9
<212> TYPE: PRT
<213> ORGANISM: Human Immunodeficiency Virus

<400> SEQUENCE: 94

Val Asp Pro Asp Leu Ala Asp Gln Leu
1               5

<210> SEQ ID NO 95
<211> LENGTH: 9
<212> TYPE: PRT
<213> ORGANISM: Human Immunodeficiency Virus

<400> SEQUENCE: 95

Tyr Asn Gln Trp Thr Leu Glu Leu Leu
1               5

<210> SEQ ID NO 96
<211> LENGTH: 9
<212> TYPE: PRT
<213> ORGANISM: Human Immunodeficiency Virus

<400> SEQUENCE: 96

Met Leu Lys Gln Ile Val Lys Lys Leu
1               5

<210> SEQ ID NO 97
<211> LENGTH: 9
<212> TYPE: PRT
<213> ORGANISM: Human Immunodeficiency Virus

<400> SEQUENCE: 97

Gly Asp Gln Glu Glu Leu Ala Ala Leu
1               5

<210> SEQ ID NO 98
<211> LENGTH: 9
<212> TYPE: PRT
<213> ORGANISM: Human Immunodeficiency Virus

<400> SEQUENCE: 98

Glu Gln Glu Leu Leu Ala Leu Asp Lys
1               5

<210> SEQ ID NO 99
<211> LENGTH: 9
<212> TYPE: PRT
<213> ORGANISM: Human Immunodeficiency Virus

<400> SEQUENCE: 99

Ala Leu Gln Asp Ser Gly Leu Glu Val
1               5

<210> SEQ ID NO 100
<211> LENGTH: 9
<212> TYPE: PRT
<213> ORGANISM: Human Immunodeficiency Virus

<400> SEQUENCE: 100

Lys Cys Lys Lys Lys Ala Gln Gln Ala
1               5
```

```
<210> SEQ ID NO 101
<211> LENGTH: 9
<212> TYPE: PRT
<213> ORGANISM: Human Immunodeficiency Virus

<400> SEQUENCE: 101

Ser Glu Asn Phe Thr Asn Asn Ala Lys
1               5

<210> SEQ ID NO 102
<211> LENGTH: 9
<212> TYPE: PRT
<213> ORGANISM: Human Immunodeficiency Virus

<400> SEQUENCE: 102

Asn Ala Lys Asn Ile Ile Val Gln Leu
1               5

<210> SEQ ID NO 103
<211> LENGTH: 9
<212> TYPE: PRT
<213> ORGANISM: Human Immunodeficiency Virus

<400> SEQUENCE: 103

Tyr Lys Val Val Lys Ile Glu Pro Leu
1               5

<210> SEQ ID NO 104
<211> LENGTH: 9
<212> TYPE: PRT
<213> ORGANISM: Human Immunodeficiency Virus

<400> SEQUENCE: 104

Val Val Asn Arg Val Arg Gln Gly Tyr
1               5

<210> SEQ ID NO 105
<211> LENGTH: 9
<212> TYPE: PRT
<213> ORGANISM: Human Immunodeficiency Virus

<400> SEQUENCE: 105

Asn Ser Ser Lys Val Ser Gln Asn Tyr
1               5

<210> SEQ ID NO 106
<211> LENGTH: 9
<212> TYPE: PRT
<213> ORGANISM: Human Immunodeficiency Virus

<400> SEQUENCE: 106

Leu Ser Pro Arg Thr Leu Asn Ala Trp
1               5

<210> SEQ ID NO 107
<211> LENGTH: 9
<212> TYPE: PRT
<213> ORGANISM: Human Immunodeficiency Virus

<400> SEQUENCE: 107

Pro Gly Pro Gly Ile Arg Phe Pro Leu
1               5
```

<210> SEQ ID NO 108
<211> LENGTH: 9
<212> TYPE: PRT
<213> ORGANISM: Human Immunodeficiency Virus

<400> SEQUENCE: 108

Leu Met Trp Arg Phe Asp Ser Arg Leu
1               5

<210> SEQ ID NO 109
<211> LENGTH: 9
<212> TYPE: PRT
<213> ORGANISM: Human Immunodeficiency Virus

<400> SEQUENCE: 109

Glu Met Asn Leu Pro Gly Arg Trp Lys
1               5

<210> SEQ ID NO 110
<211> LENGTH: 9
<212> TYPE: PRT
<213> ORGANISM: Human Immunodeficiency Virus

<400> SEQUENCE: 110

Pro Leu Asp Lys Asp Phe Arg Lys Tyr
1               5

<210> SEQ ID NO 111
<211> LENGTH: 9
<212> TYPE: PRT
<213> ORGANISM: Human Immunodeficiency Virus

<400> SEQUENCE: 111

Lys Gln Leu Thr Glu Ala Val Gln Lys
1               5

<210> SEQ ID NO 112
<211> LENGTH: 9
<212> TYPE: PRT
<213> ORGANISM: Human Immunodeficiency Virus

<400> SEQUENCE: 112

Val Ala Thr Glu Ser Ile Val Ile Trp
1               5

<210> SEQ ID NO 113
<211> LENGTH: 9
<212> TYPE: PRT
<213> ORGANISM: Human Immunodeficiency Virus

<400> SEQUENCE: 113

Glu Thr Ala Tyr Phe Leu Leu Lys Leu
1               5

<210> SEQ ID NO 114
<211> LENGTH: 9
<212> TYPE: PRT
<213> ORGANISM: Human Immunodeficiency Virus

<400> SEQUENCE: 114

Gln Val Cys Phe Ile Lys Lys Ala Leu
1               5

```
<210> SEQ ID NO 115
<211> LENGTH: 9
<212> TYPE: PRT
<213> ORGANISM: Human Immunodeficiency Virus

<400> SEQUENCE: 115

Asp Ser Gln Thr Asp Gln Val Ser Leu
1               5

<210> SEQ ID NO 116
<211> LENGTH: 9
<212> TYPE: PRT
<213> ORGANISM: Human Immunodeficiency Virus

<400> SEQUENCE: 116

Ser Lys Lys Ala Arg Gly Trp Phe Tyr
1               5

<210> SEQ ID NO 117
<211> LENGTH: 9
<212> TYPE: PRT
<213> ORGANISM: Human Immunodeficiency Virus

<400> SEQUENCE: 117

Phe Pro Arg Pro Trp Leu His Ser Leu
1               5

<210> SEQ ID NO 118
<211> LENGTH: 9
<212> TYPE: PRT
<213> ORGANISM: Human Immunodeficiency Virus

<400> SEQUENCE: 118

Val Trp Thr Ile Val Leu Ile Glu Tyr
1               5

<210> SEQ ID NO 119
<211> LENGTH: 9
<212> TYPE: PRT
<213> ORGANISM: Human Immunodeficiency Virus

<400> SEQUENCE: 119

Lys Gln Leu Ala Glu Val Val Gln Lys
1               5

<210> SEQ ID NO 120
<211> LENGTH: 9
<212> TYPE: PRT
<213> ORGANISM: Human Immunodeficiency Virus

<400> SEQUENCE: 120

Gln Thr Asp Gln Val Ser Leu Ser Lys
1               5

<210> SEQ ID NO 121
<211> LENGTH: 9
<212> TYPE: PRT
<213> ORGANISM: Human Immunodeficiency Virus

<400> SEQUENCE: 121

Thr Trp Glu Ala Trp Trp Thr Glu Tyr
1               5
```

```
<210> SEQ ID NO 122
<211> LENGTH: 9
<212> TYPE: PRT
<213> ORGANISM: Human Immunodeficiency Virus

<400> SEQUENCE: 122

Tyr His Glu Trp Thr Leu Glu Leu Leu
1               5

<210> SEQ ID NO 123
<211> LENGTH: 9
<212> TYPE: PRT
<213> ORGANISM: Human Immunodeficiency Virus

<400> SEQUENCE: 123

Asn Ser Leu Leu His Pro Met Ser Leu
1               5

<210> SEQ ID NO 124
<211> LENGTH: 9
<212> TYPE: PRT
<213> ORGANISM: Human Immunodeficiency Virus

<400> SEQUENCE: 124

Pro Thr Val Arg Glu Arg Met Arg Arg
1               5

<210> SEQ ID NO 125
<211> LENGTH: 9
<212> TYPE: PRT
<213> ORGANISM: Human Immunodeficiency Virus

<400> SEQUENCE: 125

Val Lys Lys Glu Tyr Ala Leu Phe Tyr
1               5

<210> SEQ ID NO 126
<211> LENGTH: 9
<212> TYPE: PRT
<213> ORGANISM: Human Immunodeficiency Virus

<400> SEQUENCE: 126

Ala Leu Thr Ala Leu Ile Thr Pro Lys
1               5

<210> SEQ ID NO 127
<211> LENGTH: 9
<212> TYPE: PRT
<213> ORGANISM: Human Immunodeficiency Virus

<400> SEQUENCE: 127

Pro Lys Thr Ala Cys Asn Asn Cys Tyr
1               5

<210> SEQ ID NO 128
<211> LENGTH: 9
<212> TYPE: PRT
<213> ORGANISM: Human Immunodeficiency Virus

<400> SEQUENCE: 128

Gln Glu Ile Leu Asp Leu Trp Val Tyr
1               5
```

<210> SEQ ID NO 129
<211> LENGTH: 9
<212> TYPE: PRT
<213> ORGANISM: Human Immunodeficiency Virus

<400> SEQUENCE: 129

Asp Ser Gln Ala His Gln Val Ser Leu
1               5

<210> SEQ ID NO 130
<211> LENGTH: 9
<212> TYPE: PRT
<213> ORGANISM: Human Immunodeficiency Virus

<400> SEQUENCE: 130

Ser Leu Tyr Asn Thr Val Ala Val Leu
1               5

<210> SEQ ID NO 131
<211> LENGTH: 9
<212> TYPE: PRT
<213> ORGANISM: Human Immunodeficiency Virus

<400> SEQUENCE: 131

Thr Thr Val Pro Trp Asn Ala Ser Trp
1               5

<210> SEQ ID NO 132
<211> LENGTH: 9
<212> TYPE: PRT
<213> ORGANISM: Human Immunodeficiency Virus

<400> SEQUENCE: 132

Ser Leu Phe Asn Thr Val Ala Thr Leu
1               5

<210> SEQ ID NO 133
<211> LENGTH: 9
<212> TYPE: PRT
<213> ORGANISM: Human Immunodeficiency Virus

<400> SEQUENCE: 133

Ala Thr Val Lys Ala Ala Cys Trp Trp
1               5

<210> SEQ ID NO 134
<211> LENGTH: 9
<212> TYPE: PRT
<213> ORGANISM: Human Immunodeficiency Virus

<400> SEQUENCE: 134

Ala Val Arg Leu Ile Lys Phe Leu Tyr
1               5

<210> SEQ ID NO 135
<211> LENGTH: 9
<212> TYPE: PRT
<213> ORGANISM: Human Immunodeficiency Virus

<400> SEQUENCE: 135

Tyr Ala Gly Ile Lys Val Arg Gln Leu
1               5

```
<210> SEQ ID NO 136
<211> LENGTH: 9
<212> TYPE: PRT
<213> ORGANISM: Human Immunodeficiency Virus

<400> SEQUENCE: 136

Ile Arg Asn Gln Arg Lys Thr Val Lys
1               5

<210> SEQ ID NO 137
<211> LENGTH: 9
<212> TYPE: PRT
<213> ORGANISM: Human Immunodeficiency Virus

<400> SEQUENCE: 137

Glu Arg Phe Ala Leu Asn Pro Gly Leu
1               5

<210> SEQ ID NO 138
<211> LENGTH: 9
<212> TYPE: PRT
<213> ORGANISM: Human Immunodeficiency Virus

<400> SEQUENCE: 138

Ala Ile Ile Arg Thr Leu Gln Gln Leu
1               5

<210> SEQ ID NO 139
<211> LENGTH: 9
<212> TYPE: PRT
<213> ORGANISM: Human Immunodeficiency Virus

<400> SEQUENCE: 139

Ile Ala Val Pro Trp Asn Ala Ser Trp
1               5

<210> SEQ ID NO 140
<211> LENGTH: 9
<212> TYPE: PRT
<213> ORGANISM: Human Immunodeficiency Virus

<400> SEQUENCE: 140

Leu Val Trp Arg Trp Gly Thr Leu Leu
1               5

<210> SEQ ID NO 141
<211> LENGTH: 9
<212> TYPE: PRT
<213> ORGANISM: Human Immunodeficiency Virus

<400> SEQUENCE: 141

Ser Ala Val Arg Glu Arg Met Arg Arg
1               5

<210> SEQ ID NO 142
<211> LENGTH: 9
<212> TYPE: PRT
<213> ORGANISM: Human Immunodeficiency Virus

<400> SEQUENCE: 142

Glu Leu Lys Asn Ser Ala Ile Ser Leu
1               5
```

```
<210> SEQ ID NO 143
<211> LENGTH: 9
<212> TYPE: PRT
<213> ORGANISM: Human Immunodeficiency Virus

<400> SEQUENCE: 143

Leu Val Trp Arg Trp Gly Ile Met Leu
1               5

<210> SEQ ID NO 144
<211> LENGTH: 9
<212> TYPE: PRT
<213> ORGANISM: Human Immunodeficiency Virus

<400> SEQUENCE: 144

Gln Ile Asp Asn Asp Asn Thr Ser Tyr
1               5

<210> SEQ ID NO 145
<211> LENGTH: 9
<212> TYPE: PRT
<213> ORGANISM: Human Immunodeficiency Virus

<400> SEQUENCE: 145

Arg Ala Met Ala Asn Asp Phe Asn Leu
1               5

<210> SEQ ID NO 146
<211> LENGTH: 9
<212> TYPE: PRT
<213> ORGANISM: Human Immunodeficiency Virus

<400> SEQUENCE: 146

Ser Asn Leu Gln Glu Gln Ile Gly Trp
1               5

<210> SEQ ID NO 147
<211> LENGTH: 9
<212> TYPE: PRT
<213> ORGANISM: Human Immunodeficiency Virus

<400> SEQUENCE: 147

Arg Trp Asn Lys Pro Arg Lys Thr Lys
1               5

<210> SEQ ID NO 148
<211> LENGTH: 9
<212> TYPE: PRT
<213> ORGANISM: Human Immunodeficiency Virus

<400> SEQUENCE: 148

Leu Thr Val Gln Ala Arg Leu Leu Leu
1               5

<210> SEQ ID NO 149
<211> LENGTH: 9
<212> TYPE: PRT
<213> ORGANISM: Human Immunodeficiency Virus

<400> SEQUENCE: 149

Ile Val Lys Cys Phe Asn Cys Gly Lys
1               5
```

```
<210> SEQ ID NO 150
<211> LENGTH: 9
<212> TYPE: PRT
<213> ORGANISM: Human Immunodeficiency Virus

<400> SEQUENCE: 150

Ser Ser Val Val Gly Trp Pro Ala Val
1               5

<210> SEQ ID NO 151
<211> LENGTH: 9
<212> TYPE: PRT
<213> ORGANISM: Human Immunodeficiency Virus

<400> SEQUENCE: 151

Ala Val Gly Ile Gly Ala Val Phe Leu
1               5

<210> SEQ ID NO 152
<211> LENGTH: 9
<212> TYPE: PRT
<213> ORGANISM: Human Immunodeficiency Virus

<400> SEQUENCE: 152

Ala Phe His His Met Ala Arg Glu Lys
1               5

<210> SEQ ID NO 153
<211> LENGTH: 9
<212> TYPE: PRT
<213> ORGANISM: Human Immunodeficiency Virus

<400> SEQUENCE: 153

Phe Pro Arg Ile Trp Leu His Gly Leu
1               5

<210> SEQ ID NO 154
<211> LENGTH: 9
<212> TYPE: PRT
<213> ORGANISM: Human Immunodeficiency Virus

<400> SEQUENCE: 154

Arg Gly Arg Gln Lys Val Val Ser Ile
1               5

<210> SEQ ID NO 155
<211> LENGTH: 9
<212> TYPE: PRT
<213> ORGANISM: Human Immunodeficiency Virus

<400> SEQUENCE: 155

Cys Ser Ser Asn Ile Thr Gly Leu Ile
1               5

<210> SEQ ID NO 156
<211> LENGTH: 9
<212> TYPE: PRT
<213> ORGANISM: Human Immunodeficiency Virus

<400> SEQUENCE: 156

His Asn Glu Trp Thr Leu Glu Leu Leu
1               5
```

```
<210> SEQ ID NO 157
<211> LENGTH: 9
<212> TYPE: PRT
<213> ORGANISM: Human Immunodeficiency Virus

<400> SEQUENCE: 157

Val Thr Leu Thr Glu Glu Ala Glu Leu
1               5

<210> SEQ ID NO 158
<211> LENGTH: 9
<212> TYPE: PRT
<213> ORGANISM: Human Immunodeficiency Virus

<400> SEQUENCE: 158

Lys Leu Ala Gly Arg Trp Pro Val Thr
1               5

<210> SEQ ID NO 159
<211> LENGTH: 9
<212> TYPE: PRT
<213> ORGANISM: Human Immunodeficiency Virus

<400> SEQUENCE: 159

Ala Leu Phe Tyr Lys Leu Asp Val Ile
1               5

<210> SEQ ID NO 160
<211> LENGTH: 50
<212> TYPE: PRT
<213> ORGANISM: Human Immunodeficiency Virus

<400> SEQUENCE: 160

Met Leu Ile Cys Lys Arg Asp Cys Ile Ala Glu Leu Asp Arg Gln Lys
1               5                   10                  15

Lys Met Met Asn Ile His Glu Cys Ile Thr Ala Phe Trp Phe Ser Lys
                20                  25                  30

Asp Pro Val Glu Pro Asp Pro Thr Trp Lys Gly Trp Trp Met Thr Glu
            35                  40                  45

His Gln
    50

<210> SEQ ID NO 161
<211> LENGTH: 41
<212> TYPE: PRT
<213> ORGANISM: Human Immunodeficiency Virus

<400> SEQUENCE: 161

Leu Ile Cys Lys Arg Asp Cys Ile Ala Glu Leu Asp Met Asn Ile His
1               5                   10                  15

Glu Cys Ile Thr Ala Phe Pro Asp Pro Thr Trp Lys Gly Trp Trp Met
                20                  25                  30

Thr Glu His Gln Ala Met Met Gln Trp
            35                  40

<210> SEQ ID NO 162
<211> LENGTH: 41
<212> TYPE: PRT
<213> ORGANISM: Human Immunodeficiency Virus
```

-continued

<400> SEQUENCE: 162

Ala Phe Leu Ser Lys Phe Gly Tyr Tyr Cys Asn Ile His Glu Cys Ile
1               5                   10                  15

Thr Ala Phe Trp Phe Ser Asn Glu Asn Glu Leu Lys Asp Pro Val Glu
                20                  25                  30

Pro Asp Pro Thr Trp Lys Gly Trp Glu
            35                  40

<210> SEQ ID NO 163
<211> LENGTH: 43
<212> TYPE: PRT
<213> ORGANISM: Human Immunodeficiency Virus

<400> SEQUENCE: 163

Cys Lys Arg Asp Cys Ile Ala Glu Leu Asp Arg Gln Lys Ile His Glu
1               5                   10                  15

Cys Ile Thr Ala Phe Trp Phe Val Pro Asp Pro Thr Trp Lys Gly
                20                  25                  30

Trp Trp Met Thr Thr Glu His Gln Trp Met Thr
            35                  40

<210> SEQ ID NO 164
<211> LENGTH: 41
<212> TYPE: PRT
<213> ORGANISM: Human Immunodeficiency Virus

<400> SEQUENCE: 164

Glu Asn Arg Glu Ala Lys Lys Met Met Asn Ile His Glu Cys Ile Thr
1               5                   10                  15

Ala Phe Cys Phe Ser Lys Asp Pro Val Glu Pro Asp Pro Thr Trp Lys
                20                  25                  30

Gly Ser His Gly Trp Trp Met Thr Glu
            35                  40

<210> SEQ ID NO 165
<211> LENGTH: 41
<212> TYPE: PRT
<213> ORGANISM: Human Immunodeficiency Virus

<400> SEQUENCE: 165

Met Val Asn Asn Glu Asp Glu Val Glu Thr Asn Ile Trp Ser Lys Lys
1               5                   10                  15

Met Met Asn Ile His Glu Cys Ile Thr Ala Phe Cys Arg Phe Ser Lys
                20                  25                  30

Asp Pro Val Glu Pro Asp Pro Thr Trp
            35                  40

<210> SEQ ID NO 166
<211> LENGTH: 41
<212> TYPE: PRT
<213> ORGANISM: Human Immunodeficiency Virus

<400> SEQUENCE: 166

Met Thr Met His Asp Cys Ile Ala Glu Leu Asp Arg Gln Lys Lys Met
1               5                   10                  15

Met Ile Asp Arg Cys Ile Thr Ala Phe Trp Phe Ser Lys Asp Pro His
                20                  25                  30

Val Glu Pro Asp Pro Thr Trp Lys Cys
            35                  40

-continued

<210> SEQ ID NO 167
<211> LENGTH: 42
<212> TYPE: PRT
<213> ORGANISM: Human Immunodeficiency Virus

<400> SEQUENCE: 167

Phe Arg Gln Tyr Ser Cys Lys Lys Arg Asp Cys Ile Ala Glu Leu Asp
1               5                   10                  15

Arg Gln Lys Lys Met Met Ala Met Asn Ile His Glu Cys Ile Thr Ala
            20                  25                  30

Phe Trp Phe Ser Lys Asp Phe Ile Leu Ala
        35                  40

<210> SEQ ID NO 168
<211> LENGTH: 42
<212> TYPE: PRT
<213> ORGANISM: Human Immunodeficiency Virus

<400> SEQUENCE: 168

Cys Glu Ile Ala Glu Leu Asp Arg Gln Lys Lys Met Met Asn Gln Trp
1               5                   10                  15

Phe Ser Lys Asp Pro Val Glu Pro Asp Pro Thr Ala Lys Gly Trp Trp
            20                  25                  30

Met Thr Glu His Gln His Gln Gln Thr Ile
        35                  40

<210> SEQ ID NO 169
<211> LENGTH: 42
<212> TYPE: PRT
<213> ORGANISM: Human Immunodeficiency Virus

<400> SEQUENCE: 169

Asn Ile Asn Met Phe Trp Phe Ser Lys Asp Pro Val Glu Pro Asp Pro
1               5                   10                  15

Thr Trp Asp Gln His Gly Pro Leu Met Lys Gly Trp Trp Met Thr Glu
            20                  25                  30

His Gln Thr Thr Glu His Gln Glu His Gln
        35                  40

<210> SEQ ID NO 170
<211> LENGTH: 43
<212> TYPE: PRT
<213> ORGANISM: Human Immunodeficiency Virus

<400> SEQUENCE: 170

Cys Lys Arg Asp Cys Ile Ala Glu Leu Asp Arg Gln Lys Lys Glu Glu
1               5                   10                  15

Val Ile Pro Asn Ile His Glu Cys Ile Thr Ala Phe Trp Phe Ser Lys
            20                  25                  30

Asp Pro Val Val Glu Pro Asp Pro Thr Trp Lys
        35                  40

<210> SEQ ID NO 171
<211> LENGTH: 41
<212> TYPE: PRT
<213> ORGANISM: Human Immunodeficiency Virus

```
<400> SEQUENCE: 171

Gln Lys Lys Met Met Asn Ile His Glu Cys Ile Thr Ala Trp Phe Ser
1               5                   10                  15

Lys Asp Pro Val Glu Pro Asp Pro Thr Trp Cys Trp Trp Met Thr Glu
            20                  25                  30

His Gln Gln Ile Arg Phe Ala Ile Gln
        35                  40

<210> SEQ ID NO 172
<211> LENGTH: 42
<212> TYPE: PRT
<213> ORGANISM: Human Immunodeficiency Virus

<400> SEQUENCE: 172

Lys Arg Asp Cys Ile Ala Glu Leu Asp Arg Gln Lys Lys Met Met Ala
1               5                   10                  15

Phe Trp Phe Ser Lys Asp Pro Val Arg Pro Asp Pro Thr Leu Phe Ile
            20                  25                  30

Trp Lys Gly Trp Trp Met Thr Glu His Gln
        35                  40

<210> SEQ ID NO 173
<211> LENGTH: 73
<212> TYPE: PRT
<213> ORGANISM: Human Immunodeficiency Virus

<400> SEQUENCE: 173

Phe Ala Ile Lys Lys Lys Asp Ser Thr Lys Trp Arg Lys Leu Val Asp
1               5                   10                  15

Phe Arg Glu Leu Asn Lys Arg Thr Gln Asp Phe Trp Glu Val Gln Leu
            20                  25                  30

Gly Ile Pro His Pro Ala Gly Leu Lys Lys Ser Val Thr Val Leu
        35                  40              45

Asp Val Gly Asp Ala Tyr Phe Ser Val Pro Leu Asp Lys Asp Phe Arg
    50                  55                  60

Lys Tyr Thr Ala Phe Thr Ile Pro Ser
65                  70

<210> SEQ ID NO 174
<211> LENGTH: 88
<212> TYPE: PRT
<213> ORGANISM: Human Immunodeficiency Virus

<400> SEQUENCE: 174

Asn Asn Glu Thr Pro Gly Ile Arg Tyr Gln Tyr Asn Val Leu Pro Gln
1               5                   10                  15

Gly Trp Lys Gly Ser Pro Ala Ile Phe Gln Ser Ser Met Thr Lys Ile
            20                  25                  30

Leu Glu Pro Phe Arg Lys Gln Asn Pro Asp Ile Val Ile Tyr Gln Tyr
        35                  40                  45

Met Asp Asp Leu Tyr Val Gly Ser Asp Leu Glu Ile Gly Gln His Arg
    50                  55                  60

Thr Lys Ile Glu Glu Leu Arg Gln His Leu Leu Arg Trp Gly Phe Thr
65                  70                  75                  80

Thr Pro Asp Lys Lys His Gln Lys
                85
```

-continued

```
<210> SEQ ID NO 175
<211> LENGTH: 5
<212> TYPE: PRT
<213> ORGANISM: Human Immunodeficiency Virus

<400> SEQUENCE: 175

Gln Gln Glu Lys Ser
1               5

<210> SEQ ID NO 176
<211> LENGTH: 50
<212> TYPE: PRT
<213> ORGANISM: Human Immunodeficiency Virus

<400> SEQUENCE: 176

Met Leu Ile Cys Lys Arg Asp Cys Ile Ala Glu Leu Asp Arg Gln Lys
1               5                   10                  15

Lys Met Met Asn Ile His Lys Cys Ile Thr Ala Phe Trp Phe Ser Lys
            20                  25                  30

Asp Pro Val Glu Pro Asp Pro Thr Trp Lys Gly Trp Trp Met Thr Glu
        35                  40                  45

His Gln
    50

<210> SEQ ID NO 177
<211> LENGTH: 40
<212> TYPE: PRT
<213> ORGANISM: Human Immunodeficiency Virus

<400> SEQUENCE: 177

Leu Ile Cys Lys Arg Asp Cys Ile Ala Glu Leu Asp Met Asn Ile His
1               5                   10                  15

Glu Cys Ile Thr Ala Phe Pro Asp Pro Thr Trp Lys Trp Trp Met Thr
            20                  25                  30

Glu His Gln Ala Asn Met Gln Trp
        35                  40

<210> SEQ ID NO 178
<211> LENGTH: 41
<212> TYPE: PRT
<213> ORGANISM: Human Immunodeficiency Virus

<400> SEQUENCE: 178

Ala Phe Leu Ser Lys Phe Gly Tyr Tyr Cys Asn Ile His Glu Cys Ile
1               5                   10                  15

Thr Ala Phe Trp Phe Ser Asn Glu Asn Glu Leu Lys Asp Pro Val Glu
            20                  25                  30

Pro Asp Pro Thr Trp Lys Gly Trp Glu
        35                  40

<210> SEQ ID NO 179
<211> LENGTH: 43
<212> TYPE: PRT
<213> ORGANISM: Human Immunodeficiency Virus

<400> SEQUENCE: 179

Cys Lys Arg Asp Cys Ile Ala Glu Leu Asp Arg Gln Lys Ile His Glu
1               5                   10                  15

Cys Ile Thr Ala Phe Trp Phe Val Glu Pro Asp Pro Thr Trp Lys Gly
            20                  25                  30

Trp Trp Met Thr Thr Glu His Gln Trp Met Thr
        35                  40
```

<210> SEQ ID NO 180
<211> LENGTH: 41
<212> TYPE: PRT
<213> ORGANISM: Human Immunodeficiency Virus

<400> SEQUENCE: 180

Glu Asn Arg Glu Ala Lys Lys Asn Asn Ile His Glu Cys Ile Thr
1               5                   10                  15

Ala Phe Cys Phe Ser Lys Asp Pro Val Glu Pro Asp Pro Thr Trp Lys
                20                  25                  30

Gly Ser His Gly Trp Trp Asn Thr Glu
            35                  40

<210> SEQ ID NO 181
<211> LENGTH: 41
<212> TYPE: PRT
<213> ORGANISM: Human Immunodeficiency Virus

<400> SEQUENCE: 181

Met Val Asn Asn Glu Asp Glu Val Glu Thr Asn Ile Trp Ser Lys Lys
1               5                   10                  15

Met Met Asn Ile His Glu Cys Ile Thr Ala Phe Cys Arg Phe Ser Lys
                20                  25                  30

Asp Pro Val Glu Pro Asp Pro Thr Trp
            35                  40

<210> SEQ ID NO 182
<211> LENGTH: 41
<212> TYPE: PRT
<213> ORGANISM: Human Immunodeficiency Virus

<400> SEQUENCE: 182

Met Thr Met His Asp Cys Ile Ala Glu Leu Asp Arg Gln Lys Lys Met
1               5                   10                  15

Met Ile Asp Arg Cys Ile Thr Ala Phe Trp Phe Ser Lys Asp Pro His
                20                  25                  30

Val Glu Pro Asp Pro Thr Trp Lys Gly
            35                  40

<210> SEQ ID NO 183
<211> LENGTH: 42
<212> TYPE: PRT
<213> ORGANISM: Human Immunodeficiency Virus

<400> SEQUENCE: 183

Phe Arg Gln Tyr Ser Cys Lys Lys Arg Asp Cys Ile Ala Glu Leu Asp
1               5                   10                  15

Arg Gln Lys Lys Met Met Ala Met Asn Ile His Lys Cys Ile Thr Ala
                20                  25                  30

Phe Trp Phe Ser Lys Asp Phe Ile Leu Ala
            35                  40

<210> SEQ ID NO 184
<211> LENGTH: 42
<212> TYPE: PRT
<213> ORGANISM: Human Immunodeficiency Virus -continued

```
<400> SEQUENCE: 184

Cys Glu Ile Ala Glu Leu Asp Arg Gln Lys Lys Met Met Asn Gln Trp
1               5                   10                  15

Phe Ser Lys Asp Pro Val Glu Pro Asp Pro Thr Ala Lys Gly Trp Trp
                20                  25                  30

Met Thr Glu His Gln His Gln Gln Thr Ile
                35                  40

<210> SEQ ID NO 185
<211> LENGTH: 42
<212> TYPE: PRT
<213> ORGANISM: Human Immunodeficiency Virus

<400> SEQUENCE: 185

Asn Ile Asn Met Phe Trp Phe Ser Lys Asp Pro Val Glu Pro Asp Pro
1               5                   10                  15

Thr Trp Asp Gln His Gly Pro Leu Met Lys Gly Trp Trp Met Thr Glu
                20                  25                  30

His Gln Thr Thr Glu His Gln Glu His Gln
                35                  40

<210> SEQ ID NO 186
<211> LENGTH: 43
<212> TYPE: PRT
<213> ORGANISM: Human Immunodeficiency Virus

<400> SEQUENCE: 186

Cys Lys Arg Asp Cys Ile Ala Glu Leu Asp Arg Gln Lys Lys Glu Glu
1               5                   10                  15

Val Ile Pro Asn Ile His Glu Cys Ile Thr Ala Phe Trp Pro Ser Lys
                20                  25                  30

Asp Pro Val Val Glu Pro Asp Pro Thr Trp Lys
                35                  40

<210> SEQ ID NO 187
<211> LENGTH: 41
<212> TYPE: PRT
<213> ORGANISM: Human Immunodeficiency Virus

<400> SEQUENCE: 187

Gln Lys Lys Met Met Asn Ile His Glu Cys Ile Thr Ala Trp Phe Ser
1               5                   10                  15

Lys Asp Pro Val Glu Pro Asp Pro Thr Trp Gly Trp Trp Met Thr Glu
                20                  25                  30

His Gln Gln Ile Arg Phe Ala Ile Gln
                35                  40

<210> SEQ ID NO 188
<211> LENGTH: 42
<212> TYPE: PRT
<213> ORGANISM: Human Immunodeficiency Virus

<400> SEQUENCE: 188

Lys Arg Asp Cys Ile Ala Glu Leu Asp Arg Gln Lys Lys Met Met Ala
1               5                   10                  15

Phe Trp Phe Ser Lys Asp Pro Val Arg Pro Asp Pro Thr Leu Phe Ile
                20                  25                  30

Trp Lys Gly Trp Trp Met Thr Glu His Gln
                35                  40
```

```
<210> SEQ ID NO 189
<211> LENGTH: 5
<212> TYPE: PRT
<213> ORGANISM: Human Immunodeficiency Virus

<400> SEQUENCE: 189

Gln Gln Glu Lys Ser
1               5
```

ASSOCIATION-BASED PREDICTIONS OF PATHOGEN CHARACTERISTICS

CROSS-REFERENCE TO RELATED APPLICATIONS

The application is a Continuation-in-Part of U.S. patent application Ser. No. 10/493,165, entitled "A METHOD FOR IDENTIFYING AND DEVELOPMENT OF THERAPEUTIC AGENTS", filed Sep. 21, 2004, now abandoned, and a Continuation-in-Part of U.S. patent application Ser. No. 10/977,415, entitled "SYSTEMS AND METHODS THAT UTILIZE MACHINE LEARNING ALGORITHMS TO FACILITATE ASSEMBLY OF AIDS VACCINE COCKTAILS," filed Oct. 29, 2004, now abandoned.

BACKGROUND

Living organisms possess various mechanisms for preventing disease states. For instance, some organisms have immune systems that can recognize proteins on pathogens and tumor cells and subsequently neutralize or kill these cells. By way of example, the mammalian immune system provides both humoral-mediated and cellular-mediated immunological defenses. The humoral arm (e.g., B-cells) manufactures antibodies that can neutralize invading pathogens and tumor cells. The cellular arm employs cytotoxic (e.g., CD8+ T cells) and natural killer cells to kill cells recognized as foreign or otherwise abnormal.

CD8+ T cells kill infected cells if they recognize short (approximately 8-11 amino-acid long) sequences (epitopes) of viral protein in association with Major Histocompatibility Complex class 1 (MHC-1) molecules on a cell's surface. These epitopes are generated by normal digestive processes within the cell and are transported to the cell surface where they are presented to CD8+ T cells in association with MHC-I molecules. The particular epitopes that can be presented by a cell depend on the type of MHC-I molecules expressed by the organism. The human MHC molecule is sometimes referred to as the Human Leukocyte Antigen (HLA). The major human MHC-1 genes are referred to as HLA-A, HLA-B and HLA-C. HLA genes are the most polymorphic of all human genes. Indeed, hundreds of HLA-A, HLA-B, and HLA-C alleles have been identified in the human population.

Pathogenic organisms may sometimes mutate and these mutations may allow the organism to evade a host's defense systems. Moreover, subsequent exposure to the host's natural defenses or available therapies lead to the selection of those pathogens most fit to escape the host's natural defenses as well as those less susceptible to available treatments. Thus, pathogen evolution may be driven by the selective pressures of the host's defenses/therapies. Similarly, the vast polymorphisms exhibited by HLA molecules may be driven by the by co-evolving infectious disease threats. This process of evolution and co-evolution is particularly evident in viruses like the human immunodeficiency virus (HIV), herpes viruses and hepatitis viruses such as hepatitis C virus (HCV).

Various therapies have been directed at augmenting an organism's immune system in order to fight disease. By way of example, vaccinations are widely used to stimulate an immune response to a particular organism (e.g., small pox, polio, etc.) and have even been used to fight tumors (e.g., melanoma). Vaccines may be designed to stimulate humoral immunity, cellular immunity or both humoral and cellular immunity.

SUMMARY

The following presents a simplified summary in order to provide a basic understanding of some concepts of the subject matter described herein. This summary is not an extensive overview of the invention. It is not intended to identify key or critical elements of the invention or to delineate the scope of the invention. Its sole purpose is to present some concepts relevant to the subject matter described herein in a simplified form as a prelude to the more detailed description that is presented later.

The subject matter described herein provides system and methods that facilitate vaccine cocktail assembly via machine learning techniques that model sequence diversity. Such assembly can be utilized to generate vaccine cocktails, for instance, directed against species of pathogens that evolve quickly under immune pressure of the host. For example, the systems and methods can be utilized to facilitate design of T cell vaccines for pathogens such HIV. In addition, the systems and methods can be utilized with other applications, such as, for example, sequence alignment, motif discovery, classification, and recombination hot spot detection.

A resultant vaccine cocktail can be referred to as an "epitome," or a sequence that includes all or many of the short subsequences from a large set of sequence data, or population. The novel techniques described herein can provide for improvements over traditional approaches that utilize an ancestral sequence from which diversity mushroomed, an average sequence of a population, or a "best" sequence a population. For example, vaccine cocktails generated by the systems and methods described herein can provide for higher epitope coverage and account for a large amount of local diversity in comparison with the cocktails of consensus, phylogenetic tree nodes and random strains from the data.

In one aspect, a system and/or method that determines epitomes for rapidly evolving pathogens is provided. The system can include an input component that receives a plurality of patches (e.g., sequences of DNA, RNA, or protein, etc.). Such patches can be a subset or all of a population of patches. The received patches can be variable length and conveyed by the input component to a modeling engine. The modeling engine can employ various learning algorithms (e.g., expectation-maximization (EM), greedy, Bayesian, Hidden Markov, etc.) to determine the epitome. For example, the modeling engine can determine a most likely epitome, such as, a sequence (e.g., with the greatest coverage and a shortest sequence for a particular coverage. Upon determining the epitome, it can be sequenced to create a peptide and/or nucleotide.

In another aspect, systems and methods are provided for designing AIDS/HIV vaccine cocktails. In one instance, the methods include obtaining AIDS sequence data of contiguous amino acid subsequences (e.g., all possible subsequences with length that corresponds to a typical epitope), building a plurality of disparate sized patches from the sequence data by iteratively increasing a size of a patch while decreasing an associated free energy (e.g., set equal to zero), aggregating patches to form the AIDS vaccine cocktail by adding a most frequent patch during each iteration (unless the patch was already added). An expectation-maximization (EM) and/or a greedy algorithm can be utilized to optimize respective iterations.

In another instance, the methods include receiving a plurality of HIV related sequences, utilizing the sequences, based on their linear about nine-amino acid epitopes (e.g., substantially equally immunogenic), to create a compact representation of a large number of HIV related peptides, employing a machine learning algorithm to optimize the representation in terms of binding energies, and designing an HIV vaccine cocktail based on the representation. Alternatively, the representation can be estimated from the sequence by parsing the sequences into shorter peptides and creating a mosaic sequence that is longer than any individual sequence.

In yet another instance, the systems include a component that receives a plurality of HIV related nine-mers (or 8-11mers), a component that generates a sequence that epitomizes the plurality of nine-mers (or 8-11mers), a component that employs a greedy algorithm (e.g., initialized with a random nine-mer and a variable binding energy estimate) to jointly update a size of the sequence and a free energy, and a component that utilizes the updated sequence to design an HIV vaccine cocktail. Additionally or alternatively, an expectation-maximization algorithm that concurrently optimizes the updated sequence and a binding energy can be utilized.

The subject matter described herein can be utilized, for instance, to determine the influence of variations within a population on the outcome of disease states (e.g., infections, tumors, etc.) or any other variable, such as the effect of therapeutic agents (e.g., drugs or vaccines). Such information can be used to design diagnostic and therapeutic interventions, personalized treatments and/or to determine susceptibilities.

By way of example, organisms exhibiting genetic polymorphisms can be analyzed at a population level to derive data useful to predict interactions between a human gene product and a target molecule. For instance, human populations can be typed according to HLA alleles and this information correlated at the population level with pathogenic polypeptides. The determined associations can be used to develop new therapies.

One example of an association is HLA-driven mutation. HLA-driven mutation is the phenomenon whereby the mutation of a pathogen is not random, but rather driven by the HLA type of the host. This enables a pathogen to avoid or "escape" that host's immune system. For example, if a patient has an A*0204 HLA type, the pathogen will favor mutations that avoid A*0204 epitopes. Correlations between point-wise (single site) mutations in the HIV sequence and the HLA types of infected individuals can be used to pinpoint such associations (e.g., there exists a strong association between HLA type B*4402 and the mutation of the virus at position gp120-13).

By way of example, the relationships can be used to train a machine learning algorithm to learn a classifier to make predictions. The associations may be based, for instance, on Major Histocompatibility Complex (MHC)-driven mutations of an organism or any other association between a polymorphic human gene and a characteristic of a pathogen. In one embodiment, the machine learning techniques learn the classifier based on epitopes that are known to be presented (and known to be not presented) by particular MHC molecules. The classifier may be used to predict new epitopes and the MHC molecules that present them. Any classifier (e.g., logistic regression, neural net, decision tree, support vector machine, etc.) may be used. The predicted epitopes are useful, for instance, to design vaccine immunogens.

By way of another example, for each HLA-position association, it can be assumed that there is at least one epitope in the vicinity of that association. To look for the most likely epitope that can be recognized by the immune system of that HLA type, the machine learning classifier can be applied to each 8-11 long amino-acid sequence in the vicinity of the association. A search can be conducted in about a 33-long window on either side of the association position. Since the positions flanking an epitope can influence whether it is presented on a cell's surface, the 33-long window allows for a 12-amino-acid-long flanking region on either side of a 9-amino-acid-long epitope.

By way of another example, logistic regression with features selected by the wrapper method can be used to predict epitopes. Positive examples include the 9-mers obtained from the LANL (hiv-web.lanl.gov) (Los Alamos National Laboratory) and SYFPEITHI (www.syfpeitbi.de/) (Institute for Cell Biology Department of Immunology) databases. Negative examples can be generated at random from the marginal distribution of amino acids from the positive examples. The features used for prediction comprise: (1) the 2-4 digit HLA of the epitope; (2) the supertype of that HLA; (3) the amino acid at each position in the epitope; and (4) the chemical properties of each amino acid at each position in the epitope and conjunctions 1+3, 1+4, 2+3, and 2+4.

A vaccine immunogen can be built by overlapping epitopes and corresponding flanking regions. For example, the hypothetical immunogen ABCDEFGHIJKLM (where each letter denotes an amino acid), is only 13 amino acids long, but covers the two 8-long epitopes ABCDEFGH and FGHIJKLM. There are numerous strategies for delivering such immunogens such as delivering each sequence in an epitome on its own viral vector, concatenating the sequences in the epitomes and delivering them on a single viral vector, and/or each sequence can be further subdivided (e.g., to avoid immunodominance), and each component delivered on a separate viral vector.

By way of example, to determine an epitome for use as an HIV vaccine, a set of epitopes, the HLA molecules that present them and one or more optimization criteria are identified. The epitope-HLA pairs can be previously known (e.g., hiv-web.lanl.gov/content/immunology/index) and/or can be predicted by epitope prediction techniques. The optimization criteria can be selected based on a population of known HIV sequences and a similar population of people who may be infected. For instance, the optimization criteria can reflect the idea that if a vaccinated person with a given HLA is exposed to a given sequence (or collection of sequences), only the epitopes in the sequence that are (1) present in the vaccine (or that will cross react with CD8+ T cells stimulated by the vaccine) and (2) can be presented by an HLA molecule expressed by the patient will contribute to immune protection. One example of an optimization criterion is the expected number of crossreacting epitopes per patient, where expectation is taken over the given population of individuals and the given population of sequences.

There are different models for determining whether CD8+ T cells stimulated with one sequence will cross-react with another epitope. One example of such a model assumes that there must be an exact match between the sensitizing peptide and the reacting epitope. Another example of a model assumes that the sensitizing peptide and the reacting epitope must differ by at most one conservative amino acid change.

An HIV epitome can be constructed according to the one or more optimization criteria by utilizing an optimization algorithm or combinations of optimization algorithms. Any suitable optimization algorithm can be used. For instance, a greedy algorithm that constructs a collection of sequences which together yield a large optimization score can be employed. The greedy algorithm can iteratively insert (usually with overlap) a single epitope into the collection of sequences such that the optimization score per unit length (where length is the total length of all the sequences) increases the most. This procedure produces a series of epitomes, each with an optimization score and a length. External considerations can be used to choose the optimal tradeoff of score versus length.

The subject matter described herein can provide for improvements over traditional approaches that utilize an ancestral, average or a "best" sequence of a population. For instance, since consensus models and/or phylogenetic tree models are not well-suited to accounting for the large amount of diverse strains of HIV, vaccine cocktails generated by the subject matter described herein can provide for higher epitope coverage.

The following description and the annexed drawings set forth in detail certain illustrative aspects of the subject matter described herein. These aspects are indicative, however, of but a few of the various ways in which the principles of the invention may be employed and the present invention is intended to include all such aspects and their equivalents. For ease of description, HIV has been selected to illustrate how the subject matter described herein can be employed. However, the subject matter so described may be applied to a wide range of analyses including but not limited to, for example, herpes virus infections and hepatitis virus infections.

BRIEF DESCRIPTION OF THE DRAWINGS

Figure 10:
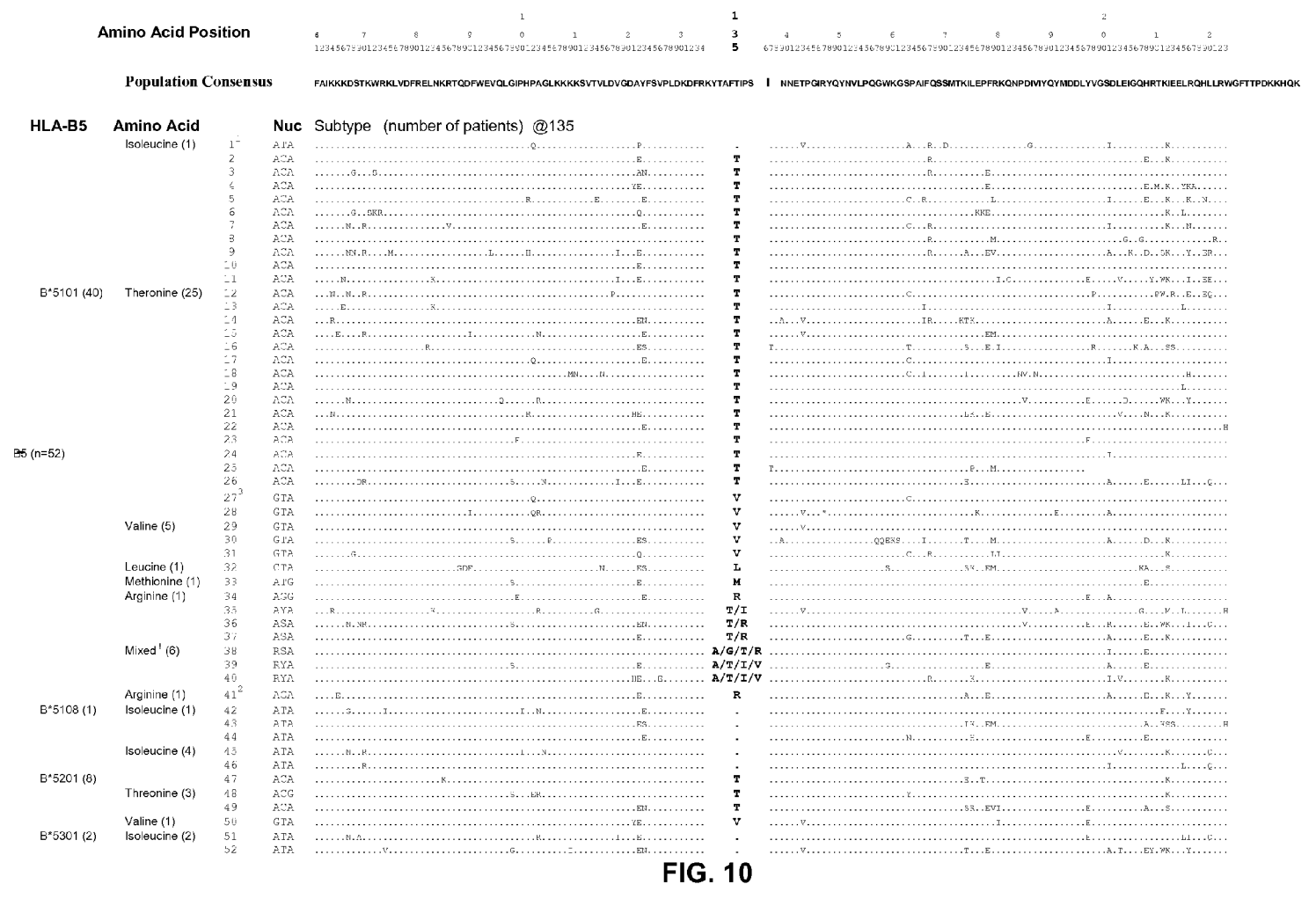

FIG. 10 shows HIV-RT amino acid sequences in all 52 patients in a cohort of serologically defied HLA-B5 (patients 1-52) compared with population consensus sequence. HIV-1 RT sequences are grouped according to the HLA-B subtype of the patient. In all sequences, a dot (.) indicates no differences from consensus. Amino acids different to consensus are shown. Where quasispecies with different amino acids were detected, the most common amino acid is shown, except at position 135 where all detected amino acids in a mixed viral population are shown. All but one of the forty patients (98%) with the HLA-B*5101 subtype have a substitution of the consensus amino acid isoleucine (I) at position 135, most commonly with threonin (T). [1]The sequence without I135x is that of the single HLA-B*5101 patient who had HAART during acute HIV infection. [2]This patient did not have molecular genotyping. [3]This patient was an HLA-B*5101/B*5201 heterozygote but was counted only once in the HLA-B*5101 group. The four (4) amino acid sequence in line 30 corresponds to SEQ ID NO: 189.

FIG. 13 shows the frequency distribution of the estimated strength of HLA-restricted immune responses that would be induced by each of SIV, clade A virus, lade C virus, HXB2 virus, our population consensus virus sequence, and a hypothetical vaccine in response to each of the potential incoming viruses in a West Australian population using the viral load results as illustrated in the estimated change in viral load column shown in Table 6.

FIG. 14 illustrates a potential HIV protease therapeutic.

FIG. 15 illustrates a potential HIV RT therapeutic.

DETAILED DESCRIPTION

Figure 1:
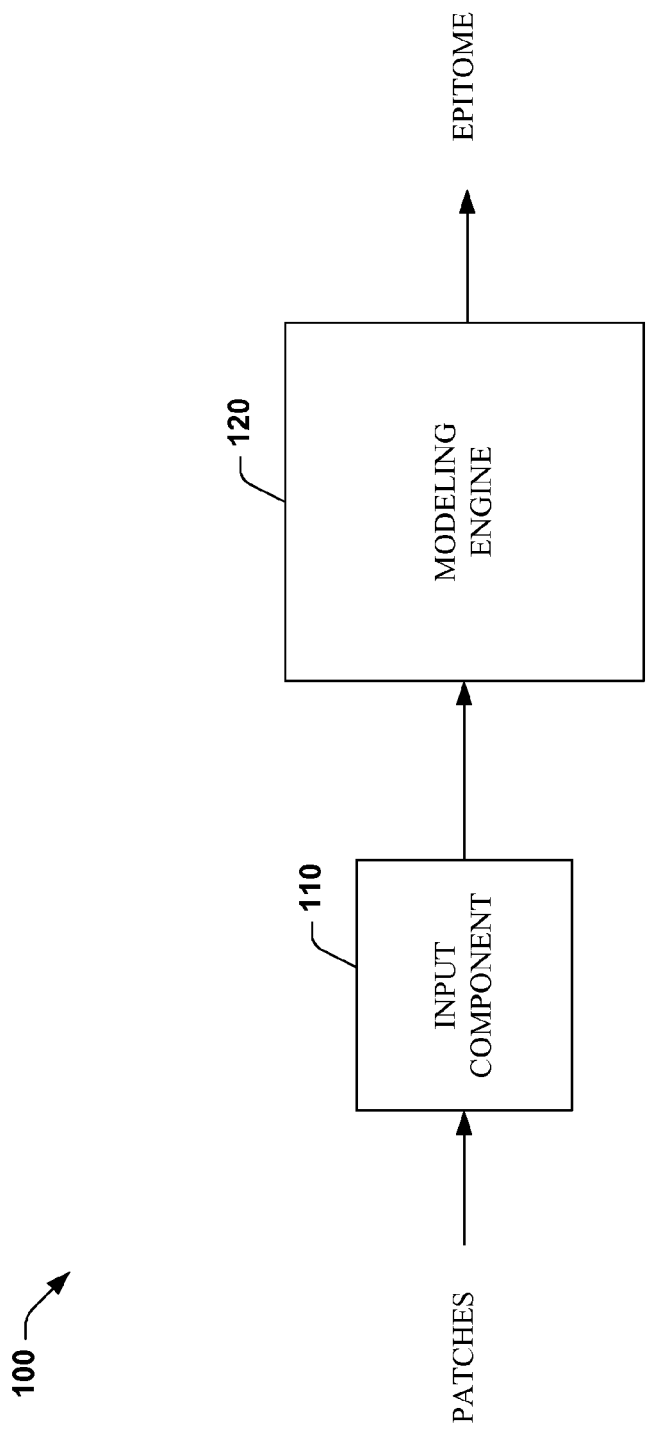
FIG. 1 illustrates an exemplary system to facilitate making predictions.

The subject matter described herein relates to systems and methods that utilize machine learning to model sequence diversity to facilitate vaccine cocktail assembly. Suitable machine learning techniques include cost functions, expectation-maximization (EM) and greedy algorithms, for example. Such assembly can be utilized to generate vaccine cocktails for species of pathogens that evolve quickly under immune pressure of the host. For example, the systems and methods can be utilized to facilitate design of T cell vaccines for pathogens such HIV.

The subject matter is described with reference to the drawings, wherein like reference numerals are used to refer to like elements throughout. In the following description, for purposes of explanation, numerous specific details are set forth in order to provide a thorough understanding of the present invention. It may be evident, however, that the subject matter described herein may be practiced without these specific details. In other instances, well-known structures and devices are shown in block diagram form in order to facilitate describing the subject matter.

As utilized herein, the term "sequence" generally refers to a sequence that includes all or many of the short subsequences (patches) from a large set or population of sequence data and/or a sequence whose subsequences (patches) can be assembled to generate a wide range of representative sequences of a desired category. Suitable categories include sequences associated with a specific species, such as HIV, sequences from a specific clade, and/or sequences associated with an acute or chronic phase of infection. Sequences include, for instance, nucleotide sequences (e.g., DNA, RNA) and/or amino acids.

Sequence identity numbers (SEQ ID NO:) included in this specification have been prepared using the program PatentIn Version 3.3. Each sequence is identified in the sequence listing by the numeric indicator <210> followed by the sequence identifier (e.g. <210>1, <210>2, etc.). The length, type of sequence and source organism for each sequence are indicated by information provided in the numeric indicator fields <211>, <212> and <213>, respectively. Sequences referred to in the specification are defined by the information provided in numeric indicator field <400> followed by the sequence identifier (e.g. <400>1, <400>2; etc.).

FIG. 1 illustrates a system 100 that determines epitomes (vaccine cocktails) for rapidly evolving pathogens such as HIV. The system 100 comprises an input component 110 and a modeling engine 120. The input component 110 can receive a plurality of patches that can be a subset or all of a population of patches, wherein such patches can be utilized to construct an epitome. The received patches can be variable length, for example, nine-mers, ten-mers, etc. The input component 110 can convey the patches to the modeling engine 120, which can employ various learning algorithms (e.g., expectation-maximization (EM), greedy, Bayesian, Hidden Markov, etc.) that can utilize the patches to determine the epitome. For example, the modeling engine 120 can be utilized to determine a most likely epitome. In one instance, the most likely epitome is defined as the sequence with the greatest coverage. In another instance, the most likely epitome is defined as the shortest sequence for a particular coverage. Upon determining the epitome, it can be utilized to create peptide and/or nucleotide sequencing.

Traditional approaches to designing such vaccines typically model evolution as a process of random site-independent mutations. However, the environment can affect different pieces of the genome and/or peptides in a single protein differently. On the population level, this can lead to creation of several functional versions of each piece and an impression of immense diversity. In addition, with traditional approaches the log mutation scores for sites in a sequence are summed together or mutation probabilities are multiplied together to define a number corresponding to an evolutionary distance between two sequences, when separate pieces commonly have different evolutionary distances. The novel approach employed by the system 100 can provide for improvements over traditional technique via utilizing machine learning techniques. By way of example, the system 100 can be employed to model sequence diversity to facilitate generating of vaccine cocktails. Such cocktails can provide for higher epitope coverage in comparison with the cocktails of consensi, phylogenetic tree nodes and random strains from the data.

Figure 2:
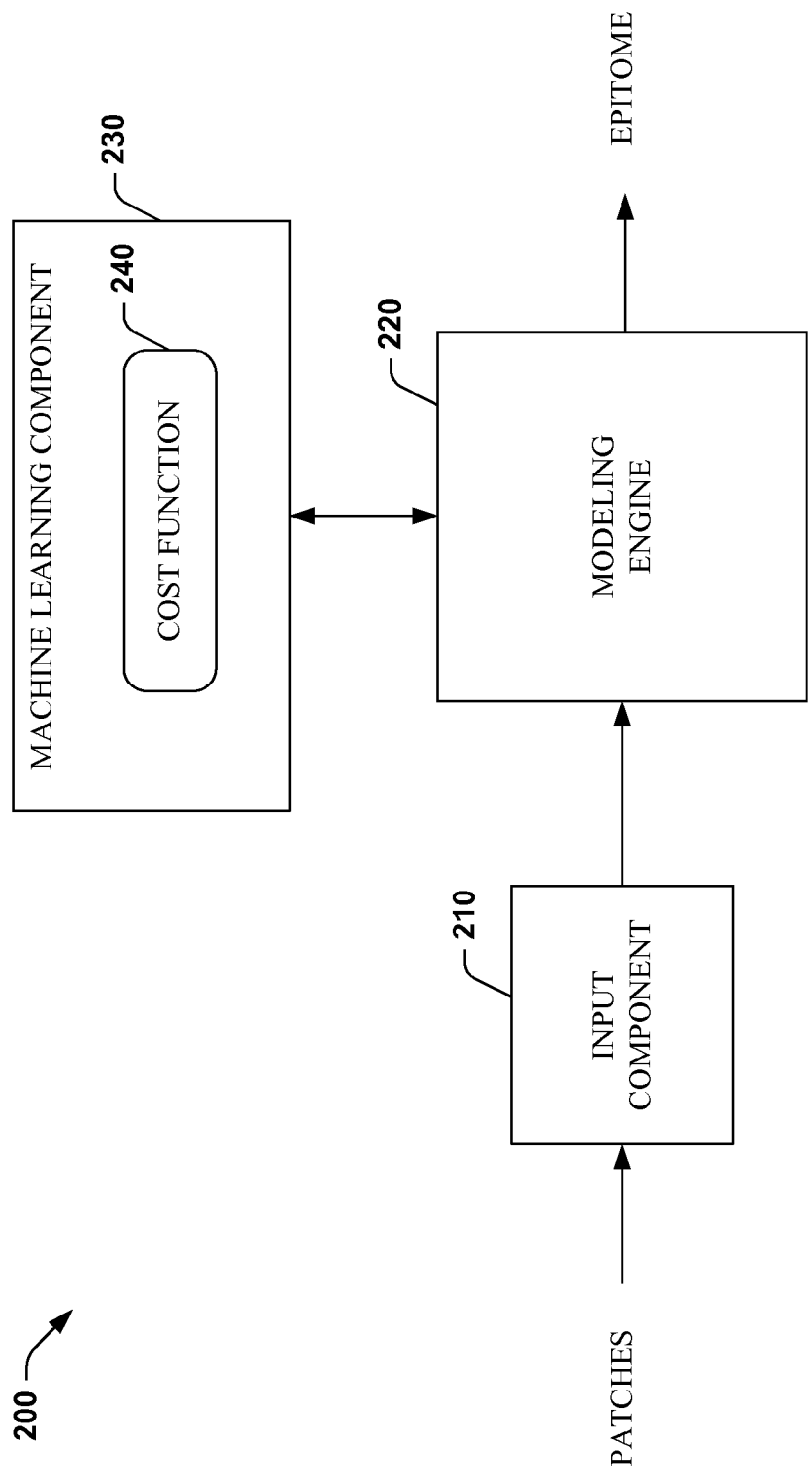
FIG. 2 illustrates another exemplary system to facilitate making predictions.

FIG. 2 illustrates a system 200 that determines epitomes via a cost function. The system 200 comprises an input component 210, a modeling engine 220, and a learning component 230. The input component 210 can receive patches associated with a population and convey the patches to the modeling engine 120, which can utilize the patches to determine the epitome. The modeling component 220 can employ the learning component 230 to facilitate determining the epitome.

By way of example, the learning component 230 can employ a cost function 240 to learn the epitome. For instance, the learning component 230 can employ a cost function that measures the similarity of sequence data with an estimate of the epitome. By way of example, a set of nucleotide or amino acid patches defined by $x=\{x_{ij}\}$, wherein i=1, ..., M (M is a sequence index) and j=1, ..., N (N is a site (position) index) can be received by the input component 210 and conveyed to the modeling component 220. The modeling component 220 can utilize the patches to construct an M×N matrix/array of sequence data (an epitome) that can be input to a learning algorithm that renders the epitome as a smaller array $e=\{e_{mn}\}$ of size Me×Ne, wherein MeNe<<MN. For example, the data can include 12 sequences (M=12) with lengths of about 42 (N=42), whereas the epitome size after utilizing the learning algorithm can be reduced to Me=1 and Ne=50. It is to be appreciated that the values utilized in the above example are illustrative and do not limit the invention. Moreover, it is to be appreciated that the learning algorithm can optimize the epitome in order to maximize a number of short subsequences that are present in the input data, and the input data can be described by its epitome and a mapping that links the sites in the data to sites in the epitome.

In order to establish such mapping, the sequence set (patches) x can be represented as a set of short overlapping subsequences, wherein respective subsequence $x_S$ can include letters from a subset of sequence positions S. Each index in an index set S generally is two dimensional, pointing both to a sequence and a position within the sequence. These subsequences can be defined on arbitrary biological sequences. For example, if X contains M sequences of length N, then the total number of contiguous patches in the data of length n is M(N−n) and, thus, the cardinality of S is M(N−n). For each patch $x_S$, its index set S can be mapped to a hidden set of epitome indices T. In many instances contiguous patches $x_S$ can be assumed to map to contiguous patches $e_T$ in the epitome so the set T can be identified by the first index in the set. A number of possible mappings for each patch are defined by Me(Ne−n). For HIV amino acid sequence data, these subsequences generally are peptides that can correspond to epitopes. With T cell HIV vaccines, the patch length may be equal to the epitope length (e.g., 8-11 amino acids). However, the context in regions adjacent to the epitopes can affect HLA binding so the patch length may be longer, for example, up to about 33 amino acids.

The cost function employed by the learning component 230 to optimize the epitome depends on the application. For example, a cost function that accounts for various acts that are needed to mount an effective immune response can be utilized, wherein each act can have an associated cost in the form of an energy. This energy can be viewed as a negative log-probability of an event. By way of example, a cost function can be selected to account for the acts utilized to kill an infected cell, for example, the acts needed for a vaccine e to generate an effective immune response. The vaccine generally is chopped up by cellular mechanisms and short subsequences (e.g., epitopes) are presented on the surface of the processing cell. A positive immune response happens if the clone of the same T cell can later bind to a virus epitope $x_S$ that an infected cell presents on its surface, initiating the killing of the infected cell.

In a cell processing a vaccine e, a peptide can be presented on the surface and bound to a T cell in a process with priming energy E(T). The priming energy typically is the sum of the cleavage, HLA binding, transport and/or T cell binding energies, which can influence priming of an appropriate T cell to attack a cell that presents an epitope pattern similar to $e_T$. In addition, sequence data neighboring an epitope can have an impact on presentation and, thus, on the priming energy. A T cell primed with the vaccine epitope $e_T$ typically attacks a cell that presents a virus epitope $x_S$ in a process with attack energy $E(x_S, e_T)$. This energy depends on the cross-reactivity of the T cell. If the patch length is selected so as to account for each epitope plus its neighboring contextual sequence data, then only a piece of a window corresponding to the actual epitope can be utilized to determine the attack energy. The T cell attack energy is lowest when the epitope substantially matches the amino acid pattern on the T cell. The energy associated with priming with $e_T$ and attacking $x_S$ can be determined by summing the two energies E(T) and $E(x_S, e_T)$.

In general, for an effective immune response the energy for data set (e.g., many patches from many virus sequences) diversity and/or an ability to rapidly evolve can be considered. In particular, the total energy typically increases for each patch from the data set that does not have a corresponding patch in the epitome that gives a low priming plus attack energy. Equation 1 provides one example of an energy E(x) that satisfies this requirement.

$$E(x) = \sum_S \min_T (E(T) + E(x_S, e_T)).  \qquad \text{Equation 1:}$$

An effective vaccine can be obtained by finding an epitome that minimizes this energy. It is to be appreciated that Equation 1 is provided for illustrative purposes and sake of brevity, and does not limit the invention.

Each of the above energies (E(T) and $E(x_S, e_T)$) can be considered an energy associated with a stochastic process at equilibrium, wherein the energy is equal to a negative log-probability of the event or process. A suitable priming probability that can be employed in accordance with the subject invention is defined by Equation 2:

$$p(T) \propto \exp(-E(T)),  \qquad \text{Equation 2:}$$

and a suitable attack probability that can be employed in accordance with the subject invention can be defined by Equation 3:

$$p(x_S | e_T) \propto \exp(-E(x_S, e_T)).  \qquad \text{Equation 3:}$$

Exponentiating both sides of the above equations for the total energy E(x) renders Equation 4, which is a probability of the data set x in terms of the priming and attack probabilities:

$$p(x) \propto \prod_S \max_T (p(x_S | e_T) p(T)),  \qquad \text{Equation 4:}$$

which illustrates an expression that optimizes the epitome via maximizing the likelihood of independently generating all patches from the data set, wherein patch $x_S$ is generated from epitome patch $e_T$ with probability $p(x_S|e_T)$ and patch $e_T$ is selected from the epitome with probability p(T).

In instances where $\Delta E(x_S, e_T)$ is relatively high (e.g., except for substantially perfect matches between $x_S$ and $e_T$), the total energy can be closely approximated as const −rE, wherein r is the number of the patches $x_S$ that match their corresponding epitome patch $e_T$ and E is the binding energy for such matches. The foregoing can be derived by letting $\Delta E$ go to infinity uniformly across mismatches. The const term can depend on $\Delta E$ and/or the total number of patches K, and typically does not depend on the fraction of the matched patches. Thus, for a given size of the epitome, the quality of the vaccine can depend only on the percentage of the matched epitopes.

An exemplary functional form that can behave in this manner in the limit involves the letter substitution probability θ. This probability can be uniformly or non-uniformly spread over any or all other possibilities (e.g., other three nucleotides in case of DNA/RNA sequence models or other nineteen amino acids in case of protein models) as illustrated in Equation 5:

$$p(x_S | e_T) = \theta^{|x_S \ne e_T|} (1-\theta)^{|x_S = e_T|},  \qquad \text{Equation 5:}$$

wherein || is the number of elements in the vector argument that are true, for example, $|x_S = e_T|$ is the number of elements on which the two patches disagree. When the variability parameter θ can approach zero, an exact match model, which is a conservative choice for vaccine design as it limits the assumptions on cross-reactivity, can be utilized. The binding energy model corresponding to this distribution is illustrated in Equation 6:

$$E_{x_S}, e_T = -n\log(1-\theta),$$ Equation 6:

$$\Delta E_{x_S}, e_T = |x_{ij} \neq e_{T(ij)}|\log\frac{1-\theta}{\theta}.$$

With amino acid epitomes, the substitution parameter θ can be defined so that it decreases the probability of non-conservative amino acid exchange, thus reflecting to some extent the current understanding of the T cell cross-reactivity. The θ parameter can also be position-dependent. It is to be appreciated that there are other ways of describing the position-specific variability. For example, a full multinomial distribution over possible letters can be utilized in accordance with the subject invention. Utilizing this approach, the full multinomial distribution over possible letters, such as, for example, θA, θC, θT, θG, wherein θx is the probability of letter x at a given position and θA+θC+θT+θG=1 can be employed.

If the epitome is viewed as a stochastic model, the optimization criterion can be written as a likelihood of attacking all epitopes $x_S$ as illustrated in Equation 7:

$$p(\{x_S\}) = \prod_S \sum_T p(x_S \mid e_T).$$ Equation 7:

Under a conservative assumption, wherein θ is approximated to equal to one, this cost can become equivalent to the epitome's coverage of substantially all virus epitopes. If the cost is defined in terms of the total energy barrier summed over substantially all virus epitopes $x_S$, then the free energy can be defined as illustrated in Equation 8:

$$F = \sum_S \sum_T q(T \mid S)\log\frac{p(T \mid S)}{p(x_S \mid e_T)p(T)},$$ Equation 8:

which combines the binding energies described above via an auxiliary distribution q(T|S) for each data patch S.

Individual patch energies −log p($x_S$|$e_T$)−log p(T) can be summed to form an estimate of the total energy barrier to the immunity against all forms of the virus if the mapping variable T is known for each sequence fragment S. However, with some probability any piece of the epitome can be chopped and presented by cellular mechanisms and utilized to prime an appropriate T cell, which could later, as a memory cell, bind to an arbitrary HIV patch $x_S$. Thus, similar segments of the epitome can potentially represent a substantially similar antigen $x_S$. The distribution over the epitome correspondence is expressed through q(T|S). In order to compute the average energy over all mappings, an integration under q as a measure of posterior probability of matching the data epitopes to the appropriate epitome patches can be employed. In addition, if the epitome has multiple patches that represent some data epitope $x_S$, such epitope can be more effective than an epitome that has only one way of providing adaptive immunity to this epitope. Thus, the entropy of the distribution q offsets the binding energy, and the free energy of the epitome sequence can be expressed as above. It is to be appreciated that although the epitome and the viruses can go through substantially similar acts, there is no total symmetry of S and T in Equation 8 when optimizing targeting all likely targets S in the virus instead of optimizing the intersection between epitome and a set of viruses.

The free energy minimum can be equal to the negative log likelihood as illustrated in Equation 9:

$$-\log p(\{x_S\}) = \arg\max_q F.$$ Equation 9:

Maximizing the likelihood with respect to the epitome e can be equivalent to minimizing the free energy with respect to the posterior distributions q(T|S) for all S and the epitome e. A suitable assignment in the posterior distribution q can require an exact match (e.g., θ=0).

Figure 3:
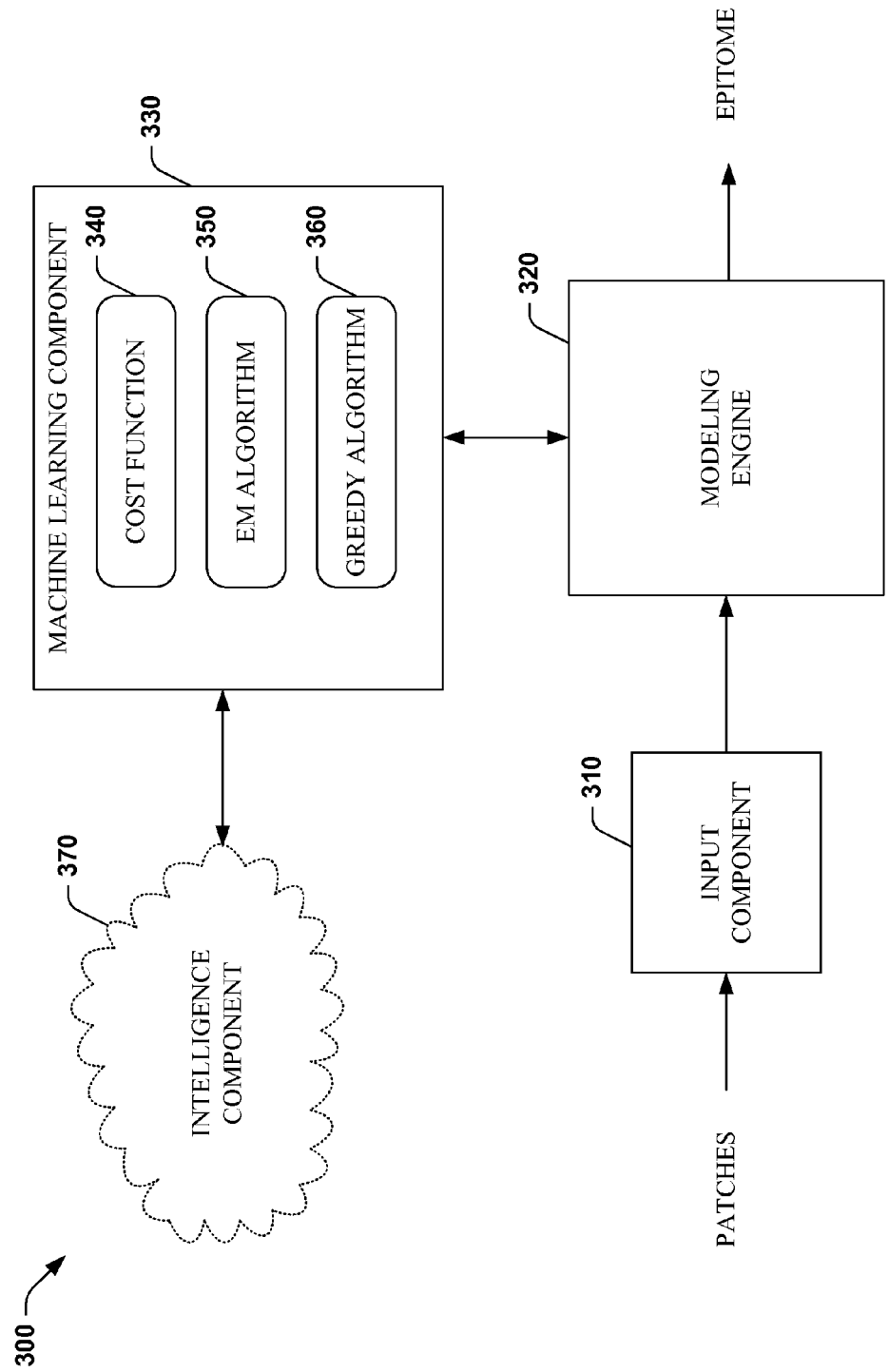
FIG. 3 illustrates yet another exemplary system to facilitate making predictions.

It is to be appreciated that some epitopes are known, but many are not. By studying the escapes in genes, by using databases of epitopes that are known to be immunogenic for some HLA types, or by studying the MHC/cleavege/transport binding data, the probability p(S) can be associated with each peptide $x_S$ in the data, for example, according to how likely the observed pattern is to be presented on the surface of the infected cell, which is the prerequisite for the T cell immunity. If a peptide is not going to be presented, it needs not be included in the epitome and the free energy is defined as illustrated in Equation 10:

$$F = \sum_S p(S) \sum_T q(T \mid S)\log\frac{p(T \mid S)}{p(x_S \mid e_T)p(T)}.$$ Equation 10:

Utilizing a conservative assumption (as discussed above), the vaccine optimization algorithm can be defined by Equation 11:

$$e = \lim_{\theta \to 0} \arg\min_e \min_q F.$$ Equation 11:

FIG. 3 illustrates a system 300 that determines epitomes via an expectation-maximization (EM) algorithm. The system 300 comprises an input component 310, a modeling engine 320, and a learning component 330. The input component 310 can receive patches and convey them to the modeling engine 320, which can utilize the sequences to determine the epitome. The modeling engine 320 can employ the learning component 330, which can utilize a cost function 340, an EM algorithm 350, and/or a greedy algorithm 360. The modeling engine 320 can employ the EM algorithm 350 to facilitate determining the epitome. For example, by considering the size of the epitome as prescribed (e.g., by vaccine the delivery constraints) and utilizing an initial random guess for the epitome parameters, the above can be performed via an iterative optimization by utilizing the EM algorithm 350.

By way of example, for each $x_S$ the posterior distribution q of positions T can be estimated by Equation 12:

$$q(T \mid S) = \frac{p(xS \mid eT)p(T)}{\sum_T p(xS \mid eT)p(T)}.$$ Equation 12:

The epitome that minimizes the free energy can be re-estimated as illustrated in Equation 13 and Equation 14:

$$e_{mn} = \underset{e_{mn}}{\arg\max} \sum_{T(i)=(m,n)} q(T \mid S)[x_{s(i)} = e_{mn}], \text{ and} \quad \text{Equation 13:}$$

$$\theta = \frac{\sum_{m,n}\sum_{s} p(S) \sum_{T(i)=(m,n)} q(T|S)[x_{s(i)} \neq e_{mn}]}{\sum_{m,n}\sum_{s} p(S) \sum_{T(i)=(m,n)} q(T|S)}. \quad \text{Equation 14:}$$

Iterating these equations is an expectation maximization (EM) algorithm for the epitome model, which reduces the free energy in each act, thus converging to the local minimum of the free energy and the local maximum of the likelihood.

The EM algorithm 350 can jointly and concurrently optimize both the epitome and the binding energy parameters $\theta$. The algorithm can be initialized with a random epitome and a relatively large variability estimate $\theta$. After several iterations, $\theta$ generally decreases as the epitome starts to more closely match the data and the uncertainty contracts. The energy barrier $\Delta E_{x_s,e_T}$ to non-exact matches can become relatively steep capturing the conservative assumption on high T cell specificity. If the epitome is not long enough, then the algorithm decreases the allowed variability (and thus increases specificity) to a level where the balance between covering all the data and allowing for as little cross-reactivity as possible is reached for the assumed energy model. The variability can be further decreased to force the model to fit as many patches as possible without any latitude on cross-reactivity. It is to be appreciated that various other algorithms such as the greedy algorithm, Hidden Markov model, neural network, and/or Bayesian-based algorithms can be utilized in accordance with an aspect of the subject invention. For example, the greedy algorithm can be utilized to jointly update the size of the epitome sequence or sequences and the free energy in a greedy fashion.

Optionally, an intelligence component 370 can be employed in accordance with an aspect of the invention. In one instance, the intelligence component 370 can be utilized to facilitate determining which learning algorithm to employ. For example, the machine learning component 360 can provide various cost functions, expectation-maximization algorithms, greedy algorithms, etc. as described above. The intelligence component 370 can determine which algorithm(s) should be employed, for example, based on a desired vaccine, a set of input patches, epitope length, etc. In addition, the intelligence component 370 can perform a utility-based analysis in connection with selecting an algorithm to utilize, with determining an epitome, and/or with optimizing an epitome.

In another aspect of the invention, the intelligent component 370 can perform a probabilistic and/or statistic-based analysis in connection with inferring and/or determining a suitable machine learning algorithm and/or an epitome. As utilized herein, the term "inference" and variations thereof refer generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification (explicitly and/or implicitly trained) schemes and/or systems (e.g., support vector machines, neural networks, expert systems, Bayesian belief networks, fuzzy logic, data fusion engines . . . ) can be employed in connection with performing automatic and/or inferred action in connection with the subject invention.

Figure 4:
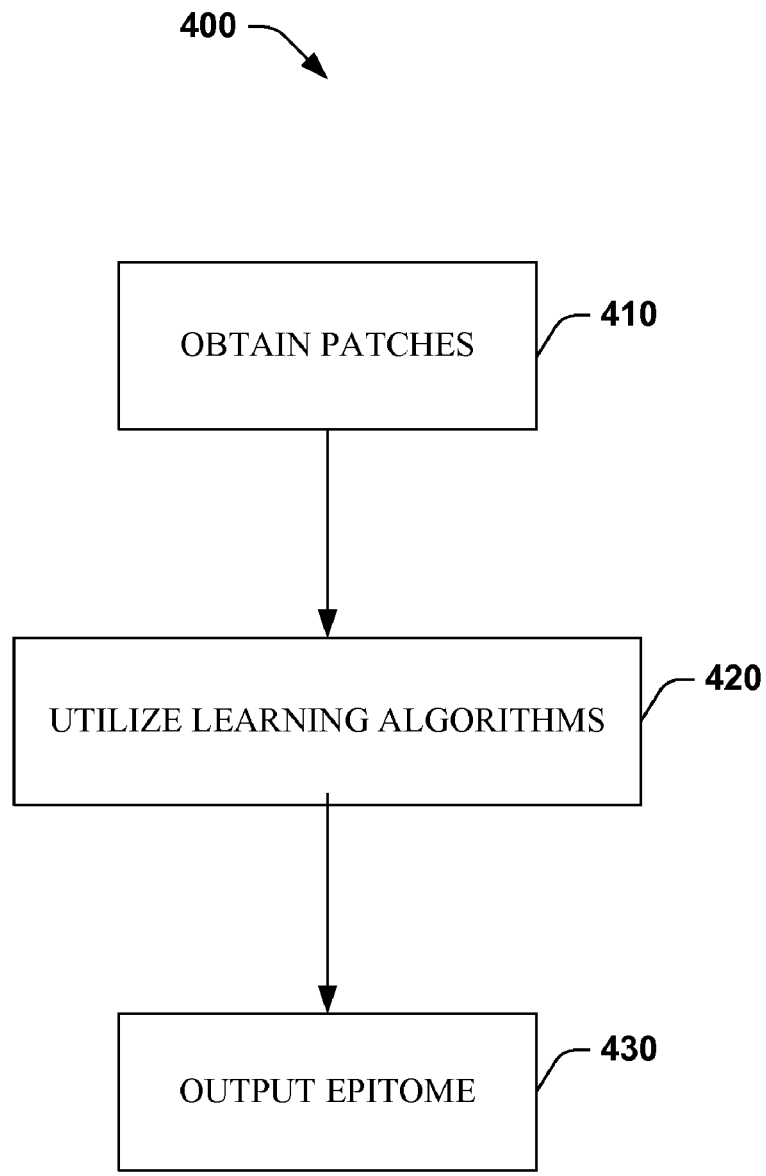
FIG. 4 illustrates an exemplary method for making predictions.

FIG. 4 illustrates a methodology 400 that determines epitomes for pathogens such as HIV. For simplicity of explanation, the methodology is depicted and described as a series of acts. It is to be understood and appreciated that the present invention is not limited by the acts illustrated and/or by the order of acts, for example acts can occur in various orders and/or concurrently, and with other acts not presented and described herein. Furthermore, not all illustrated acts may be required to implement the methodology in accordance with the present invention. In addition, those skilled in the art will understand and appreciate that the methodology could alternatively be represented as a series of interrelated states via a state diagram or events.

At 410, a plurality of patches, or sequences, which can be a subset or all of a population of sequences, is received. Such patches can be variable length, for example, nine-mers, ten-mers, etc. At 420, various learning algorithms can be utilized to determine the epitome, based on the received sequences. For examples, learning algorithms such as a cost function (as described herein), an expectation-maximization (EM) algorithm (as described herein), a greedy algorithm, Bayesian models, Hidden Markov models, neural networks, etc. can be employed in connection with various aspect of the subject invention. It is to be appreciated that the resultant epitome can be a most likely epitome such as an epitome that includes a sequence with the greatest coverage, a shortest sequence for a particular coverage, etc. At reference numeral 430, the epitome can be output. It is to be appreciated that such an epitome can be utilized to create peptide and/or nucleotide sequencing to generate an AIDS vaccine cocktail. This novel approach can provide for improvements over traditional techniques by modeling sequence diversity through machine learning. Resulting vaccines (for HIV) can provide for higher epitope coverage in comparison with the cocktails of consensi, phylogenetic tree nodes and random strains from the data.

Figure 5:
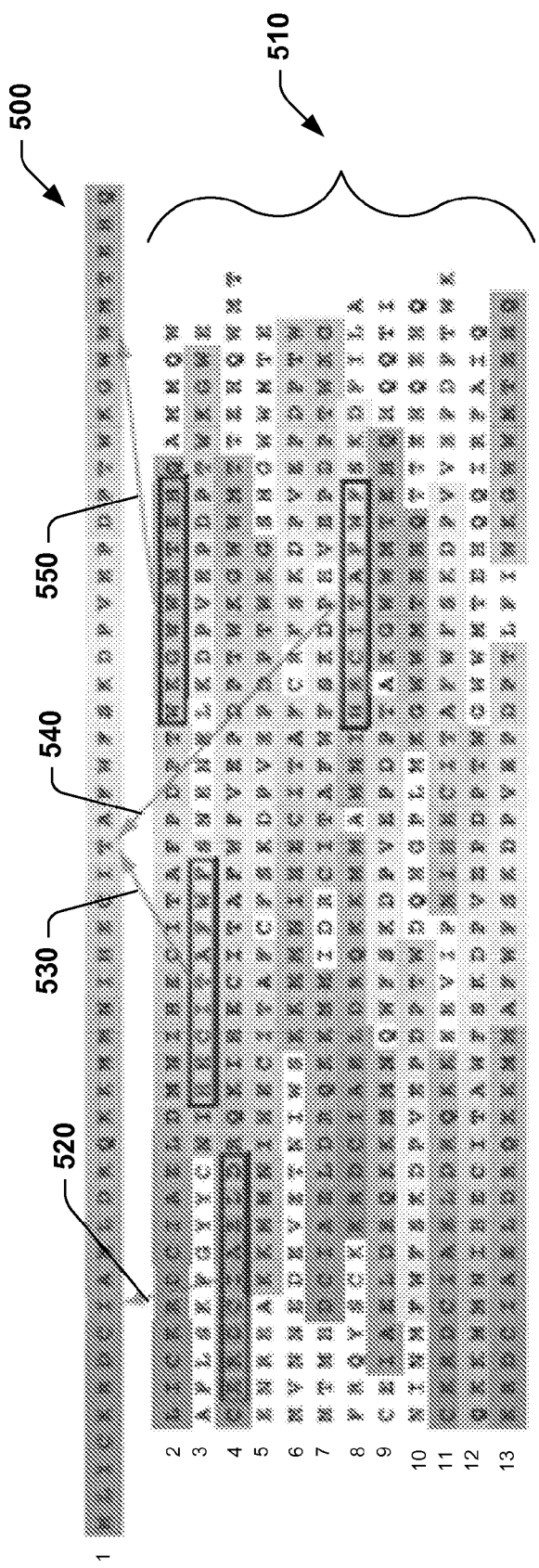
FIG. 5 illustrates an exemplary epitome. The identified row numbers and their corresponding SEQ ID NO is provided as follows: Row 1 (SEQ ID NO: 176); Row 2 (SEQ ID NO: 177); Row 3 (SEQ ID NO: 178); Row 4 (SEQ ID NO: 179); Row 5 (SEQ ID NO: 180); Row 6 (SEQ ID NO: 181); Row 7 (SEQ ID NO: 182); Row 8 (SEQ ID NO: 183); Row 9 (SEQ ID NO: 184); Row 10 (SEQ ID NO: 185); Row 11 (SEQ ID NO: 186); Row 12 (SEQ ID NO: 187); and Row 13 (SEQ ID NO: 188).
Figure 6:
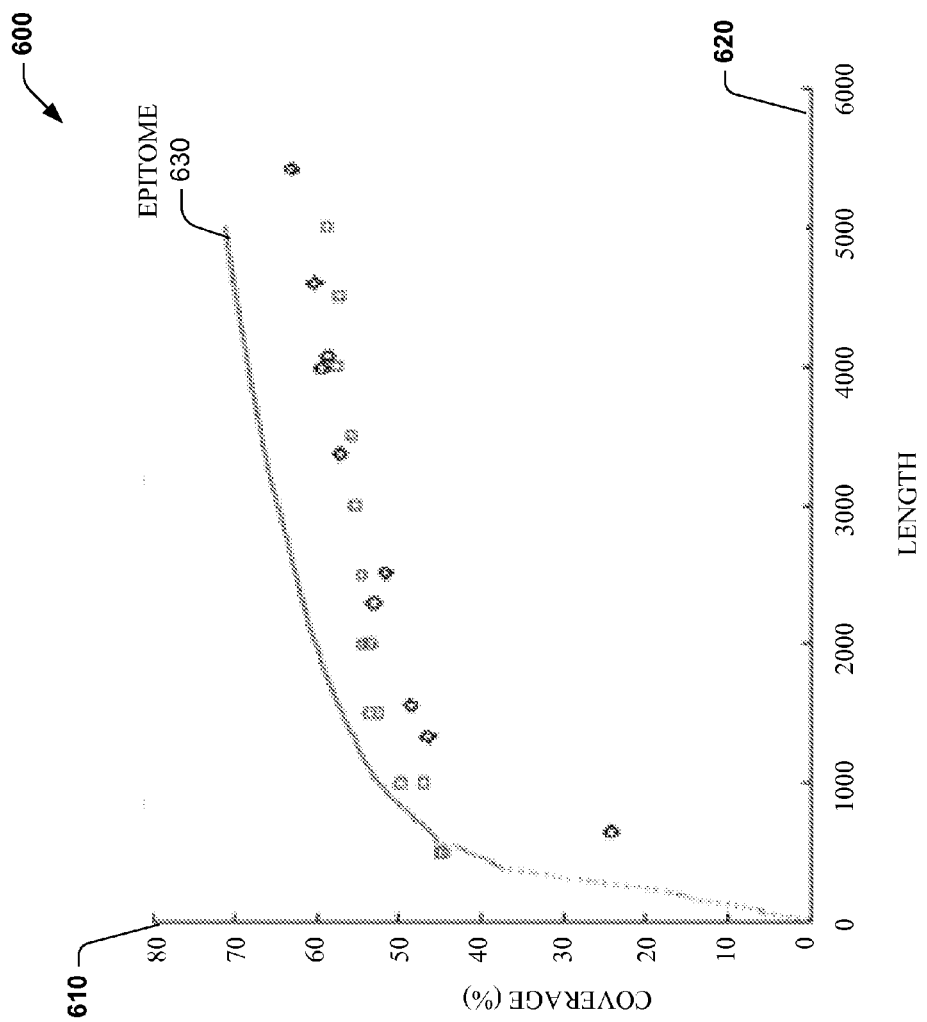
FIG. 6 is a graph depicting gene coverage versus length.
Figure 7:
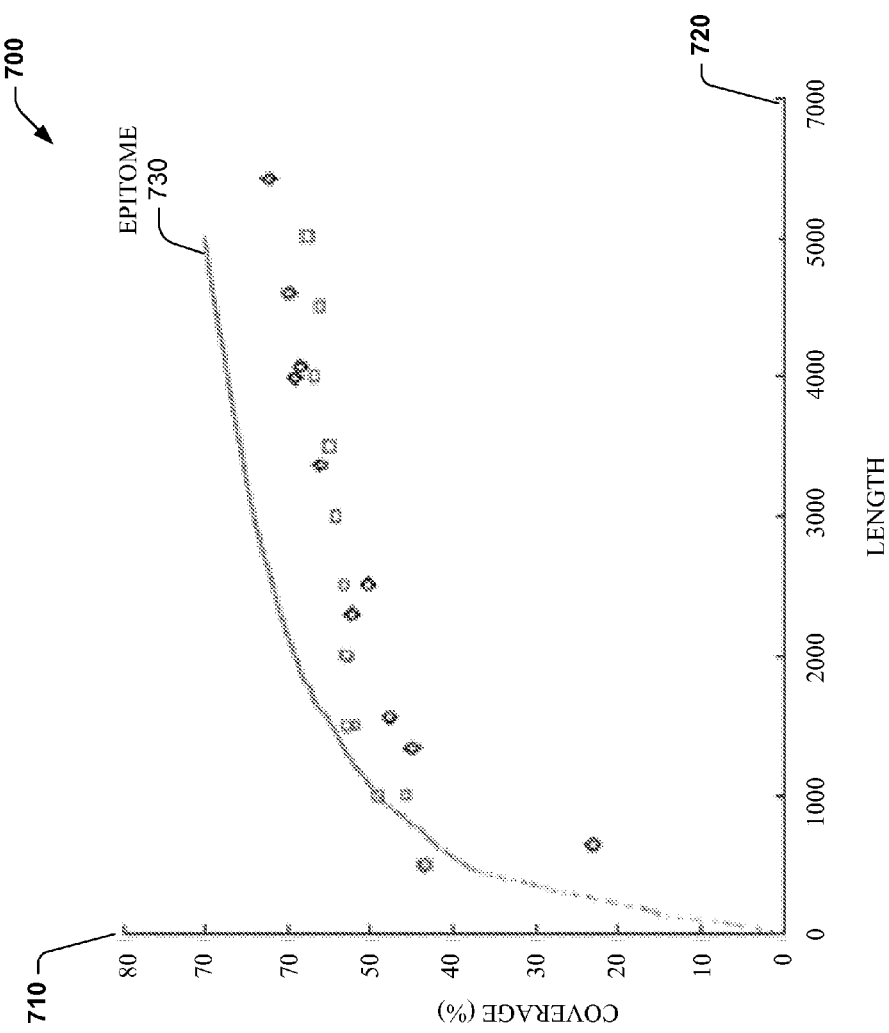
FIG. 7 is a graph depicting epitope coverage versus length.
Figure 8:
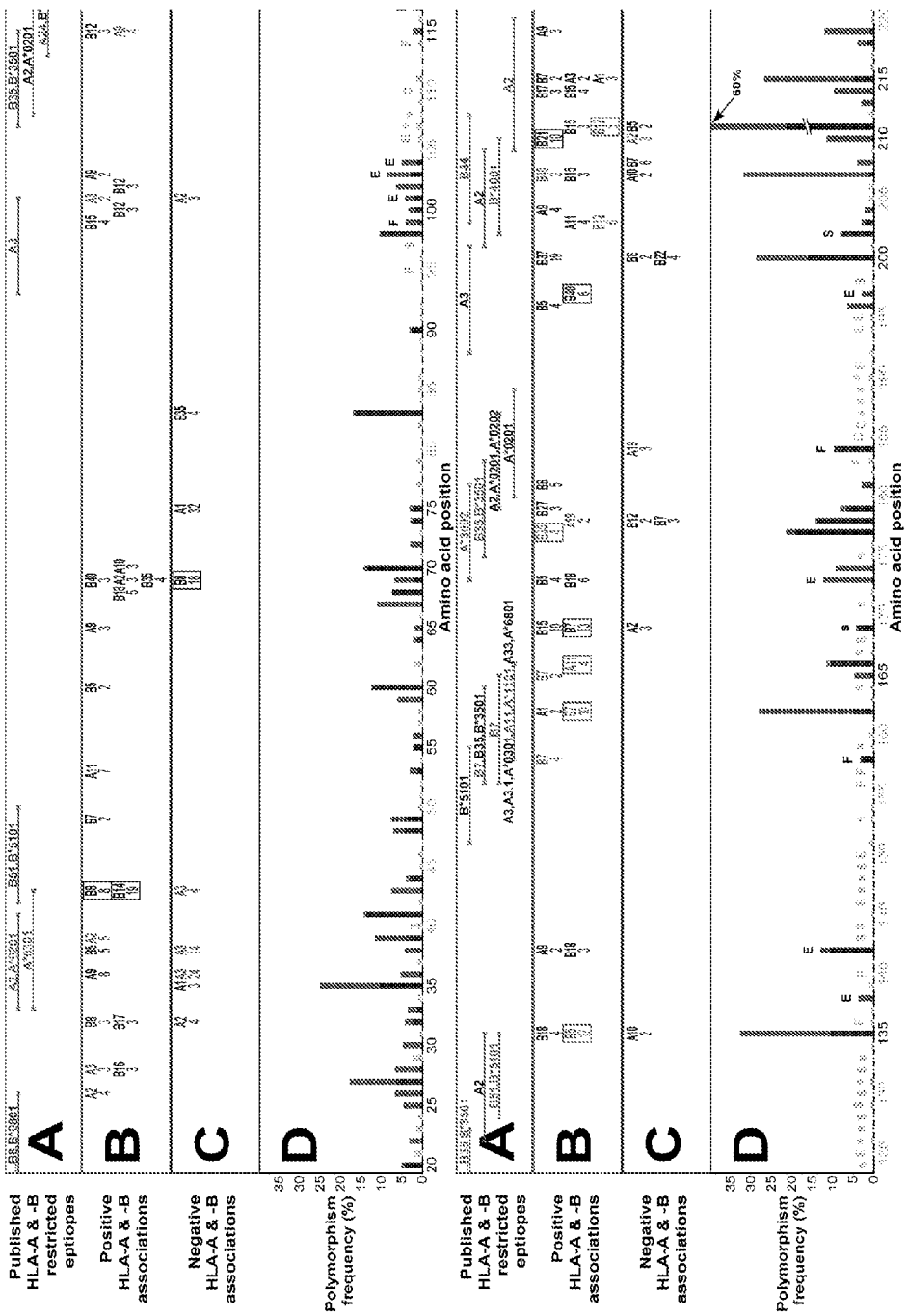
FIG. 8 is a map of polymorphism rate at amino acid positions 20-227 of HIV-1 RT and associations with HLA-A and HLA-B alleles. The known HLA-A and HLA-B restricted cytotoxic T-lymphocyte (CTL) epitopes (B. T. M. Korber et al., HIV Molecular Immunology Database 1999 (Theoretical Biology and Biophysics, New Mexico, 1999)) are marked as grey lines in Box A. Box D shows the percentage of patients with a different amino acid to that in the population consensus sequence at each position in most recent HIV-1 RT sequence (n=473). The HLA alleles that are significantly associated with polymorphism are shown above the polymorphic residue in Box B, along with the odds ratio (OR) for the association. The 15 HLA-specific polymorphisms within the 29 known CTL epitopes restricted to the same broad HLA allele are in grey text and the five at flanking residues are in black text. Clustered associations in black text may be within new or putative CTL epitopes. The boxed associations are those that remain significant after correction for total number of residues examined as described in the text. HLA-B*5101 is a subtype of HLA-B5, HLA-B44 is a subtype of HLA-B12 and HLA-A24 is a subtype of HLA-A9. In Box C, negative HLA associations are marked with ORs expressed as the inverse (1/OR), giving a value >1 for odds of not being different to consensus. These are also in grey or black text if within or flanking known CTL epitopes. The known functional characteristics of residues are marked as stability (S), functional (F), catalytic (C) and external (E) adjacent to the residue.
Figure 9:
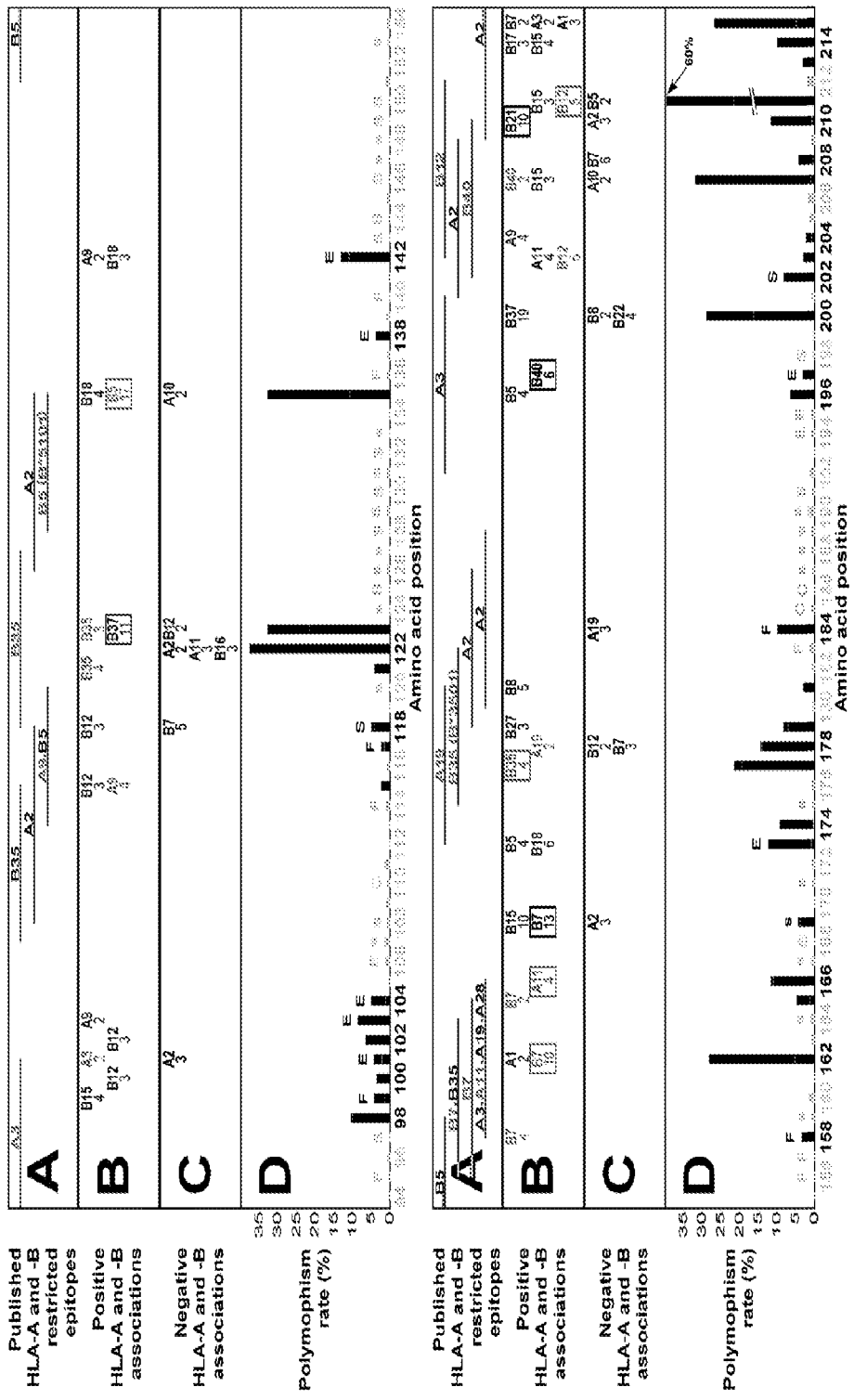
FIG. 9 is a map of polymorphism rate at amino acid positions 95-202 of HIV-1 reverse transcriptase (RT) and known amino acid functional characteristics. The map of amino acid positions 95-202 of HIV-1 RT shows the percentage of patients with change from population consensus amino acid at each position in pre-antiretroviral treatment HIV-1 RT sequences (n=185). Both conservative (grey bars) or non-conservative (solid black bars) amino acid substitutions are shown.
Figure 11A:
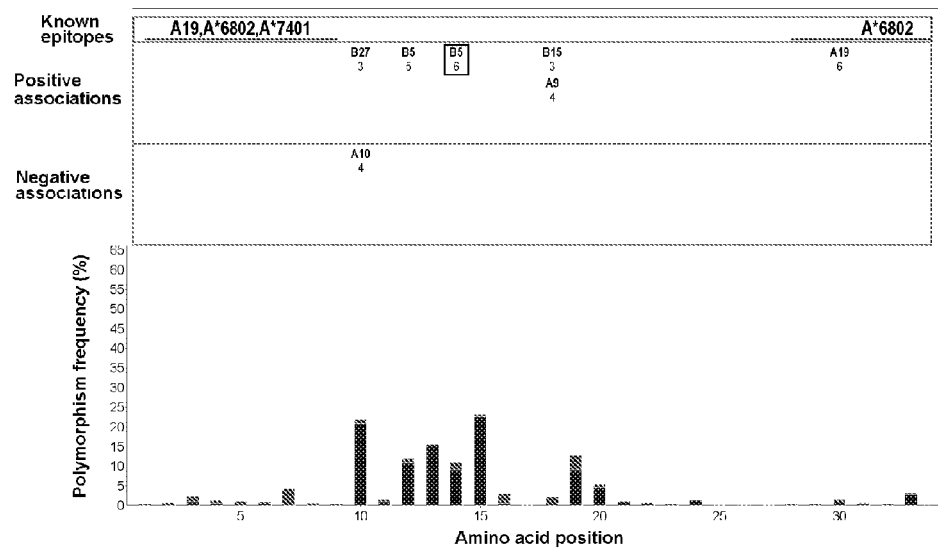
FIG. 11 is a map of polymorphism rate at amino acid positions 1-90 of HIV-1 protease and associations with HLA-A and HLA-B alleles. The known HLA-A and HLA-B restricted CTL epitopes are marked as grey lines in the top box. The bottom box shows the percentage of patients with a different amino acid to that in the population consensus sequence at each position in most recent HIV-1 protease sequence (n=493). The HLA alleles that are significantly associated with polymorphism are shown above the polymorphic residue along with the odds ratio (OR) for the association. The HLA-specific polymorphisms within the known CTL epitopes restricted to the same broad HLA allele are in grey text and the five at flanking residues are in black text. Clustered associations in black text may be within new or putative CTL epitopes. The boxed associations are those that remain significant after correction for total number of residues examined as described in the text. Negative HLA associations are marked with ORs expressed as the inverse (1/OR), giving a value >1 for odds of not being different to consensus. These are also in grey or black text if within or flanking known CTL epitopes.
Figure 11B:
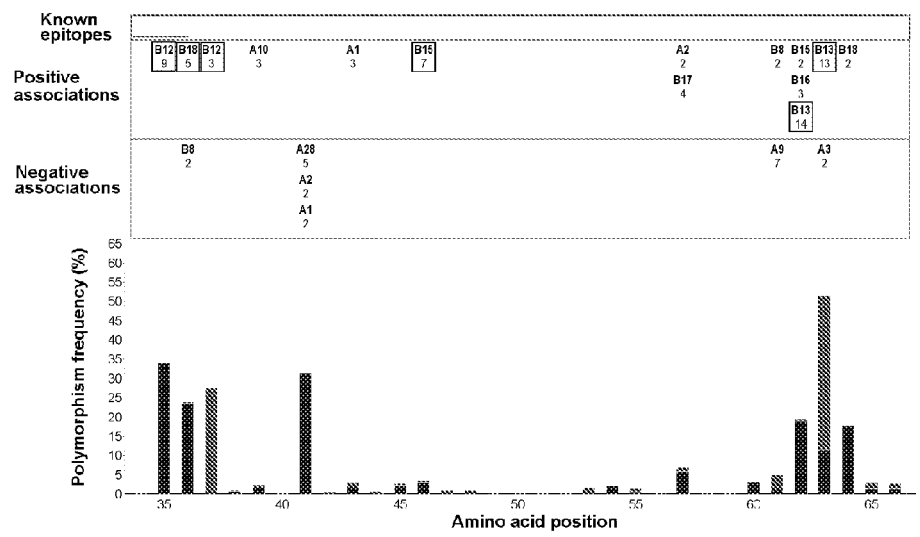
Figure 11C:
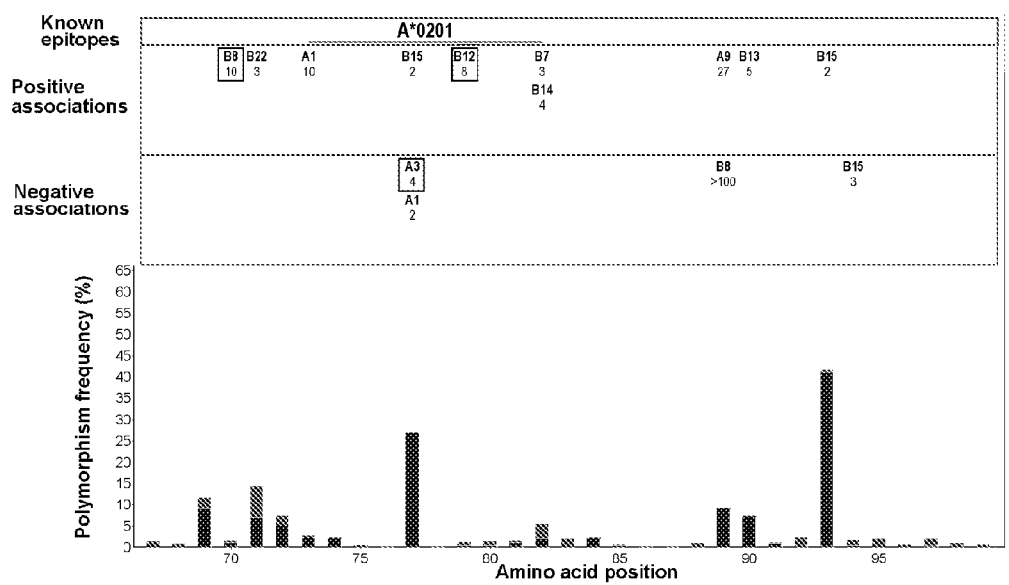

FIG. 5 illustrates an exemplary epitome 500 and a plurality of patches (sequences) 510 that the epitome 500 epitomizes in terms of linear nine-amino acid epitopes, assuming that all nine-mers are equally immunogenic and exposure to the immune system leads to no cross-reactivity. Although nine-mers are depicted, it is to be appreciated that essentially any mer (e.g., ten-mers, eleven-mers, etc.) can be utilized in various aspects of the subject invention, and any or all assumptions can be relaxed. As illustrated at 520, 530, 540 and 550, three portions of the epitome 500 can be matched with various portions of the plurality of sequences. Such matching can be achieved by moving a window (e.g., nine-long, as depicted in FIG. 5) over the epitome, for example, from left to right. While moving the windowing, the window can be matched with a corresponding sequence epitopes. The epitome 500 can be estimated from the data by chopping up the input sequences 510 into short peptides of epitope length or longer and creating a mosaic sequence longer than any given data sequence, but much shorter than the sum of all input sequence lengths. It is to be appreciated that even though it may be desirable to achieve coverage of short epitopes, due to the overlaps in these epitopes in the data, the epitome may favor conservation of long amino acid stretches from the epitomized sequences. Therefore, the epitome can also be viewed as a collection of longer or shorter protein pieces needed to compose each of the given sequences.

FIG. 6 depicts a graph 600 that illustrates epitome coverage of a plurality of different CAG genes over length, and FIG. 7 depicts a graph 700 that illustrates epitome coverage of various epitopes of a GAG gene over length. In these figures, respective axes 610 and 710 correspond to coverage as a function of percent and respective axes 620 and 720 corresponds to length. In this example, epitomes of size 1×Ne can be utilized. However, as a vaccine the epitome may need to be delivered in a different format, which can be achieved by chopping the 1×Ne epitome into smaller pieces or directly optimizing an epitome of a required format as described herein. The patches derived from the sequence data can include all possible contiguous amino acid subsequences, for example, of size nine, corresponding to the length of a typical epitope, with indices S=11, 12, . . . , 19. In order to include a context that can affect escape, the patches may need to be longer. However, optimizing for coverage of shorter patches can lead to preservation of a larger context around any or all patches due to patch overlaps both in data and in the epitome. To compute various vaccine components, an expectation-maximization (EM) algorithm, a greedy algorithm, and the like can be utilized to train a mixture of profile sequences, for example, sequences in which each site has an associated most likely letter and a probability of generating any other letter.

Epitomes of various sizes can be utilized, wherein such epitomes can be constructed by iteratively increasing the size of the epitome and decreasing the free energy with the assumption $\theta=0$, thus increasing coverage of the epitopes from the data. Respective acts can be optimal incremental moves, for example, by adding a most frequent data patch that is not yet included in the epitome. This optimization follows a conservative assumption that none of the epitopes in the sampled viruses should be apriori ignored in an effective vaccine (e.g., p(S)=const) and only an exact copy of epitope in the vaccine will lead to an effective vaccine ($\theta=0$). Thus, the efficiency of the optimization algorithms can be evaluated by a percentage of the data patches that are exactly copied in the epitome. As discussed previously, coverage is related to the free energy and can be more intuitive when $\theta=0$.

FIGS. 8-15 show the results of techniques for obtaining data at the population level and for the development of therapeutics in the context of HIV-1 proteins, such as HIV-1 reverse transcriptase (RT) (which is highly expressed in virions and immunogenic in the early response to HIV-1). HIV-1 RT may be substituted for another suitable HIV protein or the sequences selected for examination may be derived from another virus or organism.

The Western Australian (WA) Cohort Study was established in 1983 as a prospective observational cohort study of HIV infected patients. From 1983 to 1998, the study captured data from 80% of all HIV-infected cases and all notified AIDS cases in the state of Western Australia. Comprehensive demographic and clinical data was and is collected at outpatient and in-patient visits by medical staff and entered into an electronic database. Start and stop dates of all antiretroviral treatments are recorded. Routine laboratory test results are automatically downloaded from the laboratory directly into the cohort database. Data from a maximum of 473 cohort subjects with HLA and viral sequence data were analyzed in logistic regression models.

The vast majority of patients in the cohort reside in or near the capital of Western Australia, Perth, which is one of the most geographically isolated cities in the world. New HIV-1 infections are most frequently acquired from sources within Western Australia (53.3%) or other states in Australia (24.3%), and less commonly from Asia (8.2%), Africa (5.1%), Europe (4.9%), North America (3.4%) or South America (0.8%). Participants have certain demographic, clinical and laboratory data collected routinely, including HLA class I serological typing and HLA class II sequence based typing. HIV-1 RT proviral DNA sequencing is performed at first presentation (prior to any antiretroviral treatment in 185 cases) and serially while on RT inhibitor therapy. This study encompasses data collected over approximately 2210 patient-years of observation.

Relationships between HIV-1 RT sequences in 473 participants of the Western Australian (WA) HIV Cohort Study and their HLA-A, -B and -DRB1 genotypes were examined. The HLA-A and -B alleles present in individuals included A1, A2, A3, A9, A10, A11, A19, A28, A31, A36, B5, B7, B8, B12, B13, B14, B15, B16, B17, B18, B21, B22, B27, B35, B37, B40, B41, B42, B55, B56, B58, B60 and B61.

All HLA-A and HLA-B broad alleles were typed by microcytotoxicity assay using standard NIH technique. For this study, 51 HLA-B5 individuals and 57 HLA-B35 individuals had HLA-B sequence amplified using primers to the first intronic dimorphism as previously described (see for example N. Cereb and S. Y. Yang, *Tissue Antigens* 50, 74-76 (1997)) and products were sequenced by automated sequencing. HLA-DRB1 alleles were typed by sequencing using previously reported methods (see for example, D. Sayer et al., *Tissue Antigens* 57, 46-54 (2001)).

HIV-1 DNA was extracted from buffy coats (QIAMP DNA blood mini kit; Qiagen, Hilden, Germany) and codons 20 to 227 of RT were amplified by polymerase chain reaction. A nested second round PCR was done and the PCR product was purified with Bresatec purification columns and sequenced in both forward and reverse directions with a 373 ABI DNA Sequencer. Raw sequence was manually edited using software packages Factura and MT Navigator (PE Biosystems).

The viral load assay used until November 1999 was the HIV Amplicor™ (Roche, Branchburg, USA, lower limit of detection 400 copies/mL). The Roche Amplicor HIV monitor Version 1.5, Ultrasensitive, lower limit of detection 50 copies/mL was used thereafter. Viral load assays were routinely performed at least three monthly in all patients.

Using the WA HIV Cohort Study database to facilitate analyses based on Fisher's exact tests and logistic regression models standard formulae were used for power calculations (see for example J. H. Zar, in *Biostatistical Analysis*, Bette Kurtz, Ed. (Prentice-Hall International, New Jersey, 1984) chap. 22.11). Individual covariates were assessed separately for association with polymorphism at the amino acid position under consideration using Fisher's exact test, and only those with univariate P-values$\leqq$0.1 were included in further analyses. If the number of covariates selected by this method exceeded 10% of the patient numbers a forward stepwise procedure based on standard logistic regression was used to reduce the number to 10% and standard backwards elimination used until all covariates had a P-value$\leqq$0.1. For example, covariates were assessed separately for association with I135 using Fishers exact test, and only those with univariate P-values$\leqq$0.1 were included in further analyses. The removed alleles were A1, A2, A3, A9, A11, A19, A28, B7, B8, B13, B14, B15, B16, B21, B22, B27 and B35.

Since the number of covariates selected at position I135 was less than 10% of the number of patients, no forward selection was needed. A standard backwards elimination was then carried out at position I135. The covariant with the largest P-value was removed and the logistic model refitted. This was repeated until all covariates had a P-value less than 0.1, thus removing HLA alleles B12, B17 and B40.

To accommodate relatively small samples in some of the logistic regressions, exact P-values were based on randomization tests rather than the usual large sample approximations (see for example F. L. Ramsey and D. W. Schafer, in *The statistical sleuth. A course in methods of data analysis*, (Duxbury Press, 1997), chap. 2). In this procedure covariate sets were randomly permuted amongst the patients and the standard test values for association with polymorphism calculated for each permutation. This procedure generated 1000 random permutations for each model and based the P-value on the appropriate percentage of test values more extreme than that pertaining to the actual data. P-values$\leq$0.05 were considered to be significant using this method. For example, at position I135, alleles HLA-A10 and -B18 were removed, leaving HLA-B5 as the significant association with I135.

Analyses were conducted to determine the probability of finding by chance at least fifteen significant positive associations within corresponding known cytotoxic T lymphocytes (CTL) epitopes. If significant associations were occurring randomly across residues, the probability that an HLA association would occur within the known CTL epitope restricted to that allele equates to the relative proportion of all residues falling within the epitope. The total number of significant associations within known epitopes is then a sum of non-identical binomial variables, whose distribution can be evaluated via simulation, for example. Only 4.27 significant positive associations within known epitopes were expected based on the random hypothesis compared with the 15 observed (approximate P-value <0.001).

Correction factors for multiple comparisons were generated as described later and corrected exact P-values were determined by the function: $1-(1-P)^x$ where x=correction factor. The overall P-value for all associations at all positions was obtained by considering the extremeness of the sum of the individual tests at each position relative to the values of this sum obtained from the randomization data sets. For the Cox proportional hazards models of viral load, HLA associations had to have at least four individuals representing HLA allele versus non-HLA allele, with polymorphisms and without to be included (n=106). The viral load measured closest to first pre-treatment HIV-1 RT sequencing was used.

To determine whether polymorphisms in HIV-1 RT sequences in the study population were distributed randomly or occurred at preferred sites, the population consensus sequence was used as a reference sequence and was determined by assigning the most common amino acid at each position from 20 to 227 (numbering system as in reference B. T. M. Korber et al., HIV Molecular Immunology Database 1999 (Theoretical Biology and Biophysics, New Mexico, 1999)) of all first HIV-1 RT amino acid sequences prior to any antiretroviral therapy (n=185). This population consensus sequence matched the lade B reference sequence HIV-1 HXB2 (L. Ratner et al., *Nature* 313, 277-284 (1985)) at all positions in RT except 122 (lysine instead of glutamate) and 214 (phenylalanine instead of leucine). The percentages of patients with a different amino acid in their own first pre-treatment HIV-1 RT sequence compared to that of consensus sequence were calculated for each residue. The relationship between this polymorphism rate and the functional characteristics (stability, functional, catalytic or external) known for amino acids between positions 95 to 202 in HIV-1 RT was examined.

The rate of polymorphism at single residues was highly variable, ranging from 0% to 60% and appeared to correlate with the expected viral tolerability of change at that site. For example, the polymorphism rates at the three critical catalytic residues in HIV-1 RT (0.53%), stability residues (n=37, 1.06%) and functional residues (n=11, 3.05%) were lower than at external residues (n=10, 5.95%) (P=0.0009, Wilcoxon).

As antigen specific CTL responses are HLA class I restricted, polymorphisms in HIV-1 RT that were the result of CTL escape mutation were examined to determine whether they would be HLA class I allele-specific across the population and would be in residues within or proximate to CTL epitopes. The relationship between HLA-A and HLA-B broad alleles (as explanatory covariates) and polymorphism in HIV-1 RT (as the outcome or response variable) in multivariate logistic regression models was therefore examined. The most recent HIV-1 RT sequence in each patient was used in these analyses (n=473). Single amino acid residues in HIV-1 RT were examined in separate models. An individual model at one residue determined the statistical significance of association(s) between the covariates (HLA alleles) and the outcome (polymorphism at that residue only) and gave odds ratios (ORs) for associations.

The statistical power to detect the effect of any individual HLA allele in these models depended on the frequency of the allele in the population and the frequency of polymorphism at the amino acid position being examined. An initial power calculation was performed for each position to determine for which alleles there was a reasonable power to detect an association if it existed (at least 30% power to detect an OR>2.0 or <0.5). Only those HLA alleles that had a univariate association with polymorphism with $P\leq0.1$ were examined at each viral residue (one to ten HLA alleles, mean 3.15 at 72 positions) in subsequent analyses. Final covariates in the logistic regression models also withstood a standard forward selection and backwards elimination procedure. Permutation tests based on the logistic models were used to determine the exact P-values for associations (F. L. Ramsey and D. W. Schafer, in *The statistical sleuth. A course in methods of data analysis*, (Duxbury Press, 1997), chapter 2).

HLA alleles with less than 30% power were removed. The removed alleles at position 135 were A31, A36, B42, B55, B56, B58 and B61. It is important to note that there was less power to detect negative associations than positive associations. For example, at the mean HLA frequency of 10.9 and mean polymorphism rate of 4.0%, there was 30% power to detect an OR of 2.0 (i.e. a positive association) but only 5.6% power to detect an equivalent negative OR of 0.5.

The results of all the individual models were plotted together on a map of HIV-1 RT amino acid sequence from position 20 to 227. There were 64 positive associations (i.e., OR>1) between polymorphisms of single residues in HIV-1 RT and specific HLA-A or -B alleles ($P\leq0.05$ in all cases). Polymorphisms specific for a particular HLA allele clustered along the sequence. For example, HLA-B7 was associated with polymorphism at positions 158 (OR=4), 162 (OR=10), 165 (OR=2) and 169 (OR=13), which are all within or flanking the known HLA-B7 restricted CTL epitope RT(156-165) (C. M. Hay et al., *J Virol* 73, 5509-5519 (1999); L. Menendez-Arias, A. Mas, E. Domingo, *Viral Immunol* 11, 167-181 (1998); C. Brander and B. D. Walker, in *HIV molecular immunology database*, B. T. M. Korber et al., Eds. New Mexico, (1997)). There was also clustering of associations for HLA-B12 (at positions 100 and 102, 115 and 118, 203 and 211), HLA-B35 (121 and 123), HLA-B18 (at 135 and 142), and HLA-B15 (at 207, 211 and 214).

Fifteen HLA class I allele-associated polymorphisms occurred at residues within the 29 CTL epitopes that are characterized, published and known to be restricted to those alleles. Four of these residues (101, 135, 165 and 166) were at primary anchor positions within CTL epitopes (HLA-A3 (C. Brander and P. J. R. Goulder, in *HIV Molecular Immunology 2000*, B. T. M. Korber et al., Eds. (Theoretical Biology and Biophysics, New Mexico, 2000) chap. Part 1. Review Articles), HLA-B51 (L. Menendez-Arias, A. Mas, E. Domingo, *Viral Immunol* 11, 167-181 (1998); N. V. Sipsas et al., *J Clin Invest* 99, 752-762 (1997))/HLA-B*5101 (H. Tomiyama et al., *Hum Immunol* 60, 177-186 (1999)), HLA-B7 (C. M. Hay et al., *J Virol* 73, 5509-5519 (1999); L. Menendez-Arias, A. Mas, E. Domingo, *Viral Immunol* 11, 167-181 (1998); C. Brander and B. D. Walker, in *HIV molecular immunology database*, B. T. M. Korber et al., Eds. New Mexico, (1997)) and HLA-A11 (Q. J. Zhang, R. Gavioli, G. Klein, M. G. Masucci, *Proc Natl. Acad. Sci U.S.A* 90, 2217-2221 (1993)) restricted respectively) where mutation could abrogate binding to the HLA molecule. The remaining 11 associations were at non-primary anchor positions of published CTL epitopes. There were a further five HLA allele-specific polymorphic residues that flanked CTL epitopes restricted to the same HLA alleles. The residues at positions 26 and 28 that flank known HLA-A2 and HLA-A3 restricted epitopes were predicted proteosome cleavage sites (C. Kuttler et al., *J Mol Biol* 298, 417-429 (2000)). If significant positive associations occurred randomly across residues only 4.18 would have been expected to fall within corresponding known CTL epitopes. The observed number of 15 was significantly higher than this ($P<0.0004$). Furthermore, an excess of associations over that expected was seen for ten of the 11 HLA specificities with epitopes in this segment of HIV-1 RT.

A final set of analyses was conducted to identify which of these significant HLA associations would remain significant after a correction for the effective number of independent comparisons made over the entire analysis. HLA genotypes were randomly reassigned amongst individuals and the previously described analysis was run 1000 times to determine the number of false positive associations expected by chance alone for each HLA allele. The average number of P-values $\leq 0.05$ obtained was multiplied by 20 (i.e., 1/0.05) to estimate the effective number of independent tests carried out as a correction factor for multiple comparisons for each HLA allele. Correction factors ranged from 5.0 (HLA-B37) to 92.2 (HLA-B7) for positive associations and 0.8 to 42.8 for negative associations. There were 14 associations that still had a $P \leq 0.05$ following this correction.

The randomization data sets were also used to generate an overall test of significance, taking multiple comparisons into account, of all HLA associations at all positions across all models. This test had a P-value of <0.001.

Molecular HLA sub-typing can increase strength of association between polymorphism and HLA alleles. Serologically defined HLA class I alleles have subtypes, defined by high resolution DNA sequence based typing, that have amino acid sequence differences in the peptide binding regions that influence epitope binding. For these alleles, it would be expected that CTL escape mutation would be more closely associated with the molecular subtype than with the broad HLA allele.

As examples, two strong associations with broad HLA alleles with well-represented splits, at sites within known CTL epitopes, and where the HLA restriction of the epitope at the molecular level was known were examined. Polymorphism at position 135 (I135x, where I is the consensus amino acid isoleucine and x is any other amino acid) associated with presence of HLA-B5 was the strongest positive HLA association at a residue within a published epitope (OR=17, P<0.001). D177x, within an epitope specifically restricted to the HLA-B*3501, was associated with HLA-B35 (OR=4, P<0.001).

Isoleucine is the amino acid at position 135 of the consensus HIV-1 RT sequence. It is the eighth amino acid and anchor residue of a known 8mer HLA-B5 (*5101) restricted CTL epitope, RT(128-135 IIIB). Six of the other seven amino acid residues of the epitope are critical stability residues for the RT protein and are relatively invariant in the cohort. Of all 52 HLA-B5 positive patients, 44 (85%) had a substitution of isoleucine at position 135. Of the 421 non-HLA-B5 individuals, only 123 (29%) had this change (P<0.0001, Fisher's exact test).

DNA sequencing to subtype all 52 individuals in the cohort with the HLA-B5 allele was undertaken. One HLA-B5 patient did not have sufficient DNA sample to perform high resolution HLA typing. Forty of the remaining 51 HLA-B5 patients were of the HLA-B*5101 subtype. All but one of these 40 HLA-B*5101 patients (98%) had I135x (I135T in 25 cases, I135V in 5 cases, I135L/M/R or mixed species in the remaining 9 cases). In contrast, only 127 of the 432 (29%) non-HLA-B*5101 patients in the cohort had I135x (P<0.0001, Fisher's exact test). For the most common substitution, from isoleucine to threonine, the predicted half time of dissociation score for the mutant epitope (TAFTIPST) is 11 compared with 440 for the consensus sequence (TAFTIPSI), indicating that binding to the HLA molecule in vivo is abrogated. This substitution has been shown to necessitate a hundred-fold increase in the peptide concentration required to sensitize target cells for 50% lysis ($SD_{50}$) by CTLs in vitro (N. V. Sipsas et al., *J Clin Invest* 99, 752-762 (1997)). The less common isoleucine to valine substitution at position 135 has been associated with a ten-fold increase in $SD_{50}$ compared with consensus epitope (N. V. Sipsas et al., *J Clin Invest* 99, 752-762 (1997)).

The single HLA-B*5101 patient who was not different to consensus at position 135 was a patient who had highly active antiretroviral therapy (HAART) administered during acute HIV seroconversion. The patient had presented within days of virus transmission with plasma HIV RNA concentration (viral load) of 6.5 log copies/mL and a negative HIV antibody test. He had no symptoms of seroconversion illness. After HAART was started, viral load progressively decreased to undetectable levels over the next six months, and has remained undetectable on treatment for a further ten months until the present time.

The one patient with the HLA-B*5108 subtype, and four of eight patients with the HLA-B*5201 subtype did not have I135x, suggesting that these subtypes may not bind the RT(128-135 IIIB) epitope. Both subtypes differ from HLA-B*5101 by only two amino acids (HLA-B*5108 at positions 152 and 156, HLA-B*5201 at positions 63 and 67, of HLA amino acid sequence) (IMGT/HLA sequence database; www.ebi.ac.uk/imgt/hla). The remaining two patients were shown to be HLA-B*5301 by sequencing.

The HLA-B35 subtype HLA-B*3501 only differs from HLA-B*3502, -B*3503, -B*3504 by one or two amino acids in the peptide binding region and yet the different epitope specificities of these subtypes have a striking effect on risk of clinical progression of HIV-I infection. The epitope RT(175-183) binds to HLAB*3501 and contains a binding motif that is distinct to that predicted for other HLAB35 subtypes (www.uni-teubingen.de/uni/kxi/). Of 57 HLA-B35 positive individuals in the study population, 26 (46%) had D 177x compared with 84 of 416 (20%) non-HLA-B35 individuals (P<0.0001, Fisher's exact test). However, there were 19 of 33 (58%) HLA-B*3501 patients that had D177x compared with 86 of the 440 (20%) non-HLA-B*3501 patients (P<0.0001, Fisher's exact test). Thus, the univariate relative risk of polymorphism increased from 2.7 to 4.7 after the molecular subtype of HLA-B35 was considered. This analysis was repeated for other HLA-B35 associated polymorphisms in HIV-I RT, I69x, D121x and D123x and in all cases, the association was strengthened by considering molecular subtypes of HLA-B35.

To determine whether selection of HLA-specific polymorphisms over time was demonstrable, the amount of HLA-specific variation present in the most recent HIV-1 RT sequence with the first sequence for all individuals was examined. For 61 of 64 HLA-specific polymorphisms, the number of individuals with a specific amino acid polymorphism increased over time and under observation. In 52 of these cases, the increase was significantly greater in those with the HLA allele associated with the polymorphism, compared with all others without the allele (P=0.0008, sign test) as shown in Table 1.

TABLE 1

| Polymorphism | Number (n) | P-value (sign test) |
|---|---|---|
| HLA-specific polymorphisms | 64 | P < 0.0001 |
| HLA-specific polymorphisms that increase from first to last HIV-1 RT sequences | 61 | P < 0.0001 |
| HLA-specific polymorphisms that increase from first to last HIV-1 RT sequences in those with the corresponding allele compared with all others | 52 | P < 0.0001 |

Primary CTL escape mutation in an HIV-1 p24 epitope has been shown to induce possible compensatory mutations in the virus. To determine whether the secondary or compensatory changes accompanying primary (putative) CTL escape mutation were evident at a population level, polymorphisms were included at all 'other' positions in HIV-1 RT, along with HLA alleles, as covariates in all multivariate logistic regression models. All but two of the 64 positive HLA-specific polymorphisms were also associated with one or more polymorphisms at other positions.

In the multiple logistic regression models described earlier, there were 25 residues at which polymorphism was HLA-specific but with an OR<1, indicating a 'negative' association. For example, change from consensus amino acid at positions 32, 101, 122, 169, and 210 of HIV-1 RT was negatively associated with presence of HLA-A2 ($P \leq 0.05$ in all cases). This means that HLA-A2 individuals were significantly less likely to vary from the consensus at these sites compared with all non-HLA-A2 individuals in the cohort. The negative ORs were inversed (1/OR) to give a value >1 for the odds of not having a polymorphism. HLA-A2 is the most common HLA-A allele in our cohort and had five of the 25 negative associations (compared with three of the 64 positive associations).

Similarly, individuals with HLA-B7 were more likely to have the consensus amino acid at positions 118, 178 and 208 compared with non-HLA-B7 individuals. According to this analysis there was less power to detect negative associations than positive associations. For example, at the mean HLA frequency of 10.9 and mean polymorphism rate of 4.0%, there was 30% power to detect an OR of 2.0 (i.e. a positive association) but only 5.6% power to detect an equivalent negative OR of 0.5.

As HIV-1 viral load has been shown to be inversely proportional to HIV-specific CTL responses, studies were undertaken to determine whether the presence of putative CTL escape mutations was associated with increased viral load. Individual HLA-specific polymorphisms were selected for examination. A polymorphism at an anchor residue was considered. HLA-A11 associated K166x is at the anchor position of an HLA-A11 epitope RT(158-166 LAI) and HLA-A11 groups with and without the polymorphism had sufficient numbers for comparison. To exclude effects of antiretroviral therapy, only patients with HIV-1 RT sequence and viral load results prior to treatment were analyzed. The closest pre-treatment viral load measurement taken after the HIV-1 RT sequencing, was compared between all groups. In HLA-A11 individuals (n=19), the median pre-treatment viral load was 5.54±0.46 log cps/mL plasma (median±SD) in those with K166x (n=4) compared with 4.31±0.82 log cps/mL, in those without K166x (n=15, P=0.045, Wilcoxon). Median viral load in HLA-A11 individuals without K166x was not significantly different from that of all non-HLA-A11 individuals (data not shown).

A second putative CTL escape mutation within a CTL epitope but not at a primary anchor position showed a similar effect. The median pre-treatment viral load in HLA-B7 patients with S162x (n=18) was significantly higher (5.41±1.04 log cps/mL) than in those without S162x (n=15, 4.57±0.83 log cps/mL, P=0.046, Wilcoxon). For both HLA-A11 and HLA-B7 groups, the mean CD4 T cell count and percentage of individuals with AIDS at baseline was not significantly different between those with and those without these putative CTL escape mutations.

A global analysis of factors influencing viral load at a population level was then conducted. A Cox proportional hazards model was carried out in which pre-treatment viral load was the outcome and all HLA alleles and HLA-specific polymorphisms were discrete covariates. When HLA alleles and polymorphisms were included as interaction terms (i.e. a polymorphism and it's positively associated HLA allele, or consensus amino acid and the negatively associated HLA allele) the overall significance value of the model improved. The former model had a log likelihood of −32.0765 with 40 degrees of freedom and the latter model had a log likelihood of −15.4165 with 25 degrees of freedom. The improvement in the model was calculated using a chi square distribution with a value of two times the difference in log likelihood values with degrees of freedom (33.32~$\chi(15)$), giving a P-value of 0.004). This suggested that the presence in individuals of viral CTL escape mutations as putatively identified in these analyses, explained the viral load variability in the population to a greater extent than either HLA alleles or viral polymorphisms per se.

Logistic regression models of polymorphism incorporating HLA-DRB1 broad alleles as covariates along with HLA-A and -B alleles and polymorphisms at other positions were repeated. Only patients in the cohort with DRB1 alleles defined by DNA sequence based typing were included in this analysis (n=294). There were 13 sites of polymorphism between positions 20 and 227 that were significantly associated with HLA-DRB1 alleles. Only five T helper cell epitopes have been mapped within this segment of HIV-1 RT (A. S. de Groot et al., *J of Infectious Diseases* 164, 1058-1065 (1991); S. H. van der Burg et al., *J Immunol* 162, 152-160 (1999); F. Manca et al., *J of Acq. Imm. Def Syn. & Hum. R* 9, 227-237 (1995); F. Manca et al., *Eur J Immunol* 25, 1217-1223 (1995)) and only one, RT(171-190), has been assigned HLA-DRB1 allele(s) specificity (S. H. van der Burg et al., *J Immunol* 162, 152-160 (1999)). Four of the five known CD4 T helper cell epitopes encompassed sites of HLA-DRB1 allele-specific polymorphism found in the models described herein. These analyses did not detect an HLA-DRB1 association within RT(171-190). There were 10 HLA-DRB1 associated polymorphisms that were not within known T helper cell epitopes.

According to these analyses, HIV-1 RT sequence is relatively conserved among isolates however, even in a stable, geographically isolated population of HIV-1 infected persons there is sequence diversity of HIV-1 RT. The population consensus sequence was used in this study as the presumptive wild-type sequence best adapted to the population as a whole and was almost identical to the clade B reference sequence HXB2-RT. Yet, within the study population, variation from this consensus sequence was evident even in a segment of HIV-1 RT. Findings presented herein suggest that this diversity is the net result of at least two competing evolutionary pressures selecting for or against change at each amino acid. Foremost is the need to maintain functional integrity of the virus. Within the bounds of this fundamental constraint, a strong predictor of viral polymorphism appears to be host HLA.

There were 64, often clustered, polymorphisms in HIV-1 RT associated with specific HLA-A or HLA-B alleles. Polymorphisms occurred at sites that were within or proximate to published CTL epitopes, and correlated with the HLA alleles to which these epitopes are known to be restricted. This correlation was itself highly statistically significant and several associations still remained significant after rigorous correction for multiple comparisons across the whole analysis. The detailed features of specific examples, such as HLA-B*5101 associated I135x, were highly suggestive of CTL escape mutation affecting HLA-peptide binding. Polymorphisms at non-primary anchor residues of CTL epitopes, such as HLA-B*3501 associated D177x, HLA-B7 associated S162x and others may confer a survival advantage to the virus by disrupting T cell receptor-peptide recognition, epitope processing from precursor protein or by inducing antagonistic CTL responses. The five HLA-specific polymorphisms at residues flanking CTL epitopes may indicate viral escape by disruption of proteosome peptide cleavage. This form of escape has been particularly difficult to identify by standard techniques that use only the epitope peptide to measure CTL responses. HLA-specific polymorphisms increased over time, were associated with secondary changes at other positions and were predictive of viral load at a population level. The effect of single residue changes on viral load is especially striking given that there may be a polyclonal immune response against epitopes in other HIV-1 genes and other independent influences on viral load such as CCR5 polymorphism. Taken together, these data suggest that the HLA-specific polymorphisms identified herein in HIV-1 RT represent the net effects of in-vivo CTL escape mutation in individuals. By implication, those polymorphisms not within published CTL epitopes may indicate where new or putative CTL epitopes are located. The HLA associations that are very strong (with high OR), and which are clustered or remain significant after correction for multiple comparisons are those most likely to represent viral escape mutations in CTL epitopes that are yet to be defined.

CTL escape mutation has been well characterized in individuals with HLA-B8 (most commonly), HLA-B44, HLA-B27, HLA-AL 1 and HLA-A3, who may have been more escape-prone because of narrow range, oligoclonal CTL responses. These data suggest that CTL escape mutation is common and widespread, selected by responses restricted to a much wider range of HLA alleles than has been studied in individual cases. Though many HLA-specific polymorphisms increased over time in this study, some were present in first pre-treatment HIV-1 RT sequence and could reflect viral founder effects, have been variants selected at transmission or during the early CTL response of acute infection. The single HLA-B*5101 patient without I135x was distinguished by use of HAART in acute infection whilst highly viremic. This patient presented in the first days of infection with no symptoms, suggesting he had not yet mounted a CTL response. Presumably, the immune selection pressure was reduced or eliminated, arguing that I135x is selected during the acute CTL response, rather than selected at transmission or in chronic infection in HLA-B*5101 individuals. Protection from CTL escape variants may contribute to the effect of HAART in acute HIV infection leading to stronger chronic inhibitory CTL responses which, to date, has been largely attributed to preservation of HIV-1 specific CD4 T cell help.

HLA alleles were also associated with lack of polymorphism at certain residues, including at residues without functional constraint and these associations contributed independently in a comprehensive model of viral load. Unlike positive immune selection causing demonstrable escape over time in individuals, negative immune selection favors preservation of wild-type virus in vivo and so could only be evident at a population level. It is possible that consensus or wild-type virus is primordially adapted to the CTL responses that have most often been encountered (that is, those restricted to the most common or evolutionary conserved HLA alleles in the host population). For HIV-1, this may account, at least in part, for HIV-1 clade differences. Population adaptation could also explain why selection of escape polymorphisms in CTL epitopes restricted to the common allele HLA-A*0201 was not demonstrated in studies that have argued against an important role for immune escape and even why surprisingly few HLA-A2 and HLA-A1 restricted epitopes have been mapped in HIV-1. Furthermore, studies of HIV-1 exposed seronegative individuals suggest that CTL responses can alter viral infectivity and susceptibility to established primary HIV-1 infection. The HLA class I alleles associated with natural HIV-1 resistance or susceptibility appear to differ between racially distinct populations. To some extent this may reflect differences in the HLA alleles that are common in different populations and the degree to which a 'population-adapted' consensus virus can adapt to the individual.

Demonstration of 13 HLA-DRB1 specific polymorphisms in HIV-1-RT (adjusted for HLA-A and HLA-B associations and secondary polymorphisms) lend support to the possibility of CD4 T helper escape mutation in human HIV-1 infection. Relatively few T helper cell epitopes in HIV-1 RT are published and their HLA-class II restrictions are not defined, so it is difficult to assess whether these results are consistent with T helper selection of escape mutation. However, HLA class II restricted CD4 T helper responses have a central role in HIV-1 control and there are several reported associations between HLA class II alleles and HIV disease susceptibility and progression including after HAART.

The population-based approaches in this study reveal how both positive and negative selection forces compete at single residues to drive primordial and current viral evolution in vivo. These results are especially notable considering the factors that reduce the likelihood of observing significant HLA associations in such analyses. First, the power to detect associations is not constant for all HLA allele/viral residue combinations. Large numbers of individuals would be needed to observe any polymorphism at residues under immune pressure to mutate but with strong functional constraint, or any associations with HLA alleles that are rare. The use of formal power calculations identifies those HLA associations that cannot be excluded and would need larger data sets to be examined. Second, the molecular subtype of an HLA allele predicts its binding properties in vivo, as shown by the enhancement of associations between HLA-B5 and I135x, and HLA-B35 and D177x by high resolution HLA typing. Other alleles with multiple splits of similar frequency (e.g. HLA-A10 or HLA-A19) may have had associations that were not detected because only broad alleles were considered. Furthermore, molecular splits that have opposing effects at the same viral residue would negate any association with the broad allele. Finally, published epitopes are more likely to be in conserved regions, as studies tend to use laboratory reference strains as target antigens and conserved regions are more likely to have measurable immune responses in vivo. This approach, in contrast, preferentially detects putative immune epitopes in variable regions, making it complementary to standard epitope mapping methods. Insufficient patient numbers, lack of molecular based HLA typing and lack of known epitopes in conserved regions could all account for the immune epitopes in which 'expected' HLA-specific polymorphisms were not detected, and could mean that the strength (OR) of the demonstrated associations were underestimated in some cases.

The generation of chance associations as a result of comparisons made with multiple covariates (HLA alleles) and at multiple residues potentially hampers such analyses, though power calculations and other screening procedures considerably restrict the number of alleles and positions that are examined. The degree to which P-values generated within multivariate logistic regression models are corrected for the number of residues examined will then depend on the size of the gene(s) that has been arbitrarily chosen for study. With such correction, the approach will lose power to detect associations in direct proportion to the size of the gene region selected, decreasing false positive associations (higher specificity) but at the cost of losing true positive associations (lower sensitivity). These analyses of HIV-1 RT provided a gradation of P-values uncorrected for multiple comparisons, reflecting a gradation in strength of associations. Independent biological validation, rather than statistical means, will best determine what p-value cut-offs are optimal for either sensitivity or specificity. If correction is to be made (for high specificity) the randomization procedure undertaken allows the number of effective independent comparisons in the entire analysis to be estimated. Those HLA associations with P-values that withstand this rigorous correction have been highlighted by these methods. These highly robust associations represent the starting point to map new epitopes in HIV-1 RT.

In terms of the known associations between certain HLA and HIV-1 disease progression, HLA allele frequencies influence adaptation of 'wildtype' HIV-1 at a population level. However, in-vivo evolution proceeds within individuals of diverse HLA. This analysis shows that it is the presence of HLA alleles with their corresponding HLA-specific viral polymorphisms (or consensus) that is more predictive of viral load than the HLA alleles alone. It has also been suggested that it is the breadth of CTL responses that determines the risk of viral escape and hence, clinical progression. Narrow monospecific responses, as seen in HLA-B*5701 long term non-progressors, can be protective but may also increase risk of viral escape in individuals with the deleterious HLA allele, HLA-B8. Increasing heterozygosity of the three HLA class I loci, which would predict broader polyclonal responses, has been shown to predict slow progression to AIDS. Successful viral CTL escape mutation depends on having low functional barriers to mutation at the appropriate residues, so it may be the balance struck between the breadth of host epitope-specific CTL responses and viral functional constraint at those epitopes that is important. Hence narrow CTL responses could be protective if directed against conserved epitopes, but not protective or harmful if directed against epitopes susceptible to variation. The ability to map both the range of putative epitopes and the observed polymorphism of the epitope in a population for many HLA alleles at once is thus very useful. Future analyses of HIV-1 RT should also incorporate reverse transcriptase inhibitors as covariates in the models to examine the interaction between drug-induced primary or compensatory mutation and HLA-associated primary or secondary polymorphism. If immune pressures and antiretroviral drugs compete at sites within viral sequence, a greater or lesser tendency to drug resistance and response may be seen in patients depending on their HLA genotype.

Individualization of antiretroviral therapy may be improved if synergistic or antagonistic interactions between immune pressure and drug pressure are better understood. Just as these methods have identified the location of putative immune epitopes in HIV-1 RT, candidate epitopes in other HIV-1 proteins or proteins from other microorganisms could be screened for in the same way and then confirmed using standard assays of epitope-specific immune responses in vitro or in vivo. In HIV envelope, effects associated with anti-HIV antibody responses, CCR5 and CXCR4 genotype and any other polymorphisms of genes encoding products targeting envelope proteins can also be considered.

In other studies, HIV-1 protease was examined using the methods described above. In particular the method examined whether, in both HIV-1 RT and protease, host CTL pressure and drug pressure may compete or synergize at specific sites, which then influence drug resistance pathways in ways unique to the individual of given HLA type.

Bulk HIV-1 RT and protease pro-viral DNA sequences obtained from 550 individuals with HIV-1 infection were analyzed. Single amino acid positions were examined at a time. The consensus amino acid for each position was determined and compared against the amino acids present in each individual's autologous viral sequence at the corresponding position. A multivariate analysis for a single residue (for example, residue 184 of HIV-1 RT, methionine in consensus) was carried out in which the outcome of interest was the presence or absence of a specified polymorphism (M184V) or alternatively, any variation from consensus (M184x). The statistical significance of association(s) between this outcome and covariates such as the antiretroviral drugs used by the individuals and/or their HLA types, were then determined. Using model selection steps as previously described, this process was repeated for every residue making up the full HIV-1 RT and protease proteins.

The study population was drawn from The Western Australian (WA) HIV Cohort Study. Start and stop dates of all antiretroviral treatments are recorded. HLA-A and HLA-B genotyping has been routinely performed at first presentation since 1983. HIV-1 RT proviral DNA sequencing has been requested at first presentation (prior to treatment where possible) and during routine clinical management of antiretroviral therapy since 1995. HIV-1 protease sequencing was commenced in 1997. The total cohort in this study comprised 550 individuals. All had at least one HIV-1 RT sequence recorded and 419 individuals had protease sequence available for analysis.

All analyses were performed as described above. The population consensus sequence for HIV-1 RT(20-227) and protease (1-99), with standard HXB2 numbering and alignment, was used as the reference sequence in all analyses. The population consensus sequence matched the clade B reference sequence HIV-1 HXB2 at all positions in HIV-1 RT except 122 (lysine instead of glutamate) and 214 (phenylalanine instead of leucine). In HIV-1 protease, consensus sequence differed at position 37 (asparagine instead of serine) and 63 (proline instead of lysine).

Power calculations were conducted to limit analyses to only those positions, drugs and HLA alleles for which there was at least 30% power to detect associations with OR>2 (positive associations) or <0.5 (negative associations) with p-value<0.05. Individual covariates were then assessed for univariate association with mutation/substitution, and discarded if p-values were >0.1 and then subjected to forward selection and backwards elimination procedures. Exact p-values were determined for each association. Finally, a randomization or bootstrapping procedure was carried out to determine a correction factor for final (HLA) associations to adjust for multiple comparisons.

HIV-1 DNA was extracted from buffy coats (QIAMP DNA blood mini kit; Qiagen, Hilden, Germany) and codons 20 to 227 of RT were amplified by polymerase chain reaction. A nested second round PCR was done and the PCR product was purified with Bresatec purification columns and sequenced in both forward and reverse directions with a 373 ABI DNA Sequencer. Raw sequence was manually edited using software packages Factura and MT Navigator (PE Biosystems).

Only well characterized drug resistance mutations were selected for this examination. Among the 273 individuals in the cohort with pre-treatment HIV-1 RT sequences available, 12 (4.4%) contained HIV-1 RT primary and/or secondary mutations resistance mutations. Of 168 individuals with pre-treatment protease sequences available, 49 (29.2%) had protease primary resistance mutations. For those individuals with known seroconversion date (n=182), the mean time from seroconversion to time of first pre-treatment sequence was 5.7 years.

The pooled sequences of the whole cohort were then examined. 288 (52.4%) of these individuals had either past or current treatment with antiretroviral drugs, including NRTIs in 52.0%, NNRTIs in 8.2% and PIs in 16.4%. For each logistic regression model carried out for one position at a time, only the specific amino acid substitution characteristic of drug resistance was considered as the outcome. All sequential sequences for each individual were analyzed, spanning a mean period of 1.9 years per person. The earliest presence of a resistance mutation was recorded as a positive outcome, all subsequent sequences were discarded and all drug exposures prior to the outcome were entered as covariates. The outcome was recorded as negative if mutation had not developed in any sequence.

Primary and/or secondary drug resistance mutations were detected in 33.6% of subjects in post treatment HIV-1 RT sequences. The mutations detected with sufficient frequency to be examined in the logistic regression analyses included M41L, D67N, K70R, L74V, K103N, Y181C/I, M184V, G190A/S, L210W, T215Y and K219Q/E, whilst K65R, 75, V108I, Q151M and P225H were only rarely or not detected (<4.0% of sequences) and therefore had little power to be examined. For all the resistance mutations examined, the drug(s) associated with selection of the mutation at a population level corresponded to those known to select for the mutation from other studies (Table 2). For example, use of lamivudine was associated with the development of M184V with an OR of 19 (p<0.001). Use of zalcitabine independently increased risk of developing M184V (OR=3, p=0.004). Positive associations between L74V or M184V and use of abacavir were not detected in the study population. There was inadequate statistical power to detect associations between use of delavirdine and mutations as this agent was rarely used. Table 2—The amino acid substitutions in HIV-1 RT examined in models, with their published causative antiretroviral agent(s) and those associated with these substitutions at a population level in this study. OR-odds ratio, ZDV-zidovudine, ddI-didanosine, 3TC-lamivudine, d4T-stavudine, ABC-abacavir, NRTI-nucleoside analogue reverse transcriptase inhibitor, NNRTI-non-nucleoside analogue reverse transcriptase inhibitor.

| Amino acid substitutions examined in HIV-1 RT | Published primary drug association(s) | Drug association(s) detected at a population level in study cohort | OR | P-value |
| --- | --- | --- | --- | --- |
| M41L | thymidine NRTI | ZDV | 3 | <0.001 |
| D67N | ZDV? | ZDV | 10 | <0.001 |
| K70R | thymidine NRTI | ZDV | 2 | <0.001 |
| L74V | ddI ABC | ddI | 8 | <0.001 |
| K103N | NNRTI | nevirapine | 6 | <0.001 |
|  |  | efavirenz | 6 | <0.001 |
| Y181C/I | nevirapine delavirdine | nevirapine | 9 | <0.001 |
| M184V | 3TC | 3TC | 19 | <0.001 |
|  | ddC ABC | ddC | 3 | 0.004 |
| G190A/S | nevirapine | nevirapine | 11 | <0.001 |
| L210W | ZDV | ZDV | 2 | 0.016 |
| T215Y | thymidine NRTI | ZDV | 4 | <0.001 |
| K219Q/E | ZDV | ZDV | 4 | <0.001 |

There were primary protease inhibitor (PI) resistance mutations (D30N, M46I/L, G48V, V82A/T/F, L90M) detected in 24.1% and secondary PI resistance mutations (L10I, I54V/L, A71V/T, 73, V77I, 184V, N88S) in 30.3% of individuals with post-treatment protease sequencing. All but two (D30N and nelfinavir, G48V and saquinavir) of the expected the associations between individual PIs and primary PI resistance mutations were evident in the study population (Table 3). There was inadequate statistical power to detect associations between use of amprenavir or lopinavir and mutations.

The models as described above were repeated for all amino acids in HIV-1 RT and protease and added the HLA-A and -B (broad) serotypes of all individuals as covariates, along with drug exposures. At those positions that were known primary or secondary drug resistance mutation sites, the characteristic drug resistance amino acid substitution was specified as the outcome. At all other positions, any non-consensus amino acid was the outcome.

TABLE 3

Amino acid substitutions in HIV-1 protease examined.

| Amino acid substitutions examined in HIV-1 protease | Published primary drug association(s) | Drug association(s) detected in study cohort | OR | P-value |
| --- | --- | --- | --- | --- |
| L10I/R | secondary broad PI | indinavir saquinavir | 2 3 | 0.005 <0.001 |
| D30N | nelfinavir | ND |  |  |
| M46I/L | primary indinavir | indinavir | 3 | 0.006 |
| G48V | primary saquinavir | ND |  |  |
| I54V/L | indinavir | indinavir | 5 | <0.001 |
| A71V/T | secondary broad PI | indinavir saquinavir | 2 3 | 0.017 <0.001 |

TABLE 3-continued

Amino acid substitutions in HIV-1 protease examined.

| Amino acid substitutions examined in HIV-1 protease | Published primary drug association(s) | Drug association(s) detected in study cohort | OR | P-value |
|---|---|---|---|---|
| 73 | secondary broad PI | indinavir | 4 | 0.002 |
|  |  | saquinavir | 10 | <0.001 |
| V77I | secondary broad PI | indinavir | 2 | 0.026 |
| V82A/T/F | Indinavir | indinavir | 3 | 0.01 |
|  | ritonavir | ritonavir | 2 | 0.03 |
| I84V | Indinavir | indinavir | 6 | <0.001 |
| N88S | Nelfinavir | nelfinavir | 11 | <0.001 |
| L90M | Saquinavir | saquinavir | 2 | 0.012 |
|  |  | nelfinavir | 9 | <0.001 |

PI = protease inhibitor

TABLE 4

Characteristic HLA-specific amino acid substitutions in HIV-1 RT for those HLA alleles with strongest associations in models. %-percentage of individuals of HLA type that have the substitution in their viral sequence.

| HLA allele | Site(s) of allele associated polymorphism in HIV-1 RT | CTL epitope (if known) containing/flanking polymorphism | Most common amino acid substitution(s) (%) |
|---|---|---|---|
| A2 | 39 | 32-41 | T39 |
| A11 | 53 |  | E53 |
|  | 166 | 158-166 LAI L. Menendez-Arias, A. Mas, E. Domingo, Viral Immunol 11, 167-181 (1998). Q. J. Zhang, R. Gavioli, G. Klein, M. G. Masucci, Proc Natl. Acad. Sci U.S.A 90, 2217-2221 (1993). L. Wagner et al., Nature 391, 908-911 (1998). S. C. Threlkeld et al., J Immunol 159, 1648-1657 (1997). | K166 |
| A28 | 32 |  | K32 |
| B5 | 135 | 128-135 IIIB L. Menendez-Arias, A. Mas, E. Domingo, Viral Immunol 11, 167-181 (1998). N. V. Sipsas et al., J Clin Invest 99, 752-762 (1997). H. Tomiyama et al., Hum Immunol 60, 177-186 (1999). | I135T/V reduced HLA binding in-vitro shown |
| B7 | 158 | 156-165 C. M. Hay et al., J Virol 73, 5509-5519 (1999). L. Menendez-Arias, A. Mas, E. Domingo, Viral Immunol 11, 167-181 (1998). C. Brander and B. D. Walker, in HIV molecular immunology database, B. T. M. Korber et al., Eds. New Mexico, 1997). | A158 |
|  | 165 |  | T165 |
|  | 169 |  | E169 |
| B8 | 32 | 20-26 | K32 |
| B12 | 203 | 203-212 (HLA-B44) | E203 |
|  | 211 |  | R211 |
| B15 | 207 |  | Q207 |
| B17 | 214 |  | F214 |
| B18 | 68 |  | S68 |
|  | 135 |  | I135 |
|  | 138 |  | E138 |
|  | 142 |  | I142 |

TABLE 4-continued

Characteristic HLA-specific amino acid substitutions in HIV-1 RT for those HLA alleles with strongest associations in models. %-percentage of individuals of HLA type that have the substitution in their viral sequence.

| HLA allele | Site(s) of allele associated polymorphism in HIV-1 RT | CTL epitope (if known) containing/flanking polymorphism | Most common amino acid substitution(s) (%) |
|---|---|---|---|
| B35 | 121 | 118-127 | D121 |
|  | 177 | 175-185 H. Shiga et al., AIDS, 10, 1075-1083 (1996). | D177 |
| B37 | 200 |  | T200 |
| B40 | 197 | 192-201 (HLA-B60) | Q197 |
|  | 207 | 207-216 (HLA-B60) | Q207 |

All of the 63 polymorphisms positively (OR>1) associated with specific HLA-A or HLA-B allele(s) in these models (p≦0.05 in all cases) were plotted on a map of HIV-1 RT in relation to the overall rate of polymorphism at each residue and known CTL epitopes. For 16 of these HLA-specific polymorphisms associations, the polymorphisms were located within or flanking CTL epitopes with corresponding HLA restriction, in keeping with CTL escape mutation and there appeared to be clustering of 14 associations along the sequence. HLA-associated polymorphisms were evident at four primary and nine non-primary anchor positions within the CTL epitopes and three were flanking CTL epitopes with corresponding HLA restriction. The characteristic amino acid substitutions present in those with the HLA alleles that had the strongest associations were then determined (Table 4). There were 32 negative HLA associations (OR<1) also evident—indicating that polymorphism, or change away from consensus was significantly less likely in the presence of these HLA alleles versus all others.

There were 48 HLA allele-specific polymorphisms in HIV-1 protease detected by the models. There were clustered polymorphisms for 8 HLA alleles, including those associated with HLA-B5 at positions 12, 13, 14 and 16. There were HLA associated polymorphisms within and flanking the only two published CTL epitopes, though none corresponded to the predicted HLA restriction of the epitopes (based on binding motifs). The strongest HLA associations and their characteristic amino acid substitutions present in the cohort are shown in Table 5. There were 23 negative HLA associations detected.

TABLE 5

Characteristic HLA-specific amino acid substitutions in HIV-1 protease for those HLA alleles with strongest associations in models.

| HLA allele | Site(s) of allele associated Polymorphism in HIV-1 protease | Most common amino acid substitution (%) |
|---|---|---|
| B5 | 12 | S (19.7%) |
| B7 | 10 | I (16.2%) |
| B12 | 35 | D (67.5%) |
|  | 37 | S (27.9%) |
| B13 | 62 | V (9.5%) |
| B15 | 46 | I (7.5%) |
|  | 90 | M (8.0%) |
|  | 93 | L (51.6%) |

TABLE 5-continued

Characteristic HLA-specific amino acid substitutions in HIV-1 protease for those HLA alleles with strongest associations in models.

| HLA allele | Site(s) of allele associated Polymorphism in HIV-1 protease | Most common amino acid substitution (%) |
|---|---|---|
| B37 | 35 | D (54.6%) |
|  | 37 | D (57.3%) |
| B40 | 13 | V (22.4%) |

There were four antiretroviral drug resistance mutations in HIV-1 RT (M41 L, K70R, T210W and T215 Y/F) and seven in protease (L10I/R, M46I/L, A71V/T, 73, V77I, V82A/T/F and L90M) at which HLA alleles independently increased the probability of the mutation. For example, the odds of developing M41L were markedly increased in individuals carrying HLA-A28 compared with all other HLA-A or -B alleles (OR=41, p<0.001). To examine this observation in more detail, we analyzed all individuals in the total cohort who had zidovudine exposure and HIV-1 RT sequencing at any time after treatment (n=265). The prevalence of HLA-A28 in this set of individuals (8.0%) was comparable to that of the total cohort (8.3%). However, the HLA-A28 allele was over-represented in the 58 zidovudine treated individuals with M41L (12.1%) compared with those 207 individuals who did not develop this substitution (7.7%, RR=1.69, p=0.30, Fisher's exact test). A similar analysis was carried out on all individuals who had nelfinavir treatment and HIV-1 protease sequencing (n=133). The presence of HLA-B13, associated with L90M in the logistic regression model (OR=13, p<0.001), was present in 40.0% of individuals with L90M compared with 18.7% without L90M after taking nelfinavir (RR=2.96, p=0.12, Fisher's exact test).

HLA alleles reduced the odds of two primary RT inhibitor resistance polymorphisms, K103N (HLA-A19, 1/OR=4, p=0.04) and M184V (HLA-B16, 1/OR=4, p=0.03) and one secondary PI resistance mutation L10I/R/V (HLA-A10, 1/OR=4, p=0.024), raising the possibility of antagonistic selection pressures in individuals with these specific HLA alleles treated with drugs that induce these mutations.

The findings of this study support a highly dynamic, host-specific model of HIV-1 adaptation in-vivo, in which host CTL responses and antiretroviral therapy act as continuous, competing or parallel interacting evolutionary forces at the level of single viral residues.

The distribution of common, known drug resistance mutations in the study cohort were comparable to that found in other large and small observational studies, including those in drug naïve individuals. Almost all known primary and most secondary drug resistance mutations were evident as drug-associated polymorphisms across the population and in all these cases, the drug association corresponded to the known causative antiretroviral agents. The expected associations between D30N and nelfinavir and G48V and saquinavir were not detected, though there was (at least 30%) power to detect significant drug associations with OR>2 for both mutations. Notably, G48V has been reported most frequently in-vivo in patients taking high dose saquinavir monotherapy, which has almost never been used in this study cohort. In most cases, saquinavir has been used together with ritonavir. Failure to detect known drug-associated polymorphisms using a population-based approach may be due to a lack of statistical power if use of the drug or virological failure on the drug is rare in the population, or if the mutation is predominantly selected in-vitro but not in-vivo. This method may prove useful for future novel antiretroviral drugs as a systematic way to characterize the most frequent, in-vivo drug resistance mutations induced by the drugs, even if the putative resistance sites in-vitro are not known.

In the same models that confirmed the expected selection effects of antiretroviral drugs, sequence diversity of several viral residues across the population was substantially influenced by the HLA characteristics of individual hosts. Previously, several HLA allele-specific polymorphisms in HIV-1 RT have been shown to correspond to known or likely sites of CTL escape, be more specific for fine HLA subtypes compared with broad serotypes, increase in frequency over time and predict higher plasma viral load. The models of HIV-1 RT sequence diversity have been further refined in this study by the adjustment for drug induced changes, leaving a core set of 22 polymorphisms that we present as putative CTL escape mutations (Table 4).

Protease (RPLVTIKI; positions 8 to 15) is a predicted CTL epitope based on the HLA-B5 binding motif and we found strong associations between HLA-B5 and a cluster of polymorphisms at positions 12, 13, 14 and 16. The considerable natural polymorphism of the protease gene has been noted in several studies and it is possible that at least some of this is CTL-driven (Table 5). The selected polymorphisms in HIV-1 RT and protease shown in Tables 4 and 5 had one or all of the following key characteristics; their statistical association with a HLA allele was very strong and remained significant (p<0.05) after adjustment for drug associated changes, polymorphisms at other positions (i.e. possible secondary mutations) and/or multiple comparisons, they fell within known CTL epitopes with a corresponding HLA restriction or were clustered with other polymorphisms associated with the same HLA allele. In all cases, there was either one or two predominant amino acid substitution(s) in the individuals carrying the HLA allele and the allele-associated polymorphism, as would be expected for a functional mutation selected by the CTL response. In the case of I135TN, this substitution has been shown by others to abrogate HLA binding to the viral epitope in-vitro. Thus, just as drug resistance mutations are considered 'characteristic' or signatures of exposure to a particular antiretroviral drug, these amino acid substitutions were characteristic for particular HLA alleles, and were evident in drug treated individuals.

Potent antiretroviral therapy with sustained suppression of HIV-1 replication has been shown to coincide with a diminution of anti-HIV CTL responses, suggesting that CTL escape is less likely to occur. The studies that have documented CTL escape to fixation over time in individuals have all been in the untreated. In this study cohort, individuals were more likely to have HIV-1 RT and/or protease sequencing performed during virological failure, rather than when successfully virologically controlled. Though we cannot determine the time at which each HLA-specific polymorphism typically first appears, the demonstration of independent HLA and drug associated effects on viral sequence implies that CTL may still exert selection pressure during or after a period of antiretroviral drug therapy in some individuals.

There are a few viral residues where CTL pressure and drug pressure appeared to compete or concur in driving to either change or not change from the wildtype amino acid. This raises the intriguing possibility that anti-HIV CTL responses could be an explanation for discordance of in-vitro/in-vivo drug resistance patterns, discordance of genotypic and phenotypic resistance and variable rates of emergence of drug resistance mutations in different individuals. Interactions between CTL pressure and drug pressure are therefore germane to many aspects of contemporary treatment strategy, such as comparisons of different antiretroviral regimens, structured treatment interruptions (STIs) and different timing of treatment initiation. It is increasingly acknowledged that the design and interpretation of studies on these issues is limited by an incomplete understanding of what determines biological variability in disease between individuals. Our findings to date argue for HLA typing and viral genotyping to inform the design of future clinical studies. For example, STIs would not be expected to enhance HIV specific CTL responses in individuals who have already escaped from those responses in-vivo. Being able to prospectively identify individuals with or without the key escape mutations for their HLA, would enable STIs to be administered to those most likely to benefit from them. Similarly, studies of individualized drug choice and treatment timing could be informed by this data. In the same way that baseline and periodic post-treatment RT and protease resistance genotyping has now become the standard of care for optimization of drug treatment, viral genotyping for critical escape mutations may greatly enhance individualization of antiretroviral treatment in the future.

Other groups have independently reported a number of these epitopes, e.g. an HLA-A11 restricted CTL epitope has been described between positions 117 and 126 of HIV reverse transcriptase (B. Sriwanthana et al., *Hum Retroviruses* 17, 719-34 (2001)). The following associations were also identified within subsequently published CTL epitopes: HLA-A3 at 101 within an HLA-A3 restricted CTL epitope RT(93-101; C. Brander and P. Goulder, in *HIV Molecular Immunology Database*. B. T. M. Korber et al., Eds. New Mexico, 2001); HLA-A19(30) at 178 within an HLA-A*3002 epitope (173-181; C. Brander and P. Goulder, in *HIV Molecular Immunology Database*. B. T. M. Korber et al., Eds. New Mexico, 2001; and P. Goulder et al., *J. Virol* 75(3), 1339-47 (2001)) and HLA-B40 at 207 within an HLA-B*4001 restricted CTL epitope (202-210; C. Brander and P. Goulder, in *HIV Molecular Immunology Database*. B. T. M. Korber et al., Eds. New Mexico, 2001).

mutations at these HLA-associated viral polymorphisms had a higher HIV viral load. This information indicates which HIV peptides (epitopes) stimulate the strongest protective immune response against the virus after infection. Those same epitopes should afford the strongest protection if given in a vaccine before exposure to the virus.

The protection afforded by a preventative HIV vaccine will depend on the breadth and strength of the HLA restricted immune responses elicited by the therapeutic and the extent to which the infecting HIV sequence has escaped those responses. The objective is (1) for the therapeutic to induce the maximum number and strength of HLA-restricted CTL responses and (2) to have the maximum number of identical matches between therapeutic epitopes and incoming viral epitopes (or for the viral epitopes to at least be similar enough to the therapeutic epitope to still be recognized by the therapeutic induced CTL response).

The traditional approach has been to try to include conserved epitopes—stretches of viral proteins that are eight to 12 amino acids long that are invariably present in all HIV variants. However, studies presented herein indicate that the virus and its ancestors have evolved under intense selective pressure from HLA-restricted immune responses and therefore tend not to have conserved epitopes recognized by common HLA types.

Figure 12A:
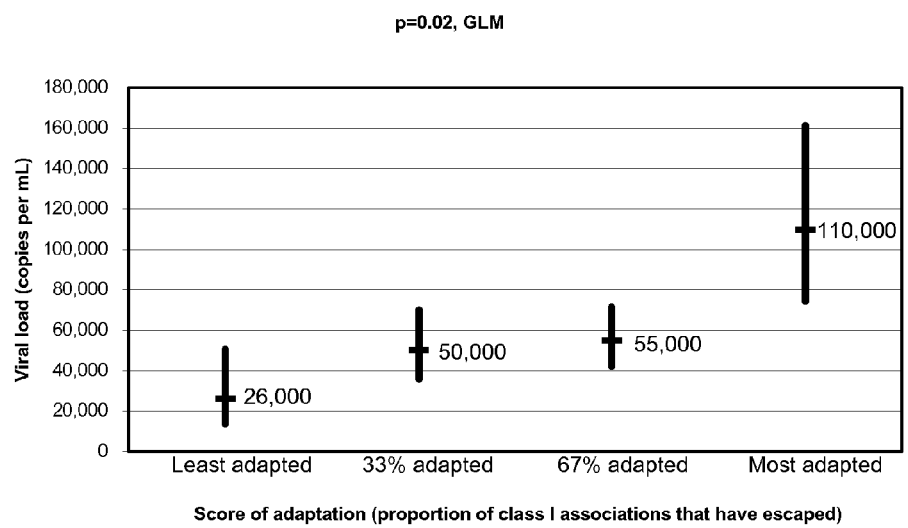
FIG. 12A shows the relationship between the degree of viral adaptation to HLA-restricted responses and the HIV viral load.
Figure 12B:
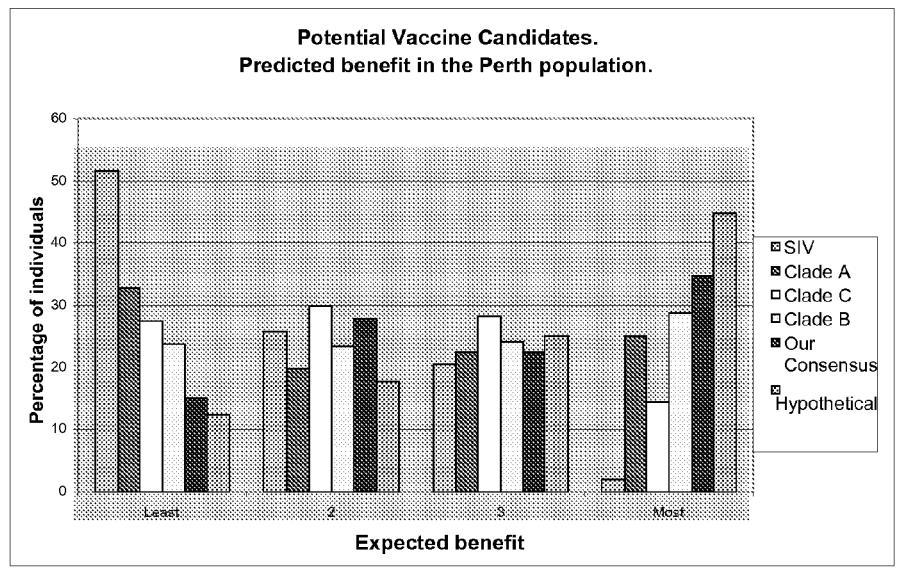
FIG. 12B shows the frequency distribution of the number of beneficial residues in each of six vaccine candidates (SIV, clade A virus, clade C virus, HXB2 virus, our population consensus virus, and a hypothetical vaccine) matched to each of the potential incoming infecting viruses in a West Australian population.

A preliminary analysis of the first 80 patients with full-length sequencing has revealed HLA specific associations in all the proteins and escape at these residues correlated with a higher pre-treatment viral load. The strongest associations and their relationship to HIV viral load are shown in Table 6. FIG. 12 shows the relationship between the degree of viral adaptation to HLA-restricted responses and the viral load. The number and strength of HLA-restricted associations and the degree to which these explain the variability in pre-treatment viral load will increase as data on a larger number of patients becomes available.

TABLE 6

| Protein | Amino acid position | HLA | Odds ratio | P-value | Estimated change in viral load | Consensus amino acid | Non-escaped amino acid |
| --- | --- | --- | --- | --- | --- | --- | --- |
| Integrase | 11 | B*4402 | 166.02 | <0.0001 | 1.39 | Glutamate | Aspartate |
| Nef | 14 | C*0701 | 6.78 | 0.0001 | 0.31 | Proline | Serine |
| p6 | 34 | A*2402 | 52.59 | 0.0002 | −0.02 | Glutamate | Aspartate |
| Nef | 71 | B*0702 | 19.40 | 0.0002 | 0.28 | Arginine | Lysine |
| p6 | 25 | B*4402 | 66.34 | 0.0003 | 0.91 | Serine | Proline |
| Integrase | 119 | DRB1-0101 | 429.45 | 0.0004 | −1.10 | Serine | Arginine |
| Vpr | 84 | DRB1-0701 | 0.03 | 0.0005 | −0.45 | Threonine | Isoleucine |
| Integrase | 122 | C*0501 | 17.24 | 0.0005 | 0.63 | Threonine | Isoleucine |
| Integrase | 119 | DRB1-0701 | 144.67 | 0.0005 | −0.12 | Serine | Glycine |
| Protease | 37 | DRB1-1302 | 19.98 | 0.0006 | 0.23 | Asparagine | Serine |
| Integrase | 17 | B*4001 | 8.00 | 0.0008 | −0.31 | Serine | Asparagine |
| p6 | 29 | A*2402 | 9.38 | 0.0008 | 0.43 | Glutamate | Glycine |
| Integrase | 119 | B*4402 | 273.63 | 0.0009 | 0.53 | Serine | Proline |
| p7 | 9 | B*1801 | 30.54 | 0.0010 | 0.20 | Glutamine | Proline |

HIV and ancestral retroviruses have evolved under intense selective pressure from HLA (or MHC) restricted immune responses. HIV has highly dynamic and error prone replication and evidence of this HLA restricted selective pressure can be seen in individual patients and at a population level. Of 473 Western Australian patients studied, no two patients had the same HIV Reverse Transcriptase amino acid sequence. Polymorphisms were most evident at sites of least functional or structural constraint and frequently were associated with particular host HLA Class I alleles. Patients who had escape A simulation was undertaken to determine the likely efficacy of different preventative vaccine candidates assuming an HIV negative target population with the same HLA diversity as the HIV positive Western Australian cohort was exposed to the same range of viral diversity observed in the Western Australian HIV positive cohort. In other words a hypothetical population of 249 HIV negative patients with the identical HLA types as the 249 HIV positive Western Australian patients was examined. The possibility of the first HIV negative patient being exposed to the virus sequenced in the first HIV infected patient was considered, then the virus in the second HIV positive patient and so on until all 80 viral sequences had been considered. This process was repeated for the second hypothetical HIV negative patient and so on until all 249 HIV negative subjects had been considered.

Figure 13:
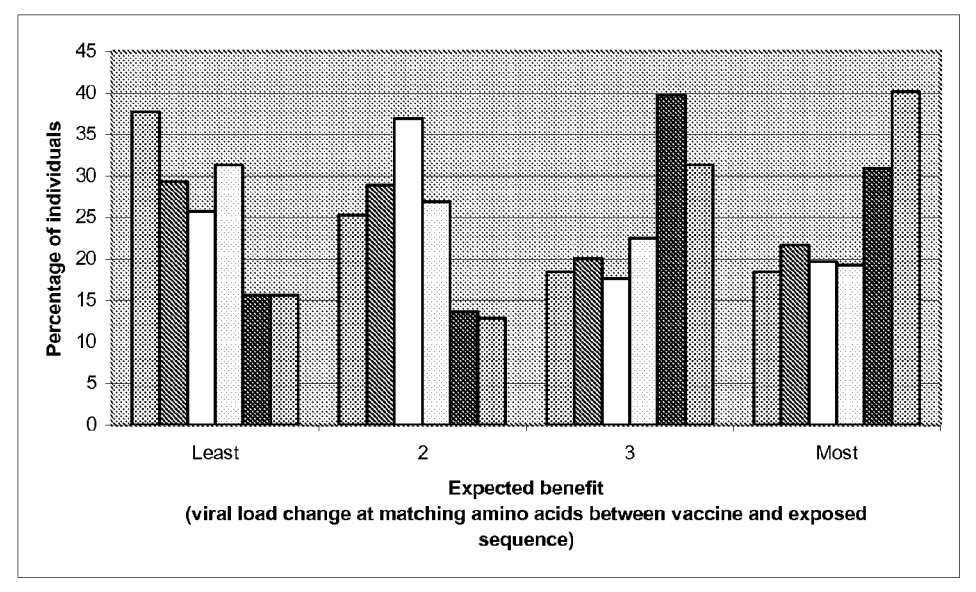

In the first analysis (FIG. 12B), for each potential therapeutic candidate, the number of beneficial amino acid residues that were present in the hypothetical therapeutic (i.e. a consensus at a positive HLA association and a match between the therapeutic and the incoming virus, or second most common residue at a negative HLA association and a match between this second most common residue and the incoming virus) was calculated. In the second analysis (FIG. 13), an estimated strength of the HLA-restricted immune response that would be induced by each therapeutic in response to each of the potential incoming viruses using the viral load results as illustrated in the estimated change in viral load column shown in Table 6 was calculated. Generally the use of consensus sequence for the study population reduced but did not eliminate the problem posed by the viral diversity and inclusion of the maximum number of HLA-A, B or C specific viral polymorphisms (particularly those associated with large viral load increases on escape) is predicted to improve HLA-restricted responses.

The following discussion provides an example of a hypothetical option to address HIV specific immune responses. At the commencement of treatment a blood sample is taken from each patient for use in HIV sequencing and HLA typing to determine which residues and hence virus populations have already escaped from HLA-restricted immune response using the HLA-viral polymorphism associations derived from a population based analysis. The methods for carrying out this analysis are described above.

Delivery of the vaccine to the patient is achieved using a fowlpox vector (or any other vector suitable for deliver of a protein sequence to a patient). This is achieved by well known and standard techniques which include isolation of a nucleotide sequence that encodes the proteins that are used in the vaccine. The nucleotide sequence is then inserted into the vector (e.g., fowlpox) and then delivered to a patient at levels and in a manner that leads to protein expression within the patient.

If the HIV sequence selected for use in the vaccine does not encode the specific sequence mentioned that sequence may be modified using well known and well understood techniques in molecular biology (see Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York., the text of which is incorporated herein by reference) including site directed mutagenesis techniques as an example.

A hypothetical treatment using a vaccine to maintain HIV specific immune responses as HIV antigen wanes during effective highly active antiretroviral therapy (HAART) can be administered according to the following method. At the commencement of treatment a blood sample is taken from each patient for use in HIV sequencing and HLA typing to determine which residues and hence virus populations have already escaped from HLA-restricted immune response using the HLA-viral polymorphism associations derived from a population based analysis. The patient is then placed on HAART to inhibit HIV replication decreasing the availability of HIV antigen to sustain HIV antigen specific immune responses. The protocols of the HAART treatment used depend on the patient to be treated. Physicians will adopt an appropriate protocol based on the level of infection in a patient, the health of the patient etc.

Over the course of HAART, regular monitoring of viral loads is carried out to measure the effect of treatment. Once viral load has waned sufficiently the patient is then placed on a vaccination protocol aimed at the desired epitope. The constitution of the therapeutic may vary depending on the precise needs of the treating physician.

A hypothetical treatment using a vaccine to prevent or delay the emergence of anti-retroviral drug resistance mutations in patients on highly active antiretroviral therapy is described below. Combination antiretroviral therapy (ART) has resulted in a 60% reduction in mortality from HIV-1 and provided great hope for those infected. However the development of drug resistance is a major hurdle in the long-term benefit it can provide both in the developed and developing world. Resistance to HIV medications following treatment is now common, with studies in the USA and Ivory Coast demonstrating over 50% of treated patients harbouring some resistance to HIV.

Vaccination aims to prevent the onset of disease states and has provided incalculable benefit to entire communities and humanity as a whole. The role of vaccination in those already infected with a particular disease is only currently being evaluated, especially in relation to HIV-1. A vaccine that could prevent or delay the development of drug resistance in those already infected with HIV-1 could provide significant benefit for the millions of people living with this disease.

The clinical benefit of therapeutic vaccines in HIV infected patients has been disappointing to date potentially because the patient has already been exposed to the vaccine antigens and the vaccines epitopes are to a variable extent escaped from HLA-restricted immune responses. Antiretroviral resistance mutations are detrimental to the patient but in this case the patient has not yet been exposed to the antigen. Use of a sufficiently immunogenic vaccine such as the DNA/Fowlpox prime/boost vaccine should provide high level T cell immunogenicity.

The objective is for the therapeutic construct to match the new epitope created when the anti-retroviral drug resistance mutation emerges. Ideally the autologous virus in each patient would be sequenced and an identical virus in all respects apart from the introduction of characteristic drug mutations be used in the therapeutic construct (i.e. a vaccine individualized to each patient). According to this hypothetical example, the patient is vaccinated by a process of introducing one or more vectors into the patient, which are adapted to express the protein sequence of the vaccine.

The vaccine is delivered as follows. A fowlpox vector is constructed containing cDNA. Insertion of the cDNA sequence encoding the epitope sequence should be carried out in a manner to ensure that the sequences will be expressed when introduced into a patient. The vector may also contain all expression elements necessary to achieve the desired transcription of the sequences. Other beneficial characteristics can also be contained within the vectors such as mechanisms for recovery of the nucleic acids in a different form. Reactions and manipulations involving nucleic acid techniques can be performed as generally described in Sambrook et al., 1989, Molecular Cloning: A Laboratory Manual, Cold Spring Harbor Laboratory Press, and methodology.

The constructed vector is then introduced into cells by any one of a variety of known methods within the art. Methods for transformation can be found in Sambrook et al., Molecular Cloning: A Laboratory Manual, Cold Springs Harbor Laboratory, New York (1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor, Mich. (1995) and Gilboa, et al. (1986) and include, for example, stable or transient transfection, lipofection, electroporation and infection with recombinant viral vectors.

Information concerning the extent to which the strain of HIV infecting an individual has escaped their HLA-restricted immune response may be used to individualize and guide the timing and type of treatment to be used. In general treatment should aim to prevent further HIV escape from or adaptation to HLA-restricted immune responses.

The following is a hypothetical example of a diagnostic technique. Sequences identified as escape mutations are synthesized using standard protein synthesis techniques known in the art. Such techniques are described in Sambrook et al., *Molecular Cloning: A Laboratory Manual*, Second Edition, Cold Spring Harbor Laboratory Press, Cold Spring Harbor, New York (1989); Ausubel, F., Brent, R., Kingston, R. E., Moore, D. D., Seidman, J. G., Smith, J. A., Struhl, K. *Current protocols in molecular biology*. Greene Publishing Associates/Wiley Intersciences, New York. Once the proteins have been sequences they are used to generate antibodies according to, for instance, the methodology described first in Kohler and Milstein, Nature, 256:495-497 (1975). Antibodies prepared by the above methodology can be employed in an ELISA assay as described in Chapter 11 of Ausubel, et al.

Figure 16:
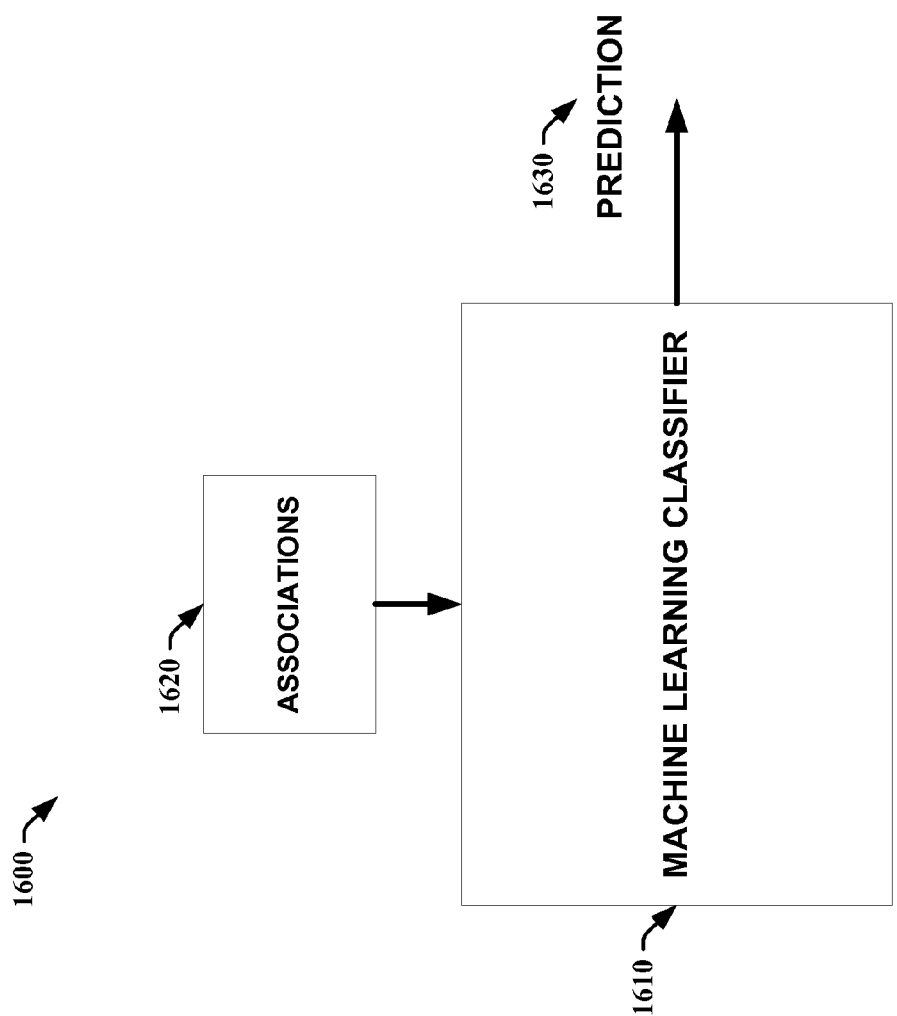
FIG. 16 is a schematic illustration of a system that facilitates making a prediction.

FIG. 16 is a block diagram of one example of a system 1600 that facilitates making a prediction. The system 1600 comprises a machine learning classifier 1610 to make predictions 1630. By way of example, the system 1600 can predict a pathogen characteristic relating to a disease state of the host, such as a disease state affecting the host's immune system (e.g., an acquired immunodeficiency).

The machine learning classifier 1610 can be trained, for instance, on a plurality of associations 1620 between the host and the pathogen. Any suitable type of association 1620 can be used to train the machine learning classifier including but not limited to an MHC-type of an individual and a mutation of a microbe. If a suitable association 1620 exists, any pathogen characteristic can be predicted (e.g., a polypeptide, polynucleotide, etc.). By way of example, the system 1600 can be trained using data relevant to a medical condition, for instance, an association 1620 between host alleles and HIV characteristics (or any other pathogenic organism, e.g., HCV, HSV, etc.). The machine learning classifier 1610 can be of any suitable type, such as a neural network, logistic regression, a decision tree, a support vector machine, etc. The machine learning classifier 1610 can be encoded by computer-executable instructions and stored on computer-readable media.

By way of example, the system 1600 can be employed to predict an epitope of about 8 to about 11 amino acids in length. The classifier 1610 can be learned utilizing a plurality of associations 1620 between HLA-type and HIV escape mutations. Examples of a plurality of associations between HLA-type and HIV escape mutations are described supra in reference to FIGS. 8-13. To determine epitopes likely to be recognized by the immune system of an individual of a particular HLA type, the machine learning classifier 1610 can be applied to each 8-11 amino-acid sequence in the vicinity of the mutation using, for instance, a 33-amino-acid-long window on either side of the mutation. The 33-amino-acid-long window is chosen because the positions flanking an epitope can influence whether it is presented on a cell's surface. Using a 33-amino-acid-long window allows for a 12-amino-acid-long flanking region on either side of a 9-amino-acid-long epitope. Any window appropriate for the pathogen characteristic and the association 1620 can be chosen.

By way of another example, logistic regression with features selected by the wrapper method can be used to predict epitopes. Positive examples include the 9-mers obtained from the LANL (hiv-web.lanl.gov) and SYFPEITHI (www.syfpeithi.de/) databases. Negative examples can be generated at random from the marginal distribution of amino acids from the positive examples. The features used for prediction comprise: (1) the 2-4 digit HLA of the epitope; (2) the supertype of that HLA; (3) the amino acid at each position in the epitope; and (4) the chemical properties of each amino acid at each position in the epitope and conjunctions 1+3, 1+4, 2+3, and 2+4.

Figure 17:
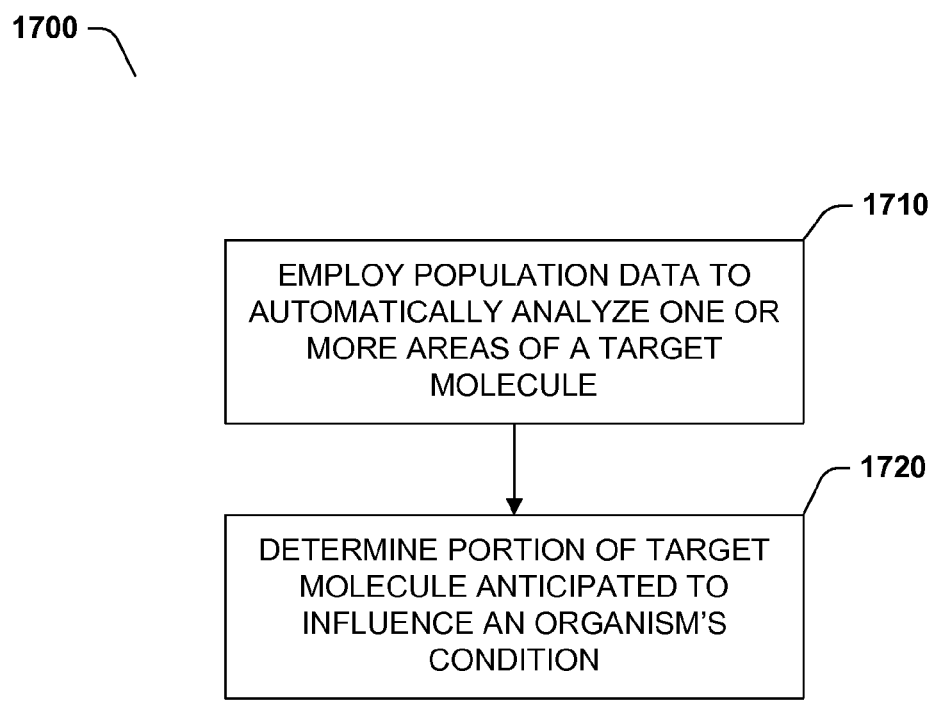
FIG. 17 is a flow diagram illustrating a method of forecasting a portion of a target molecule.

FIG. 17 shows a flow diagram illustrating one example of a method 1700 of forecasting a portion of a target molecule anticipated to influence an organism's condition. The method can be encoded by computer-executable instructions stored on computer-readable media. At step 1710 of the method 1700, population data is employed to automatically analyze one or more areas of the target molecule. At step 1720, the portion of the target molecule expected to influence the organism's condition is determined. Any of the techniques described above and below can be employed to accomplish steps 1710 and 1720.

Figure 18:
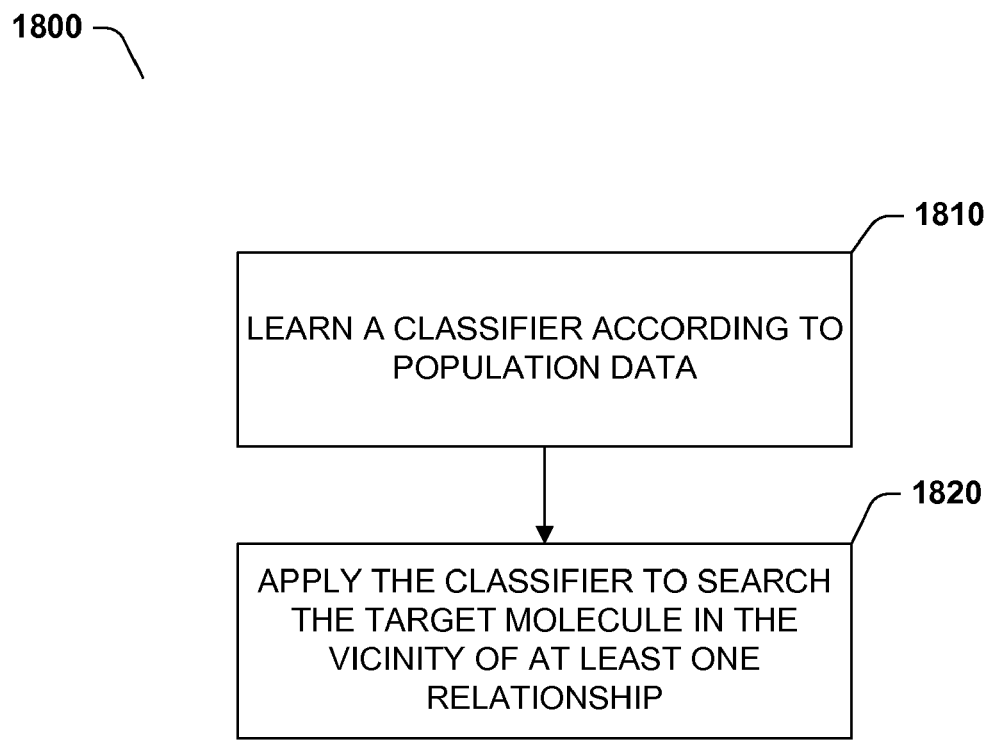
FIG. 18 is a flow diagram illustrating another method of forecasting a portion of a target molecule.

FIG. 18 shows a flow diagram illustrating another exemplary method 1800 of forecasting a portion of a target molecule. At step 1810 a classifier is learned according to population data. The population data, for instance, can pertain to a relationship between a diverse trait of the particular organisms and the target molecule (e.g., a relationship between an allele and a sequence). At step 1820, the classifier is applied to search the target molecule in the vicinity of a site determined by the relationship. By way of example, the organism's condition can be a malignancy and/or an infection. In one embodiment of the methods 1700 or 1800, the organism's condition is the Acquired Immunodeficiency Syndrome, the portion of the target molecule is an epitope, the relationship is between an MHC-type and a mutation, and the forecast is made by searching in the vicinity of the mutation using a window of length sufficient to include regions flanking the epitope (e.g., about 33 amino acids in length).

Figure 19:
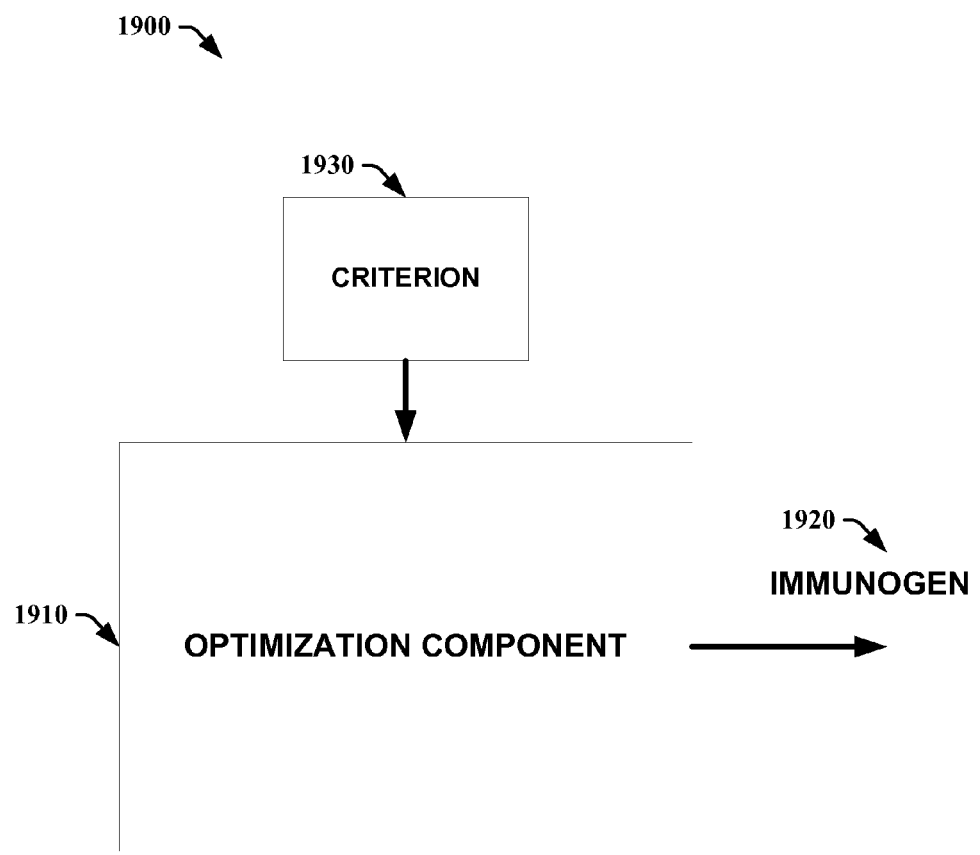
FIG. 19 is a schematic illustration of a system that facilitates immunogen design.
Figure 20:
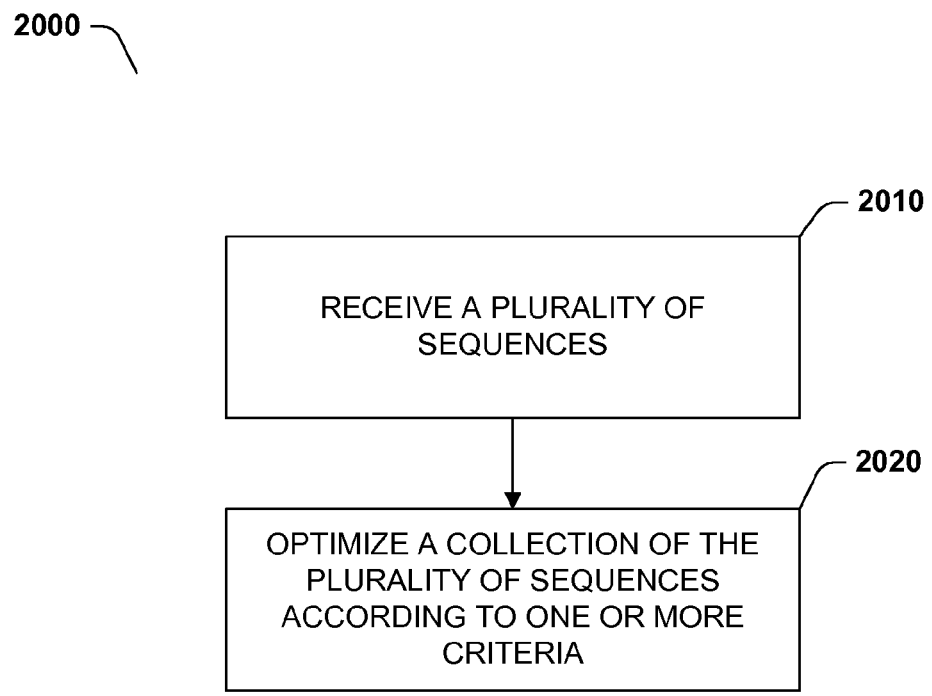
FIG. 20 is a flow diagram illustrating a method of determining an epitome.
Figure 21:
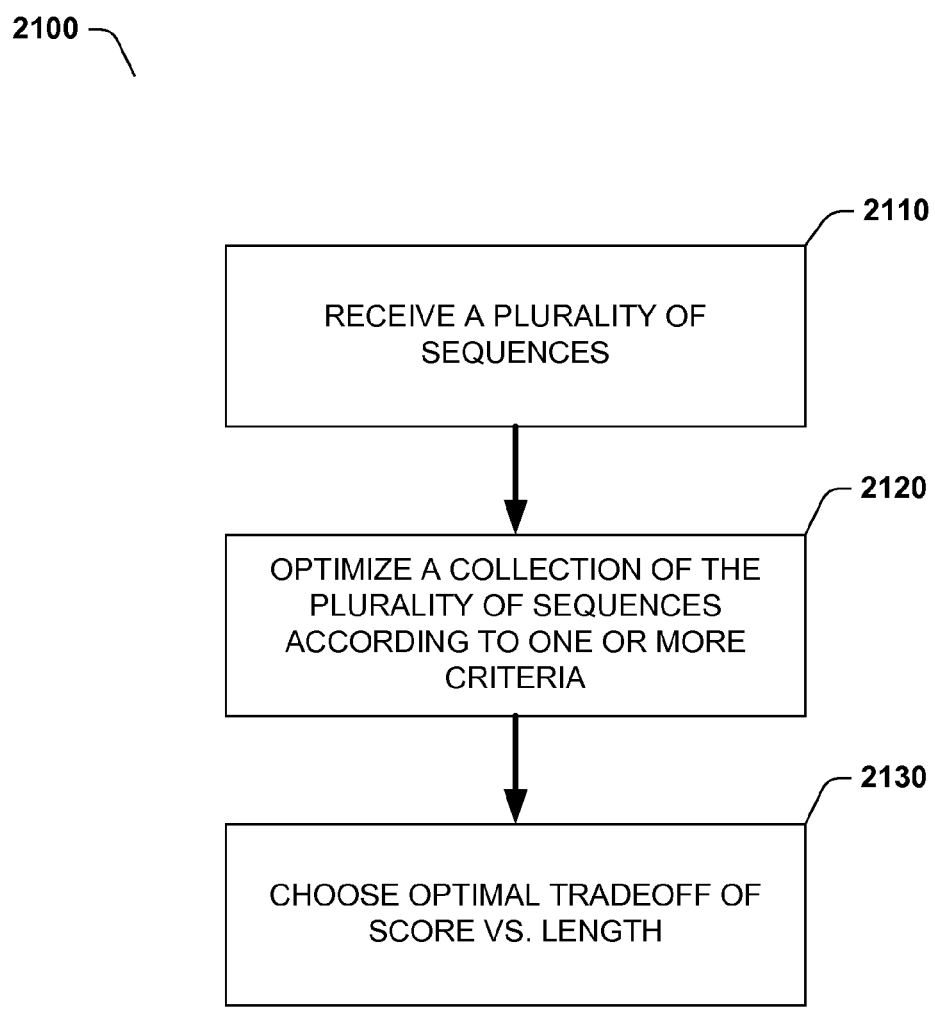
FIG. 21 is a flow diagram illustrating another method of determining an epitome.

FIG. 19 is a schematic illustration of one example of a system 1900 that facilitates immunogen design. The system 1900 comprises an optimization component 1910 to determine the immunogen 1920 according to at least one criterion 1930. The immunogen 1920 can be, for example, a set of overlapping sequences that are known to be and/or are likely to be immunogenic. At least one of the sequences that are likely to be immunogenic can be determined by analyzing associations between a host and a pathogen at a population level. Any of the techniques described above can be employed to determine sequences likely to be immunogenic.

By way of example, the pathogen can be HIV and the associations can be between an MHC-type and escape mutations. The optimization component 1910 can employ a greedy algorithm to determine the immunogen or any suitable optimization algorithm can be used (e.g., any of the techniques described above in reference to FIGS. 1-7). For instance, a greedy algorithm that constructs a collection of sequences which together yield a large optimization score can be employed. The greedy algorithm can iteratively insert (usually with overlap) a single epitope into the collection of sequences such that the optimization score per unit length (where length is the total length of all the sequences) increases the most. This procedure produces a series of epitomes, each with an optimization score and a length. External considerations can be used to choose the optimal tradeoff of score versus length.

By way of another example, the optimization criteria can reflect the idea that if a vaccinated person with a given HLA type is exposed to a given sequence (or collection of sequences), only the epitopes in the sequence that are (1) present in the vaccine (or that will cross react with CD8+ T cells stimulated by the vaccine) and (2) can be presented by an HLA molecule expressed by the patient will contribute to immune protection. One example of an optimization criterion is the expected number of cross-reacting epitopes per patient, where expectation is taken over the given population of individuals and the given population of sequences. There are different models for determining whether CD8+ T cells stimulated with one sequence will cross-react with another epitope. One example of such a model assumes that there must be an exact match between the sensitizing peptide and the reacting epitope. Another example of a model assumes that the sensitizing peptide and the reacting epitope must differ by at most one conservative amino acid change.

The optimization component can be encoded by computer-executable instructions stored on computer-readable media. There are numerous strategies for delivering immunogens such as delivering each sequence in an epitome on its own viral vector, concatenating the sequences in the epitopes and delivering them on a single viral vector, and/or each sequence can be further subdivided (e.g., to avoid immunodominance) and each component delivered on a separate viral vector. Any of the techniques described above and others known in the art can be used to assemble and deliver the immunogen.

FIG. 20 is a flow diagram illustrating one example of a method 2000 of determining an epitome. At step 2010, a plurality of sequences are received. The sequences can be, for example, sequences predicted to be an epitope based on a relationship between a diverse trait of a population and a mutation of a pathogen. By way of another example, one or more of the plurality of sequences comprises at least one flanking region. At step 2020, a collection of the plurality of sequences are optimized according to one or more criteria to determine the epitome. Optimization can be accomplished by a greedy algorithm or any suitable optimization algorithm (e.g., any of the techniques described above in reference to FIGS. 1-7 and 19). The criteria can be length, cross-reactivity, and/or any suitable criteria or combinations thereof, such as an optimization score per unit length.

FIG. 21 is a flow diagram illustrating another method of determining an epitome. At step 2110, a plurality of sequences are received. At step 2020, a collection of the plurality of sequences are optimized according to one or more criteria. At step 2130, a tradeoff between the optimization score and length of the epitome is considered to determine the epitome.

Exemplary nine (9) amino acid sequences shown in Table 7 were determined by the systems/methods described above.

TABLE 7

| 9Mer | Escape9Mer | Association Position | HLA | Protein |
|---|---|---|---|---|
| SEQ ID NO: 1 ANNADCAWL | SEQ ID NO: 73 ATNADCAWL | E1 | A0301 | Nef |
| SEQ ID NO: 2 NNNETETFR | SEQ ID NO: 74 TNNETETFR | B-1 | A0301 | Env |
| SEQ ID NO: 3 SKKAKGWFY | SEQ ID NO: 75 SRKAKGWFY | E1 | A0101 | Vif |

TABLE 7-continued

| 9Mer | Escape9Mer | Association Position | HLA | Protein |
|---|---|---|---|---|
| SEQ ID NO: 4 ISPRTLNAW | SEQ ID NO: 76 ISPRTLNAL | E8 | A0101 | Gag |
| SEQ ID NO: 5 AAVKAACWW | SEQ ID NO: 77 TAVKAACWW | B-1 | A0201 | Pol |
| SEQ ID NO: 6 PIAPGQMRE | SEQ ID NO: 78 PIPPGQMRE | E2 | A0101 | Gag |
| SEQ ID NO: 7 NSSQVSQNY | SEQ ID NO: 79 SSSQVSQNY | B-1 | A0101 | Gag |
| SEQ ID NO: 8 RDWHLGHGV | SEQ ID NO: 80 RDWHLGQGV | E6 | B0801 | Vif |
| SEQ ID NO: 9 PIWKGPAKL | SEQ ID NO: 81 PLWKGPAKL | E1 | B0801 | Pol |
| SEQ ID NO: 10 LVWRWGTML | SEQ ID NO: 82 WVWRWGTML | B-1 | B0702 | Env |
| SEQ ID NO: 11 GPSHKARVL | SEQ ID NO: 83 GPGHKARVL | E2 | A2402 | Gag |
| SEQ ID NO: 12 YLSWVPAHK | SEQ ID NO: 84 YLAWVPAHK | E2 | A0201 | Pol |
| SEQ ID NO: 13 KQGQDQWTY | SEQ ID NO: 85 KQGQGQWTY | E4 | B0702 | Pol |
| SEQ ID NO: 14 HIVSPRCDY | SEQ ID NO: 86 HIVSPRCEY | E7 | B0801 | Vif |
| SEQ ID NO: 15 VDPDLADQL | SEQ ID NO: 87 VDPDLADRL | E7 | A0101 | Vif |
| SEQ ID NO: 16 DARLVITTY | SEQ ID NO: 88 DAKLVITTY | E2 | A1101 | Vif |
| SEQ ID NO: 17 KQGQGQWTY | SEQ ID NO: 89 KQGLGQWTY | E3 | B1501 | Pol |
| SEQ ID NO: 18 HIVSPRCEY | SEQ ID NO: 90 HIVSPSCEY | E5 | A2402 | Vif |
| SEQ ID NO: 19 PAIFQSSMT | SEQ ID NO: 91 PAIFQCSMT | E5 | B0801 | Pol |
| SEQ ID NO: 20 RPGNFLQSR | SEQ ID NO: 92 RPGNFPQSR | E5 | A1101 | Gag |
| SEQ ID NO: 20 RPGNFLQSR | SEQ ID NO: 92 RPGNFPQSR | E5 | A2402 | Gag |
| SEQ ID NO: 21 VDPGLADQL | SEQ ID NO: 93 VDPDLADQL | E3 | B0702 | Vif |
| SEQ ID NO: 22 YNEWTLELL | SEQ ID NO: 94 YNQWTLELL | E2 | A2402 | Vpr |
| SEQ ID NO: 23 TLKQIVKKL | SEQ ID NO: 95 MLKQIVKKL | B-1 | A0101 | Env |
| SEQ ID NO: 24 GDQEELSAL | SEQ ID NO: 96 GDQEELAAL | E6 | A0101 | Vpu |
| SEQ ID NO: 25 EQELLELDK | SEQ ID NO: 97 EQELLALDK | E5 | A1101 | Env |
| SEQ ID NO: 26 ALQDSGSEV | SEQ ID NO: 98 ALQDSGLEV | E6 | A0201 | Pol |
| SEQ ID NO: 27 KSKKKAQQA | SEQ ID NO: 99 KCKKKAQQA | E1 | A2402 | Gag |

TABLE 7-continued

| 9Mer | Escape9Mer | Association Position | HLA | Protein |
|---|---|---|---|---|
| SEQ ID NO: 28 SENFTDNAK | SEQ ID NO: 100 SENFTNNAK | E5 | A0301 | Env |
| SEQ ID NO: 29 NAKTIIVQL | SEQ ID NO: 101 NAKNIIVQL | E3 | A0101 | Env |
| SEQ ID NO: 30 YKVVRIEPL | SEQ ID NO: 102 YKVVKIEPL | E4 | B0702 | Env |
| SEQ ID NO: 31 IVNRVRQGY | SEQ ID NO: 103 VVNRVRQGY | B-1 | B0801 | Env |
| SEQ ID NO: 7 NSSQVSQNY | SEQ ID NO: 104 NSSKVSQNY | E3 | A1101 | Gag |
| SEQ ID NO: 4 ISPRTLNAW | SEQ ID NO: 105 LSPRTLNAW | B-1 | A0101 | Gag |

TABLE 7-continued

| 9Mer | Escape9Mer | Association Position | HLA | Protein |
|---|---|---|---|---|
| SEQ ID NO: 62 RWNKPQKTK | SEQ ID NO: 146 RWNKPRKTK | E5 | B0702 | Vif |
| SEQ ID NO: 63 LTVQARQLL | SEQ ID NO: 147 LTVQARLLL | E6 | A0201 | Env |
| SEQ ID NO: 64 TVKCFNCGK | SEQ ID NO: 148 IVKCFNCGK | B-1 | A0101 | Gag |
| SEQ ID NO: 65 RSVVGWPAV | SEQ ID NO: 149 SSVVGWPAV | B-1 | A0301 | Nef |
| SEQ ID NO: 66 AVGIGAMFL | SEQ ID NO: 150 AVGIGAVFL | E6 | A0201 | Env |
| SEQ ID NO: 67 AFHHMAREL | SEQ ID NO: 151 AFHHMAREK | E8 | A1101 | Nef |
| SEQ ID NO: 41 FPRPWLHGL | SEQ ID NO: 152 FPRIWLHGL | E3 | B0702 | Vpr |
| SEQ ID NO: 68 | SEQ ID NO: 153 | E8 | A0201 | Pol |
| SEQ ID NO: 69 CSSNITGLL | SEQ ID NO: 154 CSSNITGLI | E8 | A0101 | Env |
| SEQ ID NO: 69 CSSNITGLL | SEQ ID NO: 154 CSSNITGLI | E8 | A2402 | Env |
| SEQ ID NO: 22 YNEWTLELL | SEQ ID NO: 155 HNEWTLELL | B-1 | A0101 | Vpr |
| SEQ ID NO: 70 VPLTEEAEL | SEQ ID NO: 156 VTLTEEAEL | E1 | A0101 | Pol |
| SEQ ID NO: 71 KLAGRWPVK | SEQ ID NO: 157 KLAGRWPVT | E8 | A1101 | Pol |
| SEQ ID NO: 72 ALFYKLDVV | SEQ ID NO: 158 ALFYKLDVI | E8 | A0201 | Env |
| SEQ ID NO: 52 TAVPWNASW | SEQ ID NO: 138 IAVPWNASW | B-1 | A0201 | Env |
| SEQ ID NO: 10 LVWRWGTML | SEQ ID NO: 139 LVWRWGTLL | E7 | A2402 | Env |
| SEQ ID NO: 46 PAVRERMRR | SEQ ID NO: 140 SAVRERMRR | B-1 | B0801 | Nef |
| SEQ ID NO: 58 ELKNSAVSL | SEQ ID NO: 141 ELKNSAISL | E6 | B1501 | Env |
| SEQ ID NO: 10 LVWRWGTML | SEQ ID NO: 142 LVWRWGIML | E6 | A1101 | Env |
| SEQ ID NO: 59 PIDNDNTSY | SEQ ID NO: 143 QIDNDNTSY | B-1 | A0101 | Env |
| SEQ ID NO: 60 RAMASDFNL | SEQ ID NO: 144 RAMANDFNL | E4 | A0101 | Pol |
| SEQ ID NO: 61 STLQEQIGW | SEQ ID NO: 145 SNLQEQIGW | E1 | A0101 | Gag |
| SEQ ID NO: 61 STLQEQIGW | SEQ ID NO: 145 SNLQEQIGW | E1 | A1101 | Gag |
| SEQ ID NO: 62 RWNKPQKTK | SEQ ID NO: 146 RWNKPRKTK | E5 | B0702 | Vif |
| SEQ ID NO: 63 LTVQARQLL | SEQ ID NO: 147 LTVQARLLL | E6 | A0201 | Env |
| SEQ ID NO: 64 TVKCFNCGK | SEQ ID NO: 148 IVKCFNCGK | B-1 | A0101 | Gag |
| SEQ ID NO: 65 RSVVGWPAV | SEQ ID NO: 149 SSVVGWPAV | B-1 | A0301 | Nef |
| SEQ ID NO: 66 AVGIGAMFL | SEQ ID NO: 150 AVGIGAVFL | E6 | A0201 | Env |
| SEQ ID NO: 67 AFHHMAREL | SEQ ID NO: 151 AFHHMAREK | E8 | A1101 | Nef |
| SEQ ID NO: 41 FPRPWLHGL | SEQ ID NO: 152 FPRIWLHGL | E3 | B0702 | Vpr |
| SEQ ID NO: 68 | SEQ ID NO: 153 | E8 | A0201 | Pol |

ITOPIA Test Results

The amino acid sequences shown in Table 8 were tested as described below using the BECKMAN COULTER ITOPIA Epitope Discovery System.

TABLE 8

| SEQ ID NO: | Sequence |
|---|---|
| 72 | ALFYKLDVV |
| 158 | ALFYKLDVI |
| 71 | KLAGRWPVK |
| 157 | KLAGRWPVT |
| 70 | VPLTEEAEL |
| 156 | VTLTEEAEL |
| 22 | YNEWTLELL |
| 155 | HNEWTLELL |
| 69 | CSSNITGLL |
| 154 | CSSNITGLI |
| 68 | RGRQKVVSL |
| 153 | RGRQKVVSI |
| 41 | FPRPWLHGL |
| 152 | FPRIWLHGL |

Peptide binding, off-rate and affinity were measured according to the protocols described in the ITOPIA Epitope Discovery System Customer Guide. To conduct the experiments, ninety-six (96) micro-titer plates coated with MHC molecules representing the HLA alleles listed in Table 9 were used to identify candidate peptides. Determinations were performed in duplicate using an ELISA plate reader. The peptide binding assay used measures the ability of individual peptides to bind to the HLA molecules under standardized optimal binding conditions. The assay was performed for all the test peptides across the selected HLA alleles. The test peptides identified as "binders" were characterized further in terms of affinity and dissociation experiments. The off-rate assay used evaluates the dissociation of previously bound peptide at defined time points (expressed as the $t_{1/2}$ value). The affinity assay used measures the relative binding affinities for the MHC molecules determined by incubating candidate peptides identified in the initial peptide binding assay at increasing concentrations (expressed as quantity of peptide needed to achieve 50% binding or ED50 value).

TABLE 9

| Allele |
|---|
| A*0101 |
| A*0201 |
| A*0301 |

TABLE 9-continued

| Allele |
| --- |
| A*1101 |
| A*2402 |
| B*0702 |
| B*0801 |
| B*1501 |

Peptide Binding Results

The binding of the test peptides (Table 8) to the HLA molecules (Table 9) was performed at a concentration of $1.11 \times 10^{-4}$ M of peptide under optimal, standardized test conditions. A control peptide was run in parallel on the same plate and at the same concentration as the test peptides. The following table (Table 10) shows the results of the initial binding by allele for each peptide. The level of binding is expressed as a percent of positive control peptide binding for each allele.

TABLE 10

| SEQ ID NO: | Sequence | A*0101 | A*0201 | A*0301 | A*1101 | A*2402 | B*0702 | B*0801 | B*1501 |
| --- | --- | --- | --- | --- | --- | --- | --- | --- | --- |
| 72 | ALFYKLDVV | 4 | 80 | 5 | 1 | 14 | 3 | 3 | 4 |
| 158 | ALFYKLDVI | 1 | 62 | 14 | 1 | 99 | 3 | 5 | 3 |
| 71 | KLAGRWPVK | 0 | 26 | 114 | 160 | 11 | 0 | 4 | 2 |
| 157 | KLAGRWPVT | 2 | 51 | 9 | 19 | 8 | 3 | 4 | 6 |
| 70 | VPLTEEAEL | 1 | 5 | 0 | 1 | 6 | 4 | 4 | 4 |
| 156 | VTLTEEAEL | 1 | 26 | 0 | 1 | 11 | 0 | 4 | 7 |
| 22 | YNEWTLELL | 0 | 7 | 0 | 1 | 35 | 2 | 3 | 0 |
| 155 | HNEWTLELL | 0 | 5 | 0 | 1 | 13 | 1 | 3 | 0 |
| 69 | CSSNITGLL | 4 | 37 | 0 | 1 | 26 | 5 | 4 | 30 |
| 154 | CSSNITGLI | 5 | 44 | 0 | 1 | 29 | 5 | 6 | 40 |
| 68 | RGRQKVVSL | 0 | 5 | 0 | 0 | 17 | 96 | 73 | 55 |
| 153 | RGRQKVVSI | 0 | 6 | 0 | 6 | 29 | 88 | 71 | 7 |
| 41 | FPRPWLHGL | 0 | 12 | 0 | 0 | 35 | 123 | 19 | 6 |
| 152 | FPRIWLHGL | 0 | 9 | 0 | 0 | 41 | 132 | 39 | 3 |

Off-rate Analysis

The peptides initially identified as binders were evaluated for stability based on their ability to remain bound to MHC molecules at 37° C. at time points 0, 0.5, 1, 1.5, 2, 4, 6 and 8 hours. Curve fitting this data was performed to yield a half-life in hours ($t_{1/2}$) measurement for each peptide. The values obtained for each time point (in duplicate) are expressed (Table 11) as a percentage of the positive control. To calculate the $t_{1/2}$ and goodness-of-fit, as measured by $r^2$, for each peptide, a one-phase exponential decay curve, with a plateau given equal to 0, was generated using GRAPHPAD PRISM software.

TABLE 11

| SEQ ID NO: | Sequence | A*0201 $t_{1/2}$ ($r^2$) | A*0301 $t_{1/2}$ ($r^2$) | A*1101 $t_{1/2}$ ($r^2$) | A*2402 $t_{1/2}$ ($r^2$) | B*0702 $t_{1/2}$ ($r^2$) | B*0801 $t_{1/2}$ ($r^2$) | B*1501 $t_{1/2}$ ($r^2$) |
| --- | --- | --- | --- | --- | --- | --- | --- | --- |
| 72 | ALFYKLDVV | 4.0 (0.76) | | | | | | |
| 158 | ALFYKLDVI | 5.5 (0.72) | | | 1.1 (0.37) | | | |
| 71 | KLAGRWPVK | | 1.3 (0.89) | 4.6 (0.22) | 2.6 (0.50) | | | |

TABLE 11-continued

| SEQ ID NO: | Sequence | A*0201 $t_{1/2}$ ($r^2$) | A*0301 $t_{1/2}$ ($r^2$) | A*1101 $t_{1/2}$ ($r^2$) | A*2402 $t_{1/2}$ ($r^2$) | B*0702 $t_{1/2}$ ($r^2$) | B*0801 $t_{1/2}$ ($r^2$) | B*1501 $t_{1/2}$ ($r^2$) |
|---|---|---|---|---|---|---|---|---|
| 157 | KLAGRWPVT | 1.1 (0.96) | | 1.6 (0.63) | | | | |
| 156 | VTLTEEAEL | 1.2 (0.66) | | | | | | |
| 22 | YNEWTLELL | | | | 1.5 (0.03) | | | |
| 69 | CSSNITGLL | 0.3 (0.95) | | | 1.1 (0.13) | | | 3.1 (0.01) |
| 154 | CSSNITGLI | 0.4 (0.91) | | | 1.5 (0.02) | | | 3.8 (0.03) |
| 68 | RGRQKVVSL | | | | | 1.1 (0.05) | 1.2 (0.07) | 3.5 (0.02) |
| 153 | RGRQKVVSI | | | | 1.8 (0.00) | 1.3 (0.04) | 1.2 (0.00) | |
| 41 | FPRPWLHGL | | | | 2.1 (0.01) | 1.2 (0.07) | | |
| 152 | FPRIWLHGL | | | | Curve Err | 1.1 (0.35) | 1.8 (0.25) | |

Affinity Analysis

Dose-response curves of peptide binding to MHC were prepared by peptide titration to determine the ED50 measurement for each peptide. The values obtained for the tested concentrations (in duplicate) are expressed in percentage of the highest 9000× concentration of the positive control peptide (Table 12).

TABLE 12

| SEQ ID NO: | Sequence | A*0201 ED50 ($r^2$) | A*0301 ED50 ($r^2$) | A*1101 ED50 ($r^2$) | A*2402 ED50 ($r^2$) | B*0702 ED50 ($r^2$) | B*0801 ED50 ($r^2$) | B*1501 ED50 ($r^2$) |
|---|---|---|---|---|---|---|---|---|
| 72 | ALFYKLDVV | 2.E-06 (0.98) | | | | | | |
| 158 | ALFYKLDVI | 4.E-06 (0.99) | | | 9.E-07 (0.99) | | | |
| 71 | KLAGRWPVK | 3.E-05 (0.98) | 2.E-06 (0.96) | 6.E-07 (0.99) | | | | |
| 157 | KLAGRWPVT | 3.E-05 (0.99) | | 2.E-04 (0.99) | | | | |
| 156 | VTLTEEAEL | 4.E-06 (0.95) | | | | | | |
| 22 | YNEWTLELL | | | | 3.E-06 (0.75) | | | |
| 69 | CSSNITGLL | 5.E-06 (1.00) | | | 1.E-04 (0.91) | | | 1.E-03 (0.99) |
| 154 | CSSNITGLI | 9.E-07 (0.91) | | | 3.E-05 (0.94) | | | 2.E-04 (0.82) |
| 68 | RGRQKVVSL | | | | | 5.E-06 (0.99) | 9.E-06 (0.99) | 4.E-04 (0.97) |
| 153 | RGRQKVVSI | | | | 3.E-06 (0.77) | 8.E-06 (0.83) | 7.E-06 (0.98) | |

TABLE 12-continued

| SEQ ID NO: | Sequence | A*0201 ED50 ($r^2$) | A*0301 ED50 ($r^2$) | A*1101 ED50 ($r^2$) | A*2402 ED50 ($r^2$) | B*0702 ED50 ($r^2$) | B*0801 ED50 ($r^2$) | B*1501 ED50 ($r^2$) |
|---|---|---|---|---|---|---|---|---|
| 41 | FPRPWLHGL | | | | | 4.E-04 (0.95) | 2.E-06 (0.96) | |
| 152 | FPRIWLHGL | | | | | 2.E-07 (0.72) | 2.E-06 (0.96) | 5.E-06 (0.98) |

Multi-parametric Analysis—iScore

Multi-parametric analysis was performed to integrate the half-life (t½) and ED50 parameters in an index (iScore). The iScore (Table 13) reflects the capability of a peptide to reconstitute with MHC molecules in a stable complex, defining its overall level of binding.

TABLE 13

| SEQ ID NO: | Sequence | A*0101 | A*0201 | A*0301 | A*1101 | A*2402 | B*0702 | B*0801 | B*1501 |
|---|---|---|---|---|---|---|---|---|---|
| 72 | ALFYKLDVV | 0 | 0.484 | 0 | 0 | 0 | 0 | 0 | 0 |
| 158 | ALFYKLDVI | 0 | 0.460 | 0 | 0 | 0.339 | 0 | 0 | 0 |
| 71 | KLAGRWPVK | 0 | 0.084 | 0.606 | 0.834 | 0 | 0 | 0 | 0 |
| 157 | KLAGRWPVT | 0 | 0.129 | 0 | 0.039 | 0 | 0 | 0 | 0 |
| 70 | VPLTEEAEL | 0 | 0 | 0 | 0 | 0 | 0 | 0 | 0 |
| 156 | VTLTEEAEL | 0 | 0.110 | 0 | 0 | 0 | 0 | 0 | 0 |
| 22 | YNEWTLELL | 0 | 0 | 0 | 0 | 0.071 | 0 | 0 | 0 |
| 155 | HNEWTLELL | 0 | 0 | 0 | 0 | 0 | 0 | 0 | 0 |
| 69 | CSSNITGLL | 0 | 0.081 | 0 | 0 | 0.016 | 0 | 0 | 0.067 |
| 154 | CSSNITGLI | 0 | 0.114 | 0 | 0 | 0.038 | 0 | 0 | 0.112 |
| 68 | RGRQKVVSL | 0 | 0 | 0 | 0 | 0 | 0.307 | 0.100 | 0.106 |
| 153 | RGRQKVVSI | 0 | 0 | 0 | 0 | 0.050 | 0.271 | 0.165 | 0 |
| 41 | FPRPWLHGL | 0 | 0 | 0 | 0 | 0.025 | 0.398 | 0 | 0 |
| 152 | FPRIWLHGL | 0 | 0 | 0 | 0 | 0 | 0.421 | 0.189 | 0 |

Figure 22:
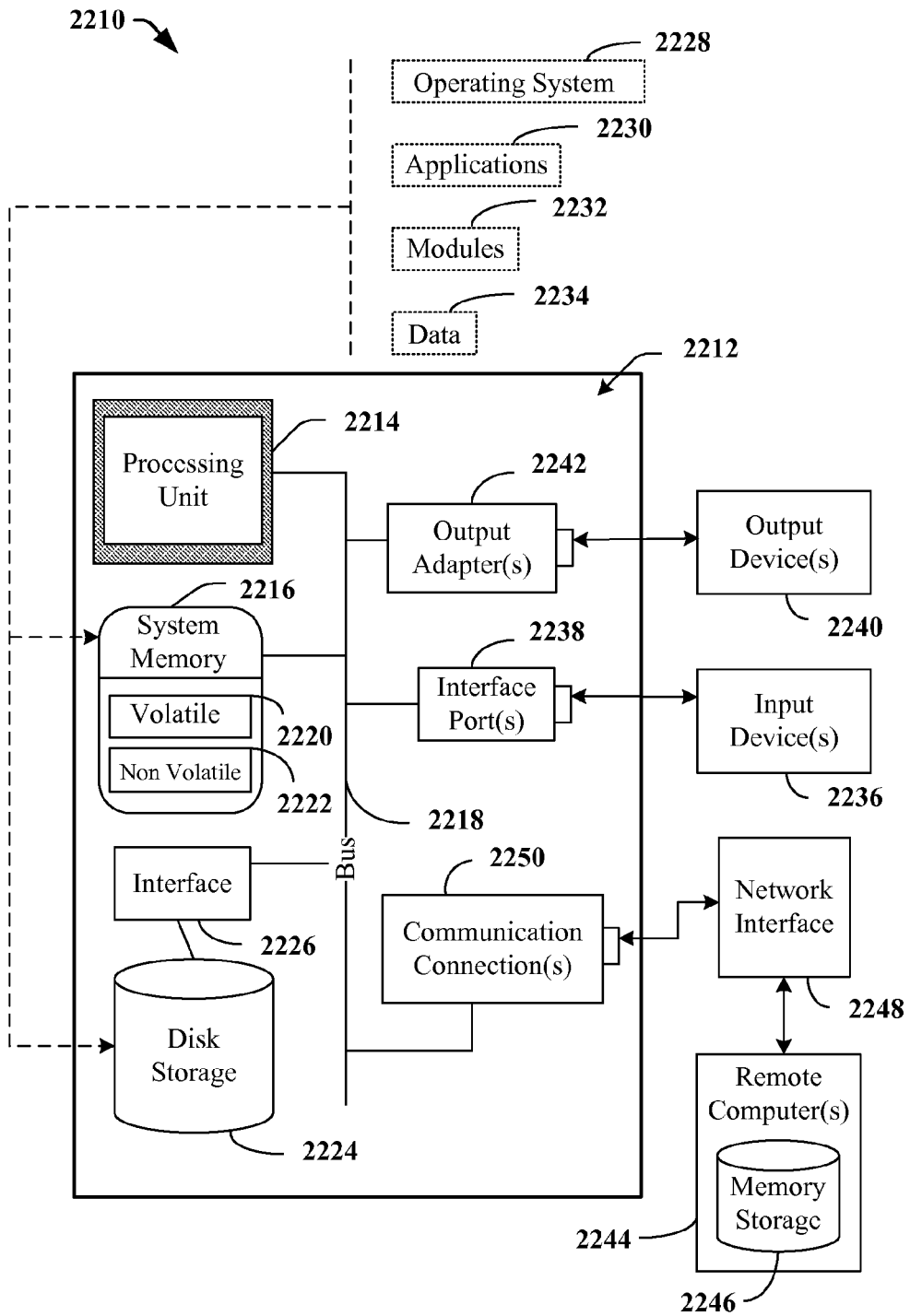
FIG. 22 illustrates an exemplary computing architecture that can be employed in connection with the subject matter described herein.
Figure 23:
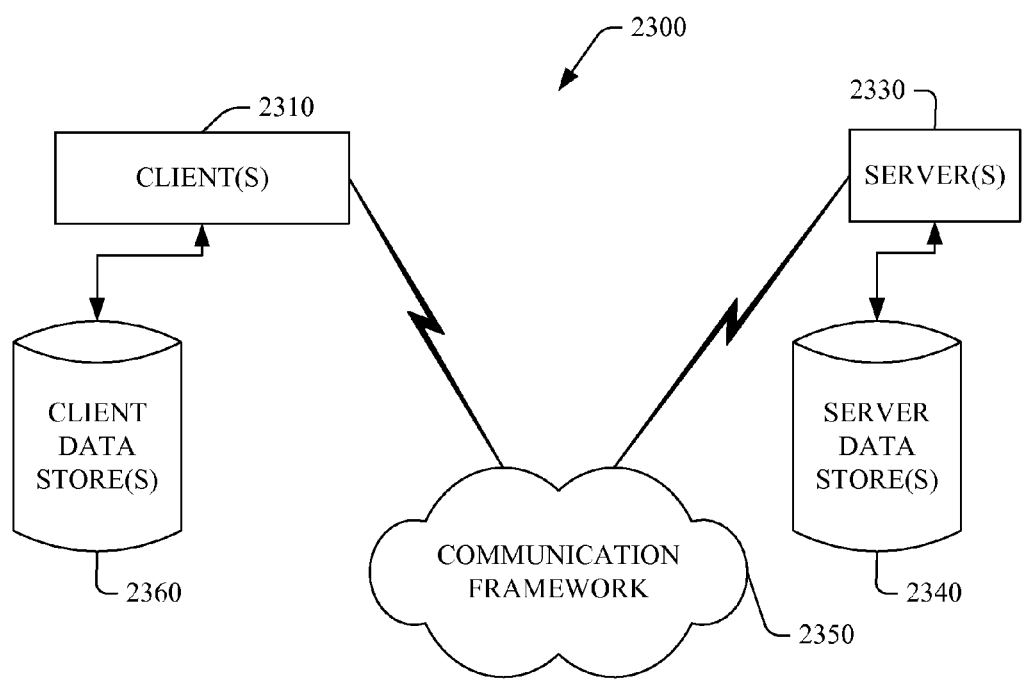
FIG. 23 illustrates an exemplary networking environment that can be employed in connection with the subject matter described herein.

FIGS. 22-23 and the following discussion is intended to provide a brief, general description of a suitable computing environment in which the various aspects of the subject matter described herein can be implemented. While the subject matter has been described above in the general context of computer-executable instructions of a computer program that runs on a local computer and/or remote computer, the invention also can be implemented in combination with other program modules. Generally, program modules include routines, programs, components, data structures, etc., that perform particular tasks and/or implement particular abstract data types.

Moreover, the subject matter can be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The subject matter can also be practiced in distributed computing environments such that certain tasks are performed by remote processing devices that are linked through a communications network. In a distributed computing environment, program modules may be located in local and/or remote memory storage devices. However, some, if not all, of the subject matter can be practiced on stand-alone computers.

As used in this application, the term "means" is intended to refer to a computer-related entity, either hardware, a combination of hardware and software, software, or software in execution. For example, a means may be, but is not limited to being, a process running on a processor, a processor, an object, an executable, a thread of execution, a program, and/or a computer. By way of illustration, both an application running on a server and the server can be a means. One or more means may reside within a process and/or thread of execution and a means may be localized on one computer and/or distributed between two or more computers. A "thread" is the entity within a process that the operating system kernel schedules for execution. As is well known in the art, each thread has an associated "context" which is the volatile data associated with the execution of the thread. A thread's context includes the contents of system registers and the virtual address belonging to the thread's process. Thus, the actual data comprising a thread's context varies as it executes.

As used in this application, the term "component" is intended to refer to a computer-related entity, either hardware, a combination of hardware and software, software, or software in execution. For example, a component may be, but is not limited to, a process running on a processor, a processor, an object, an executable, a thread of execution, a program, and a computer. By way of illustration, an application running on a server and/or the server can be a component. In addition, a component may include one or more subcomponents. One or more components may reside within a process and/or thread of execution and a component may be localized on one computer and/or distributed between two or more computers.

The subject matter described herein can operate in the general context of computer-executable instructions, such as program modules, executed by one or more components. Generally, program modules include routines, programs, objects, data structures, etc., that perform particular tasks or implement particular abstract data types. Typically, the functionality of the program modules may be combined or distributed as desired in various instances of the subject invention. The subject matter described herein may be embodied on a computer-readable medium having computer-executable instructions for implementing various aspects of the subject invention as well as signals manufactured to transmit such information, for instance, on a network.

FIG. 22 schematically illustrates an exemplary environment 2210 for implementing various aspects of the subject invention. The environment 2210 includes a computer 2212, which includes a processing unit 2214, a system memory 2216, and a system bus 2218. The system bus 2218 couples system components including, but not limited to, the system memory 2216 to the processing unit 2214. The processing unit 2214 can be any of various available processors. Dual microprocessors and other multiprocessor architectures also can be employed as the processing unit 2214.

The system bus 2218 can be any of several types of bus structure(s) including the memory bus or memory controller, a peripheral bus or external bus, and/or a local bus using any variety of available bus architectures including, but not limited to, 10-bit bus, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Universal Serial Bus (USB), Advanced Graphics Port (AGP), Personal Computer Memory Card International Association bus (PCMCIA), and Small Computer Systems Interface (SCSI).

The system memory 2216 includes volatile memory 2220 and nonvolatile memory 2222. The basic input/output system (BIOS), containing the basic routines to transfer information between elements within the computer 2212, such as during start-up, is stored in nonvolatile memory 2222. By way of illustration, and not limitation, nonvolatile memory 2222 can include read only memory (ROM), programmable ROM (PROM), electrically programmable ROM (EPROM), electrically erasable programmable ROM (EEPROM), or flash memory. Volatile memory 2220 includes random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and Rambus Direct RAM (RDRAM), direct Rambus dynamic RAM (DRDRAM), and Rambus dynamic RAM (RDRAM).

Computer 2212 also includes removable/non-removable, volatile/non-volatile computer storage media. FIG. 22 illustrates, for example a disk storage device 2224. Disk storage device 2224 includes, but is not limited to, devices like a magnetic disk drive, floppy disk drive, tape drive, Jaz drive, Zip drive, LS-100 drive, flash memory card, or memory stick. In addition, disk storage device 2224 can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage devices 2224 to the system bus 2218, a removable or non-removable interface is typically used such as interface 2226.

In addition to hardware components, FIG. 22 illustrates software that acts as an intermediary between users and the basic computer resources described in suitable operating environment 2210. Such software includes an operating system 2228. Operating system 2228, which can be stored on disk storage devices 2224, acts to control and allocate resources of the computer system 2212. System applications 2230 take advantage of the management of resources by operating system 2228 through program modules 2232 and program data 2234 stored either in system memory 2216 or on disk storage devices 2224. The subject invention can be implemented with various operating systems or combinations of operating systems.

A user enters commands or information into the computer 2212 through input device(s) 2236. Input devices 2236 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 2214 through the system bus 2218 via interface port(s) 2238. Interface port(s) 2238 include, for example, a serial port, a parallel port, a game port, and a universal serial bus (USB). Output device(s) 2240 use some of the same type of ports as input device(s) 2236. Thus, for example, a USB port may be used to provide input to computer 2212 and to output information from computer 2212 to an output device 2240. Output adapter 2242 is provided to illustrate that there are some output devices 2240 like monitors, speakers, and printers, among other output devices 2240, which require special adapters. The output adapters 2242 include, by way of illustration and not limitation, video and sound cards that provide a means of connection between the output device 2240 and the system bus 2218. It should be noted that other devices and/or systems of devices provide both input and output capabilities such as remote computer(s) 2244.

Computer 2212 can operate in a networked environment using logical connections to one or more remote computers, such as remote computer(s) 2244. The remote computer(s) 2244 can be a personal computer, a server, a router, a network PC, a workstation, a microprocessor based appliance, a peer device or other common network node and the like, and typically includes many or all of the elements described relative to computer 2212. For purposes of brevity, only a memory storage device 2246 is illustrated with remote computer(s) 2244. Remote computer(s) 2244 is logically connected to computer 2212 through a network interface 2248 and then physically connected via communication connection 2250. Network interface 2248 encompasses communication networks such as local-area networks (LAN) and wide-area networks (WAN). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit switching networks like Integrated Services Digital Networks (ISDN) and variations thereon, packet switching networks, and Digital Subscriber Lines (DSL).

Communication connection(s) 2250 refers to the hardware/software employed to connect the network interface 2248 to the bus 2218. While communication connection 2250 is shown for illustrative clarity inside computer 2212, it can also be external to computer 2212. The hardware/software necessary for connection to the network interface 2248 includes, for exemplary purposes only, internal and external technologies such as, modems including regular telephone grade modems, cable modems and DSL modems, ISDN adapters, and Ethernet cards.

FIG. 23 is a schematic block diagram of a sample-computing environment 2300 with which the present invention can interact. The system 2300 includes one or more client(s) 2310. The client(s) 2310 can be hardware and/or software (e.g., threads, processes, computing devices). The system 2300 also includes one or more server(s) 2330. The server(s) 2330 can also be hardware and/or software F (e.g., threads, processes, computing devices). The servers 2330 can house threads to perform transformations by employing the user interfaces, methods and systems described herein. One possible communication between a client 2310 and a server 2330 can be in the form of a data packet adapted to be transmitted between two or more computer processes. The system 2300 includes a communication framework 2350 that can be employed to facilitate communications between the client(s) 2310 and the server(s) 2330. The client(s) 2310 can connect to one or more client data store(s) 2360 that can be employed to store information local to the client(s) 2310. Similarly, the server(s) 2330 can connect to one or more server data store(s) 2340 that can be employed to store information local to the servers 2330.

As utilized in this application, terms "component," "system," "engine," and the like are intended to refer to a computer-related entity, either hardware, software (e.g., in execution), and/or firmware. For example, a component can be a process running on a processor, a processor, an object, an executable, a program, and/or a computer. By way of illustration, both an application running on a server and the server can be a component. One or more components can reside within a process and a component can be localized on one computer and/or distributed between two or more computers.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications, and variations that fall within the spirit and scope of the appended claims.

In particular and in regard to the various functions performed by the above described components, devices, circuits, systems and the like, the terms (including a reference to a "means") used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the invention. In this regard, it will also be recognized that the invention includes a system as well as a computer-readable medium having computer-executable instructions for performing the acts and/or events of the various methods of the invention.

While the subject matter described herein has been described in terms of various embodiments, it will be apparent to those of skill in the art that variations may be applied to the compositions and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention.

In addition, while a particular feature of the invention may have been disclosed with respect to only one of several implementations, such feature may be combined with one or more other features of the other implementations as may be desired and advantageous for any given or particular application. Furthermore, to the extent that the terms "includes," and "including" and variants thereof are used in either the detailed description or the claims, these terms are intended to be inclusive in a manner similar to the term "comprising."

What is claimed is:

1. Computer-executable instructions for performing a method of forecasting a portion of a target molecule anticipated to influence an organism's condition, the computer-executable instructions stored on computer-readable storage media, the method comprising:
employing population data to automatically analyze one or more areas of the target molecule to determine the portion of the target molecule anticipated to influence the organism's condition, the population data pertaining to at least one relationship between at least one diverse organism trait and the target molecule, the target molecule comprising an HLA or an MHC molecule and the organism's condition being Human Immunodeficiency Virus (HIV);
building a plurality of patches from sequence data by iteratively increasing a size of a patch while decreasing an associated free energy of the patch;
utilizing the plurality of patches to generate an epitome most likely to target or identify the organism's condition, the epitome being a sequence that includes some or all of subsequences from the set of sequence data; and
employing a cost function that measures a similarity of the sequence data with an estimate of the epitome.

2. The computer-executable instructions of claim 1, wherein employing the population data to automatically analyze one or more areas of the target molecule comprises learning a classifier according to the population data and applying the classifier to search the target molecule in a vicinity of a site corresponding to a window of length that is determined by the at least one relationship.

3. The computer-executable instructions of claim 2, wherein the portion of the target molecule anticipated to influence the organism's condition is an epitope.

4. The computer-executable instructions of claim 3, wherein the vicinity of a site determined by the at least one relationship comprises a window of a length sufficient to include flanking positions of the epitope.

5. The computer-executable instructions of claim 4, wherein the window is about 33 amino acids in length.

6. The computer-executable instructions of claim 1, wherein the at least one relationship is between a mutation and an MHC-type.

7. The computer-executable instructions of claim 1, wherein the organism's condition is one of a malignancy and an infection.

8. The computer-executable instructions of claim 7, wherein the infection is Acquired Immunodeficiency Syndrome.

9. A method comprising:
learning, by a computing device, a classifier based on population data;
applying, by the computing device, the classifier to search a portion of an MHC molecule;
forecasting, by the computing device, an anticipated influence of the portion of the MHC molecule on a human condition, the human condition being Acquired Immunodeficiency Syndrome (AIDS); and
designing, by the computing device, an AIDS vaccine cocktail by:
obtaining sequence data of contiguous amino acid subsequences associated with AIDS;
building a plurality of disparate sized patches from the sequence data by iteratively increasing a size of a patch while decreasing an associated free energy of the patch; and
aggregating the plurality of disparate sized patches to form the AIDS vaccine cocktail by adding a most frequent patch during each iteration.

10. The method as recited in claim 9, wherein the population data pertains to a relationship between a diverse trait of the human condition and the target molecule.

11. The method as recited in claim 9, wherein the portion of the MHC molecule is an epitope.

12. The method as recited in claim 11, wherein the forecasting further comprises:
identifying a window of length sufficient to include regions flanking the epitope; and
searching the window of length.

13. The method as recited in claim 12, wherein:
the window of length is 33 amino acids in length;
the epitope is 9 amino acids in length; and
each region flanking the epitope is 12 amino acids in length.

14. A method comprising:
identifying, by a computing device, population data pertaining to at least one relationship between at least one diverse organism trait and a target molecule, the target molecule comprising an HLA or an MHC molecule and the organism's condition being Human Immunodeficiency Virus (HIV);
employing, by the computing device, population data to automatically analyze one or more areas of the target molecule to determine a portion of the target molecule that is anticipated to influence the organism's condition;
receiving, by the computing device, one or more patches corresponding to sequences of variable length, the one or more patches being built from sequence data by iteratively increasing a size of a patch while decreasing an associated free energy of the patch; and
utilizing, by the computing device, the one or more patches to generate a vaccine cocktail that is targeted towards the organism's condition.

15. The method as recited in claim 14, wherein the employing the population data to automatically analyze one or more areas of the target molecule includes learning a classifier according to the population data and applying the classifier to search the target molecule in a vicinity of a site corresponding to a window of length that is determined by the at least one relationship.

16. The method as recited in claim 14, wherein the one or more patches correspond to sequences of DNA, RNA, or a protein.

17. The method as recited in claim 14, wherein the vaccine cocktail provides for higher epitope coverage and a larger amount of local diversity in comparison to vaccine cocktails generated by phylogenetic tree nodes.

* * * * *